US009181568B2

(12) United States Patent
Brown et al.

(10) Patent No.: US 9,181,568 B2
(45) Date of Patent: Nov. 10, 2015

(54) CELL SYSTEMS AND METHODS FOR IMPROVING FATTY ACID SYNTHESIS BY EXPRESSION OF DEHYDROGENASES

(75) Inventors: Robert Christopher Brown, San Diego, CA (US); Jennifer Coppersmith, San Diego, CA (US); Prachee Prakash, San Diego, CA (US); Srividya Akella, San Diego, CA (US); Rekha Seshadri, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 619 days.

(21) Appl. No.: 13/453,235

(22) Filed: Apr. 23, 2012

(65) Prior Publication Data

US 2013/0280793 A1  Oct. 24, 2013

(51) Int. Cl.
*C12P 7/64* (2006.01)
*C12N 9/04* (2006.01)

(52) U.S. Cl.
CPC ............... *C12P 7/64* (2013.01); *C12N 9/0006* (2013.01); *C12Y 101/01044* (2013.01); *C12Y 101/99006* (2013.01); *C12Y 102/01* (2013.01)

(58) Field of Classification Search
None
See application file for complete search history.

(56) References Cited

U.S. PATENT DOCUMENTS

| | | | |
|---|---|---|---|
| 5,447,858 A | 9/1995 | Key et al. | 435/172.3 |
| 5,455,167 A | 10/1995 | Voelker et al. | 435/172.3 |
| 5,464,758 A | 11/1995 | Gossen et al. | 435/69.1 |
| 5,639,952 A | 6/1997 | Quail et al. | 800/205 |
| 5,654,495 A | 8/1997 | Voelker et al. | 800/250 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,814,618 A | 9/1998 | Bujard et al. | 514/44 |
| 5,851,796 A | 12/1998 | Schatz | 435/69.1 |
| 6,143,538 A | 11/2000 | Somerville et al. | 435/189 |
| 6,379,945 B1 | 4/2002 | Jepson et al. | 435/243 |
| 6,410,828 B1 | 6/2002 | Armstrong et al. | 800/287 |
| 7,294,506 B2 | 11/2007 | Daniell et al. | 435/320.1 |
| 7,326,557 B2 | 2/2008 | San et al. | 435/252.3 |
| 7,785,861 B2 | 8/2010 | Devroe et al. | 453/252.3 |
| 7,968,321 B1 | 6/2011 | Green et al. | 435/161 |
| 8,110,093 B2 | 2/2012 | Friedman et al. | 208/118 |
| 8,227,237 B2 | 7/2012 | Reppas et al. | 435/257.2 |
| 8,399,227 B2 | 3/2013 | Berry et al. | 435/134 |
| 2003/0233675 A1 | 12/2003 | Cao et al. | 800/279 |
| 2005/0196866 A1 | 9/2005 | San et al. | 435/488 |
| 2007/0087403 A1 | 4/2007 | Bestel-Corre et al. | 435/52 |
| 2007/0118916 A1 | 5/2007 | Puzio et al. | 800/278 |
| 2007/0184538 A1 | 8/2007 | Damude et al. | 435/134 |
| 2009/0191599 A1 | 7/2009 | Devroe et al. | 435/101 |
| 2009/0298143 A1 | 12/2009 | Roessler et al. | 435/134 |
| 2010/0105963 A1 | 4/2010 | Hu | 568/840 |
| 2010/0159110 A1 | 6/2010 | Ochiai et al. | 426/601 |
| 2010/0221798 A1 | 9/2010 | Schirmer et al. | 435/147 |
| 2010/0235934 A1 | 9/2010 | Friedman et al. | 800/13 |
| 2010/0255551 A1 | 10/2010 | Roberts et al. | 435/134 |
| 2011/0008861 A1* | 1/2011 | Berry et al. | 435/161 |
| 2011/0020883 A1 | 1/2011 | Roessler et al. | 435/134 |
| 2011/0124071 A1 | 5/2011 | Schirmer et al. | 435/167 |
| 2011/0218354 A1 | 9/2011 | Savage et al. | 560/129 |
| 2011/0223641 A1 | 9/2011 | Stephanopoulos et al. | 435/134 |
| 2011/0244512 A1 | 10/2011 | Hong et al. | 435/41 |
| 2011/0250659 A1 | 10/2011 | Roberts et al. | 435/134 |
| 2011/0252501 A1* | 10/2011 | Abad et al. | 800/275 |

FOREIGN PATENT DOCUMENTS

| | | | | |
|---|---|---|---|---|
| WO | WO 00/62601 | 10/2000 | | A01H 13/00 |
| WO | WO 01/07626 | 2/2001 | | C12N 15/31 |
| WO | WO 03/091413 | 11/2003 | | |
| WO | WO 2005/005643 | 1/2005 | | C12N 15/82 |
| WO | WO 2007/133558 | 11/2007 | | E21B 37/00 |
| WO | WO 2009/140696 | 11/2009 | | C12N 9/04 |
| WO | WO 2010/042664 | 4/2010 | | C07C 47/02 |
| WO | WO 2010/075483 | 7/2010 | | C10L 1/02 |
| WO | WO 2010/135624 | 11/2010 | | C07C 31/125 |
| WO | WO 2011/062987 | 5/2011 | | C12P 5/02 |
| WO | WO 2011/066137 | 6/2011 | | A01N 43/00 |
| WO | WO 2011/123407 | 10/2011 | | C12P 1/00 |

OTHER PUBLICATIONS

Sequence accession F2IXS1 ( May 31, 2011), appended to the office action.*
Sequence accession AAU35307 (Oct. 15, 2009), appended to the office action.*
Abe, J., et al. (2008), "Expression of exogenous genes under the control of endogenous HSP70 and CAB promoters in the *Closterium peracerosum-strigosum-littorale* complex", *Plant Cell Physiol*, 49(4): 625-632.
Alonso, A., et al. (2010), "Understanding fatty acid synthesis in developing maize embryos using metabolic flux analysis", *Metabolic Engineering*, 12: 488-497.
Alonso, A., et al. (2011), "Central metabolic fluxes in the endosperm of developing maize seeds and their implications for metabolic engineering", *Metabolic Engineering*, 13(1): 96-107.
Altschul, S., et al. (1997), "Gapped BLAST and PSI-BLAST: a new generation of protein database search programs", *Nucleic Acids Research*, 25(17): 3389-3402.
Bateman, A., et al. (2000), "The pfam protein families database", Nucleic Acids Research, 28(1):263-266.
Bateman, A., et al. (2004), "The pfam protein families database", Nucleic Acids Research, 32: Database Issue: D138-D141.

(Continued)

*Primary Examiner* — Elizabeth McElwain
(74) *Attorney, Agent, or Firm* — Harness, Dickey and Pierce, P.L.C.

(57) ABSTRACT

The invention relates to methods for producing lipids such as fatty acid products in recombinant host cells engineered to express a non-native gene encoding a dehydrogenase. The recombinant microorganisms are able to proliferate at a higher rate as compared with microorganisms that do not express a non-native dehydrogenase gene, and cultures of microorganisms that are engineered for lipid production and that express a non-native dehydrogenase produce more lipid than cultures of control microorganisms that do not include a non-native dehydrogenase gene.

42 Claims, 5 Drawing Sheets

(56) References Cited

OTHER PUBLICATIONS

Berrios-Rivera, S., et al. (2002), "Metabolic engineering of *Escherichia coli*: increase of NADH availability by overexpressing an NAD+-dependent formate dehydrogenase", *Metabolic Engineering*, 4: 217-229.

Berrios-Rivera, S., et al. (2002), "The effect of Increasing NADH availability of the redistribution of metabolic fluxes in *Escherichia coli* chemostat cultures", *Metabolic Engineering*, 4: 230-237.

Berrios-Rivera, S., et al. (2004), "Effect of different levels of NADH availability on metabolite distribution in *Escherichia coli* fermentation in minimal and complex media",*Applied Genetics and Molecular Biotechnology*, 65: 426-432.

Broedel, S., et al. (1990), "Genetic tagging, cloning, and DNA sequence of the *Synechococcus* sp. strain PCC 7942 gene (*gnd*) encoding 6-physphogluconate dehydrogenase", *Journal of Bacteriology*, 172(7): 4023-4031.

Buikema, W., et al. (2001), "Expression of the anabaena hetR gene from a copper-regulated promoter leads to heterocyst differentiation under repressing conditions", *Proc. Natl. Acad. Sciences* USA 98(5): 2729-2734.

Cheng, J., et al. (2004), "Mammalian wax biosynthesis", *The Journal of Biological Chemistry*, 279(36): 37798-37807.

Di Costanzo, L., et al. (2007), "Crystal structure of lactaldehyde dehydrogenase from *Escherichia coli* and inferences regarding substrate and cofactor specificity", *J Mol Biol*, 366(2): 481-493.

Domenech, J., et al. (2006), "A new $_D$ 2-hydroxyacid dehydrogenase with dual coenzyme-specificity from *Haloferax mediterranei*, sequence analysis and heterologous overexpression", *Biochimica et Biophysica Acta*, 1760: 1667-1674.

Domergue, F., et al., (2010), "Three arabidopsis fatty acyl-coenzyme a reductases, FAR1, FAR4, and FAR5, generate primary fatty alcohols associated with suberin deposition", *Plant Physiology*, 153: 1539-1554.

Finn, R., et al. (2006), "Pfam: clans, web tools and services", *Nucleic Acids Research*, 34: Database Issue 34:D247-D251.

Finn, R., et al. (2010), "The pham protein families database", *Nucleic Acids Research*, 38: Database Issue 38:D211-D222.

Graupner, M., et al., (2000), "Identification of an archaeal 2-hydroxy acid dehydrogenase catalyzing reactions involved in coenzyme biosynthesis in methanoarchaea", *Journal of Bacteriology*, 182(13): 3688-3692.

Habenicht, A., et al. (1997), Sequence of the non-phosphorylating glyceraldehyde-3-phosphate dehydrogenase from *Nicotiana plumbaginifolia* and phylogenetic origin of the gene family, *Gene*, 237-243.

Hellmann, A., et al. (1997), "Gene replacement by homologous recombination in the multicellular green alga *Volvox carter*," *Proc. Natl. Acad. Sci USA*, 94:7469-7474.

Henikoff, S., et al. (1992), "Amino acid substitution matrices from protein blocks", *Proc. Natl. Acad. Sci USA*, 89:10915-10919.

Holtzapple, E., et al. (2007), "Biosynthesis of isoprenoid wax ester in *Marinobacter hydrocarbonoclasticus* DSM 8798: identification and characterization of isoprenoid coenzyme a synthetase and wax ester synthases", *Journal of Bacteriology*, 189(10): 3804-3812.

Honsho, M., et al. (2010), "Posttranslational regulation of Fatty Acyl-CoA reductase 1, FAR1, Controls Ether glycerophospholipid synthesis", *Journal of Biological Chemistry*, 285(12): 8537-8542.

Hu, Q., et al. (2008), "Microalgal triacylglycerols as feedstocks for biofuel production: perspectives and advances",*The Plant Journal*, 54: 621-639.

Iddar, A., et al. (2005), "Widespread occurrence of non-phosphorylating glyceraldehyde-3-phosphate dehydrogenase among gram-positive bacteria", *International Microbiology*, 8:251-258.

Ishige, T., et al. (2002), "Wax ester production from *n*-Alkanes by *Acinetobacter* sp. strain M-1: ultrastructure of cellular inclusions and role of acyl coenzyme a reductase", *Applied and Environmental Microbiology*, 68(3): 1192-1195.

Iwai, M., et al. (2004), "Improved genetic transformation of the thermophilic cyanobacterium, thermosynechoccus elongates BP-1", *Plant Cell Physiol*. 45(2):171-175.

Kaczmarzyk, D., et al. (2010), "Fatty acid activation in cyanobacteria mediated by acyl-acyl carrier protein synthetase enables fatty acid recycling", *Plant Physiology*, 152: 1598-1610.

Kalscheuer, R., et al. (2003), "A novel bifunctional wax ester synthase/Acyl-CoA:DiacylgIcerol acyltransferase mediates wax ester and triacylglycerol biosynthesis in *Acinetobacter calcoaceticus* ADP1", *The Journal of Biological Chemistry*, 278(10): 8075-8082.

Kalscheuer, R., et al, (2006), "Neutral lipid biosynthesis in engineered *Escherichia coli*: jojoba oil-like wax esters and fatty acid butyl esters", *Applied and Environmental Microbiology*, 72(2): 1373-1379.

Karlin, S., et al., (1990), "Methods for assessing the statistical significance of molecular sequence features by using general scoring schemes", *Proc. Natl. Acad. Sci. USA*, 87: 2264-2268.

Kindle, K., et al. (1989), "Stable nuclear transformation of *Chlamydomonas* using the *Chlamydomonas* gene for nitrate reductase", *The Journal of Cell Biology*, 109 (6, Part 1), 2589-2601.

King, A., et al. (2007), "Cuticular wax biosynthesis in petunia petals: cloning and characterization of an alcohol-acyltransferase that synthesizes wax-esters", *Planta*, 226: 381-394.

Lardizabal, K., et al. (2000), "Purification of a jojoba embryo wax synthase, cloning of its cDNA, and production of high levels of wax in seeds of transgenic arabidopsis", *Plant Physiology*, 122: 645-655.

Lem, N., et al. (1984), "InVitro fatty acid synthesis and complex lipid metabolism the cyanobacterium *Anabaena variabilis*", Plant Physiol, 74: 134-138.

Li, F., et al. (2008), "Identification of the wax ester synthase/acyl-coenzyme A:diacylglycerol acyltransferase WSD1 required for stem wax ester biosynthesis in arabidopsis", *Plant Physiology*, 148: 97-107.

Li, Z., et al. (2012), "Overexpression of malic enzyme (ME) of *Mucor circinelloides* improved lipid accumulation in engineered *Rhodotorula glutinis*", *Applied Genetics and Molecular Biotechnology*, DOI 10.2007/s00253-012-4571-5.

Liénard, M., et al. (2010), "Evolution of multicomponent pheromone signals in small ermine moths involves a single fatty-acyl reductase gene", *PNAS*, 107(24): 10955-10960.

Liu, X., et al. (2009), "Nickel-inducible lysis system in *Synechocystis* sp. PCC 6803", *PNAS*, 106: 21550-21554.

Lo, H., et al. (2010), "Gene cloning and biochemical characterization of a NAP(P)⁺-Dependent aldehyde dehydrogenase from *Bacillus licheniformis*", *Mol Biotechnol* 46: 157-167.

Maes, L., et al. (2011), "Dissection of the phytohormonal regulation of trichome formation and biosynthesis of the antimalarial compound artemisinin in *Artemisia annua* plants", *New Phytologist* 189: 176-189.

Méndez-Alvarez, S., et al. (1994), "Transformation of *Chlorobium limicola* by a plasmid that confers the ability to utilize thiosulfate" *Journal of Bacteriology*,176(23):7395-7397.

Metz, J., et al. (2000), "Purification of a jojoba embryo fatty acyl-coenzyme a reductase and expression of it's cDNA in high erucic acid rapeseed", *Plant Physiology*, 122: 635-644.

No, D., et al. (1996), "Ecdysone-inducible gene expression in mammalian cells and transgenic mice", *Proc. Natl. Acad. Sci.* USA, 93: 3346-3351.

Noctor, G., et al. (2006), "NAD(P) synthesis and pyridine nucleotide cycling in plants and their potential importance in stress conditions", *Journal of Experimental Botany*, 57(8): 1603-1620.

Ohnuma M., et al. (2008), "Polyethylene glycol (PEG)-mediated transient gene expression in a red alga, *Cyanidioschyzon merolae* 10D", *Plant Cell Physiol*. 49(1):117-120.

Perrone, C., et al. (1998), "The *Chlamydomonas* IDA7 locus encodes a 140 kDa dynein intermediate chain required to assemble the I1 inner arm complex", *Molecular biology of the Cell*, 9:3351-3365.

Poulsen, B., et al. (2005), "Increased NADPH concentration obtained by metabolic engineering of the pentose phosphate pathway in *Aspergillus niger*", *FEBS Journal*, 272: 1313-1325.

Quinn, J., et al. (2003), "Copper response element and Crr1-dependent Ni² —responsive promoter for induced, reversible gene expression in *Chlamydomonas reinhardtii*" *Eukaryotic Cell*, 2(5): 995-1002.

(56) References Cited

OTHER PUBLICATIONS

Quintana, N., et al. (2011), "Renewable energy from cyanobacteria: energy production optimization by metabolic pathway engineering", *Appl Microbiol Biotechnol*, 91: 471-490.

Ramesh, V., et al. (2004), "A simple method for chloroplast transformation in *Chlamydomonas reinhardtii*" *Methods in Molecular Biology*, 274:301-307.

Ravindran, C., et al. (2006), "Electroporation as a tool to transfer the plasmid pRL489 in *Oscillatoria* MKU 277" *Journal of Microbiological Methods*, 66:174-176.

Rowland, O., et al. (2006), "CER4 encodes an alcohol-forming fatty acyl-coenzyme a reductase involved in cuticular wax production in arabidopis", *Plant Physiology*, 142: 866-877.

Ruffing, A. (2011), "Engineered cyanobacteria, teaching an old bug new tricks", *Bioengineered Bugs*, 2(3): 136-149.

Sànchez, A., et al. (2005), "Effect of different levels of NADH availability on metabolic fluxes of *Escherichia coli* chemostat cultures in defined medium", *Journal of Biotechnology*, 117: 395-405.

Schroda, M., et al. (2000), "The HSP70A promoter as a tool for improved expression of transgenes in *Chlamydomonas*", *The Plant Journal*, 21(2):121-131.

Shinoda, T., et al., (2005), "Distinct conformation-mediated functions of an active site loop in the catalytic reactions of NAD-dependent $_D$-Lactate dehydrogenase and formate Dehydrogenase", *The Journal of Biological Chemistry*, 280(17): 17068-17075.

Sonnhammer, E., et al. (1998), "Pfam: multiple sequence alignments and HMM-profiles of protein domains" *Nucleic Acids Research* 26(1):320-322.

Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.

Stemmer, W. (1994), "DNA shuffling by random fragmentation and reassembly: In vitro recombination for molecular evolution", *Proc. Natl. Acad. Sci. USA*, 91: 10747-10751.

Sun, Y., et al. (2006), "Functional complementation of a nitrate reductase defective mutant of a green alga *Dunaliella viridis* by introducing the nitrate reductase gene", *Gene* 377:140-149.

Talfournier, F., et al. (2011), "Methylomalonate-semialdehyde dehydrogenase from *Bacillus subtilis*", *The Journal of Biological Chemistry*, 286(25): 21971-21981.

Tan, C., et al. (2005), "Establishment of a micro-particle bombardment transformation system for *Dunaliella saline*", *The Journal of Microbiology* 43(4):361-365.

Terrawanichpan, P., et al. (2010), "A fatty acyl-CoA reductase highly expressed in the head of honey bee (*Apis mellifera*) involves biosynthesis of a wide range of aliphatic fatty alcohols", *Insect Biochemistry and Molecular Biology*, 40: 641-649.

Wolk, P., et al. (1984), "Construction of shuttle vectors capable of conjugative transfer from *Escherichia coli* to nitrogen-fixing filamentous cyanobacteria", *Proc. Natl. Acad. Sci.* USA, 81: 1561-1565.

Yang, Z., et al. (2002), "Structural studies of the pigeon cytosolic NADP+-dependent malic enzyme", *Protein Science*, 11: 332-341.

Yen, C., et al. (2005), "A human skin multifunctional O-acyltransferase that catalyzes the synthesis of acylglycerols, waxes, and retinyl esters", *Journal of Lipid Research* 46: 2388-2397.

Zhang, Y., et al. (2007), Malic enzyme: the controlling activity for lipid production? Overexpression of malic enzyme in *Mucor circinelloides* leads to a 2.5-fold increase in lipid accumulation, *Microbiology*, 153: 2013-2025.

Zhang, Y., et al. (2009), "Introduction of an NADH regeneration system into *Klebsiella oxytoca* leads to an enhanced oxidative and reductive metabolism of glycerol" Metabolic Engineering, 11: 101-106.

Lan, E., et al. (2012), "ATP drives direct photosynthetic production of 1-butanol in cyanobacteria", *PNAS*, 109(16), 6018-6023.

International Search Report and Written Opinion dated Apr. 22, 2013 issued in PCT/US2012/067901.

International Preliminary Report on Patentability dated Nov. 6, 2014 issued in PCT Patent Application No. PCT/US2012/067901.

\* cited by examiner

CELL SYSTEMS AND METHODS FOR IMPROVING FATTY ACID SYNTHESIS BY EXPRESSION OF DEHYDROGENASES

REFERENCE TO A SEQUENCE LISTING

This application contains references to amino acid sequences and/or nucleic acid sequences which have been submitted concurrently herewith as the sequence listing text file "60952161_1.txt", file size 80 KiloBytes (KB), created on Apr. 18, 2012. The aforementioned sequence listing is hereby incorporated by reference in its entirety pursuant to 37 C.F.R. §1.52(e)(5).

FIELD OF THE INVENTION

The present invention relates, in some embodiments, to the engineering of a metabolic pathway in a photosynthetic microorganism. Specifically, the invention relates to engineering pathways for the synthesis of fatty acids, fatty acid derivatives, and/or lipids. The present invention also relates to methods, microorganisms, and nucleic acid molecules for producing lipids, such as fatty acid products, in photosynthetic microorganisms, which can be used for a variety of products, including biofuels.

BACKGROUND OF THE INVENTION

Fossil fuel is a general term for buried combustible geologic deposits of organic materials formed from decayed plants and animals that have been converted to crude oil, coal, natural gas, or heavy oils by exposure to heat and pressure in the earth's crust over hundreds of millions of years. Fossil fuels are a finite, non-renewable resource.

Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Cost-effective alternatives to current sources of supply could help mitigate the upward pressure on energy and these raw material costs. Major efforts to this end are focused on the microbial production of high-energy fuels by cost-effective consolidated bioprocesses. However, some alternatives to fossils fuels production, such as fermentation-based approaches for generating combustible products rely on the use of a large quantity of carbohydrate-rich feedstock such as sugar cane, rice, corn, or the like. Use of such resources to produce combustible fuel has the undesirable consequence of increasing the market pressures on feed stocks, driving up the price of the world's food supply.

Fatty acids are composed of long alkyl chains and represent nature's petroleum, being a primary metabolite used by cells for both chemical and energy storage functions. These energy-rich molecules are today isolated from plant and animal oils for a diverse set of products ranging from fuels to oleochemicals. A more scalable, controllable and economical route to this important class of chemicals would be beneficial to the development of renewable energy sources.

SUMMARY OF THE INVENTION

In one aspect the invention provides a method of producing a lipid where the method includes providing a culture of a recombinant microorganism that includes a non-native gene encoding a dehydrogenase, and allowing the microorganism to proliferate under conditions in which the non-native gene is expressed, where the culture produces at least one lipid. Preferably, the culture produces a greater amount of the lipid than the amount of lipid produced by a control culture of a control microorganism identical in all respects to the recombinant microorganism that expresses a non-native dehydrogenase gene, except that the control microorganism does not express the gene encoding a non-native dehydrogenase. The recombinant microorganism that expresses a non-native gene encoding a dehydrogenase and produces a lipid can have a higher proliferation rate than a control microorganism that does not express a non-native dehydrogenase gene. The lipid produced by the recombinant microorganism can be any lipid, and can preferably be a fatty acid product, e.g., a fatty acid, fatty acid derivative, or a triglyceride. Additionally, the recombinant microorganism may include an additional non-native gene that encodes a polypeptide that participates in the biosynthesis of a lipid. The recombinant microorganism that expresses the non-native dehydrogenase gene can be cultured in a suitable culture medium, for example, a culture medium that supports growth and/or proliferation of the recombinant microorganism. The method can further include isolating at least one lipid from the culture.

Also provided herein, in certain aspects, is a method of improving the propagation and/or proliferation rate of a microorganism that produces a lipid, in which the method includes expressing a recombinant nucleic acid molecule that encodes a dehydrogenase in a microorganism that produces a lipid, and culturing the microorganism under conditions that support the propagation of the microorganism, wherein the propagation and/or proliferation rate of the microorganism is greater than that of a control microorganism that is cultured under the same conditions and is identical in all respects to the recombinant microorganism, except that the control microorganism does not express a recombinant nucleic acid molecule that encodes a dehydrogenase. Additionally the microorganism can include at least one additional non-native gene, in which the additional non-native gene(s) encode one or more polypeptides that participate in the synthesis of a lipid.

The dehydrogenase encoded by the non-native gene or recombinant nucleic acid molecule can be a dehydrogenase that can use NADP in oxidation reactions. Additionally or alternatively, the non-native gene can encode a dehydrogenase that is heterologous (derived from a different species) or homologous (derived from the same species) with respect to the host microorganism, and in certain aspects the non-native gene can be an endogenous gene engineered for overexpression in the host microorganism. In various examples, the dehydrogenase can be an aldehyde dehydrogenase (including, for example, a methylmalonate semialdehyde dehydrogenase or a non-phosphorylating glyceraldehyde-3-phosphate dehydrogenase (EC 1.2.1.9)), a D-2-hydroxyacid dehydrogenase, a glucose-6-phosphate dehydrogenase, a 6-phosphogluconate dehydrogenase, a sorbitol dehydrogenase, an isocitrate dehydrogenase, or a malic enzyme. For example, the recombinant microorganism can include a non-native gene encoding an aldehyde dehydrogenase, which in some examples can include an amino acid sequence having at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:4, SEQ ID NO:4, or SEQ ID NO:7, or an active fragment thereof. Alternatively or in addition, the recombinant microorganism can include a non-native gene encoding a methylmalonate semialdehyde dehydrogenase, and in some examples can be a methylmalonate semialdehyde dehydrogenase that includes an amino acid sequence having at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:18 or SEQ ID NO:19, or an active fragment thereof. Alternatively or in addition, the dehydrogenase can be a D-2-hydroxyacid dehydrogenase, and in some examples can be a D-2-hydroxyacid dehydrogenase that includes an amino acid sequence that has at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:2, SEQ ID NO:29, SEQ ID NO:15, or SEQ ID NO:16 or an active fragment thereof. Alternatively or in addition, the recombinant microorganism can include a non-native gene encoding a 6-phosphogluconate dehydrogenase. The 6-phosphogluconate dehydrogenase in some examples can include an amino acid sequence that has at least 50%, at least 55%, at least 60%, at least 65%, at least 70%, at least 75%, at least 80%, at least 85%, at least 90%, at least 95%, or at least 99% sequence identity to the amino acid sequence of to SEQ ID NO:10, SEQ ID NO:11, or SEQ ID NO:13, or an active fragment thereof.

The microorganism that includes the non-native dehydrogenase gene can be a fungus, bacterium, or heterokont, and can be, for example, a photosynthetic microorganism, such as a microalga or cyanobacterium. For example, the microorganism can be a microalga that is a species of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox*. Alternatively, the microorganism can be a cyanobacterium and can be a species of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus*.

A photosynthetic host microorganism of the invention can be cultured photoautotrophically for the production of a lipid, for example using inorganic carbon as substantially the sole source of carbon in the culture medium. The microorganism can be provided with inorganic carbon in the culture medium, for example, $CO_2$ and/or carbonate can be supplied to the culture during the culture period.

A recombinant microorganism comprising a non-native gene encoding a dehydrogenase, which may be a photosynthetic microorganism, can further include a second non-native gene encoding a polypeptide that participates in the production of a lipid, such as a fatty acid product or a triglyceride. As nonlimiting examples, a polypeptide that participates in the production of a lipid can be an acetyl-CoA carboxylase, a malonyl CoA: ACP transacylase, a beta-ketoacyl-ACP synthase, an acyl-ACP thioesterase, an acyl-CoA thioesterase, a hydroxylbenzoyl thioesterase, a polypeptide having lipolytic activity, an acyl-CoA synthetase, an acyl-CoA reductase, an acyl-ACP reductase, a carboxylic acid reductase, a wax synthase, a decarboxylase, a decarbonylase, a glycerolphosphate acyltransferase (GPAT), a lysophosphatidic acid acyltransferase (LPAAT), a phosphatidic acid phosphatase (PA), or a diacylglycerol O-acyltransferase (DGAT). The recombinant microorganism can produce, for example, a fatty acid, a fatty acid derivative such as a fatty aldehyde, a fatty alcohol, a fatty acid ester, a wax ester, an alkane, or an alkene, or can produce a triglyceride, any of which may be, in particular examples, a lipid that is not naturally produced by the microorganism when not transformed with a gene that participates in production of the lipid. For example, the recombinant microorganism can include a second non-native gene encoding a thioesterase, and can produce a fatty acid product, e.g., a free fatty acid or a fatty acid derivative. The fatty acid product can include at least one acyl chain of C8-C14, for example, of C12-C24, such as from C12-C18.

The recombinant microorganism that includes a first non-native gene encoding a dehydrogenase and a second non-native gene encoding a polypeptide that participates in the production of a lipid can have a higher proliferation rate than a control microorganism identical in all respects to the recombinant microorganism except that it does not include a non-native gene encoding a dehydrogenase. For example, the recombinant microorganism that includes a non-native dehydrogenase gene and a non-native gene encoding a polypeptide for lipid biosynthesis can have a higher proliferation rate during a culture period in which the dehydrogenase gene is expressed and the recombinant microorganism produces a lipid. The recombinant microorganism may be a photosynthetic microorganism, and in particular examples, can have a higher proliferation rate than a control microorganism that does not include or does not express the non-native dehydrogenase gene when cultured under photoautotrophic conditions in which the recombinant microorganism produces at least one lipid, such as, for example, a fatty acid product, which in certain examples may be a fatty acid product not naturally made by the photosynthetic microorganism.

Also provided herein is a culture comprising a recombinant photosynthetic microorganism in a suitable culture medium, in which the recombinant photosynthetic microorganism includes a non-native gene that encodes a dehydrogenase and a non-native gene encoding a polypeptide that participates in the production of a lipid, in which the culture produces a greater amount of the lipid than is produced by an identical culture of a microorganism identical in all respects except that it lacks the non-native gene encoding the dehydrogenase. Additionally or alternatively, the culture of the microorganism that includes the non-native dehydrogenase gene can reach a higher optical density after three, four, five, or six days of culture than the culture density reached by an identical culture of a microorganism identical in all respects except that it lacks the non-native gene encoding the dehydrogenase. The culture can be a photoautotrophic culture, for example, where the culture medium contains inorganic carbon as substantially the sole carbon source. The culture can produce at least 10% more, at least 25% more, at least 50% more, at least 75% more, at least 100%, at least 200% more, at least 300% more, at least 400%, at least 500% more, at least 700% more, or at least 800% more of a fatty acid, fatty acid derivative, or triglyceride compared to culture identical in all respects except that it comprises a recombinant microorganism lacking the first non-native gene.

The recombinant microorganism used in any of the methods herein can include a non-native gene encoding any dehydrogenase as disclosed herein, for example, the dehydrogenase can be an aldehyde dehydrogenase, a D-2-hydroxyacid dehydrogenase, a non-phosphorylating glyceraldehyde-3-phosphate dehydrogenase, a glucose-6-phosphate dehydrogenase, a 6-phosphogluconate dehydrogenase, an isocitrate dehydrogenase, or a malic enzyme. For example the dehydrogenase can be an aldehyde dehydrogenase, and in some examples can have at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:4, SEQ ID NO:6, or SEQ ID NO:7, or an active fragment thereof. Alternatively or in addition, the microorganism can include a methylmalonate semialdehyde dehydrogenase, and in some examples can be a methylmalonate semialdehyde dehydrogenase having at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:18 or SEQ ID NO:19, or an active fragment thereof. Alternatively or in addition, the microorganism can include a non-native gene encoding a D-2-hydroxyacid dehydrogenase, and in some examples can be a D-2-hydroxyacid dehydrogenase that has at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:2, SEQ ID NO:29, SEQ ID NO:15 or SEQ ID NO:16, or an active fragment thereof. Alternatively or in addition, the microorganism can include a non-native gene encoding a 6-phosphogluconate dehydrogenase. The 6-phosphogluconate in some examples has at least 50%, at least 55%, at least 60%, at least 65%, at least 70%, at least 75%, at least 80%, at least 85%, at least 90%, at least 95%, or at least 99% sequence identity to the amino acid sequence of SEQ ID NO:10, SEQ ID NO:11, or SEQ ID NO:13, or an active fragment thereof.

The methods can further include isolating at least on lipid from the culture. Lipids can be isolated from cells, media, or whole culture. Also provided herein is a lipid produced by any of the methods or recombinant microorganisms provided herein. The lipid can be any or any combination of a fatty acid, fatty aldehyde, fatty alcohol, fatty acid ester, wax ester, alkane, alkene, phospholipid, galactolipid, or triglyceride. The lipid can comprise at least one acyl chain containing between 8 and 24 carbon atoms, such as between 12 and 24 carbon atoms, for example, between 12 and 18 carbon atoms.

In some aspects, the invention relates to a recombinant photosynthetic microorganism comprising a first recombinant nucleic acid molecule comprising a first nucleotide sequence at least 50% identical to SEQ ID NO:3, SEQ ID NO:9, SEQ ID NO:1, SEQ ID NO:12, SEQ ID NO:14, or SEQ ID NO:17, where the nucleic acid molecule encodes a dehydrogenase. The recombinant photosynthetic microorganism can be engineered for the production of a fatty acid product, and can include at least a second recombinant nucleic acid molecule or nucleotide sequence that encodes a polypeptide that participates in the synthesis of a lipid. For example, the photosynthetic microorganism can include a recombinant nucleotide sequence encoding a polypeptide that participates in the synthesis of a free fatty acid, fatty acid derivative, or triglyceride that is not naturally produced by the photosynthetic microorganism, which can be, for example, a cyanobacterium. For example, the photosynthetic microorganism can include a recombinant nucleotide sequence encoding an acyl-ACP thioesterase and can produce a free fatty acid or a fatty acid derivative. In illustrative examples, the acyl-ACP thioesterase can be a higher plant acyl-ACP thioesterase or a variant thereof, such as, for example, the acyl-ACP thioesterase of SEQ ID NO:21.

The invention provides, in additional examples, a recombinant microorganism comprising an non-native first nucleic acid molecule comprising a nucleotide sequence encoding an aldehyde dehydrogenase or a D-2-hydroxyacid dehydrogenase, wherein the photosynthetic microorganism produces more of a fatty acid, fatty acid derivative, or lipid than is made by an otherwise identical microorganism that lacks the exogenous first nucleic acid molecule. In some embodiments, the organism further expresses at least one second non-native nucleic acid molecule encoding an enzyme selected from the group consisting of non-native acyl-ACP thioesterase, acyl-CoA thioesterase, hydroxybenzoyl thioesterase, acyl-ACP reductase, acyl-ACP reductase, wax synthase, decarbonylase, decarboxylase, acetyl-CoA carboxylase, malonyl CoA: ACP transacylase, beta-ketoacyl-ACP synthase, glycerolphosphate acyltransferase (GPAT), lysophosphatidic acid acyltransferase (LPAAT), phosphatidic acid phosphatase (PAP), or diacylglycerol O-acyltransferase (DGAT). Additionally, the microorganism may produce a fatty acid, fatty acid derivative, or glycerolipid that is not made by the microorganism in the absence of the second non-native nucleic acid molecule. The recombinant microorganism may be a photosynthetic microorganism, and may produce more of a fatty acid, fatty acid derivative, or glycerolipid than is made by an otherwise identical microorganism that lacks the first nucleic acid under photoautotrophic conditions. In some aspects, the invention relates to a method of producing a fatty acid product comprising culturing a recombinant photosynthetic microorganism of the invention that includes a first non-native gene encoding an aldehyde dehydrogenase or a D-2-hydroxyacid dehydrogenase and includes a second non-native gene encoding a polypeptide that participates in fatty acid, fatty acid derivative, or lipid biosynthesis for a sufficient amount of time to produce a fatty acid product. The fatty acid product can be a product not naturally produced by the photosynthetic microorganism.

Also provided is a recombinant photosynthetic microorganism comprising an homologous phosphogluconate dehydrogenase gene that is under the control of a heterologus promoter, i.e., a promoter that does not normally regulate the phosphogluconate dehydrogenase gene. For example, the phosphogluconate dehydrogenase gene can be operably linked to a heterologous, and preferably regulatable, promoter, and can be integrated into a non-native locus within the genome of the recombinant microorganism. Alternatively, a heterologous promoter can be inserted into the host genome to become operably linked to an endogenous phosphogluconate dehydrogenase gene, such that the endogenous phosphogluconate dehydrogenase can be overexpressed in the host microorganism. In some embodiments, the cell further expresses a second nucleic acid comprising a second nucleotide sequence encoding polypeptide that participates in the production of a lipid (e.g., a fatty acid product) in which the expression of phosphogluconate dehydrogenase gene increases the propagation and/or proliferation rate of the microorganism relative to an otherwise identical microorganism that does not include a recombinant phosphogluconate dehydrogenase gene.

In some embodiments, the photosynthetic microorganism is a cyanobacterium. In some embodiments, the cyanobacterium is selected from a group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.*

The invention also provides a method of producing free fatty acids, fatty acid derivatives, or lipids by the photosynthetic microorganism. The method can comprise culturing a photosynthetic microorganism described herein under conditions in which the first non-native nucleic acid molecule and the second nucleic acid molecule is expressed to produce at least one fatty acid or fatty acid derivative. Optionally, the photosynthetic microorganism is cultured phototrophically.

The expression of a non-native gene encoding a dehydrogenase and the expression of gene encoding a polypeptide for lipid biosynthesis in a recombinant microorganism can result in increased production of a fatty acid product, by a culture of the dehydrogenase-overexpressing microorganism relative to the production of a fatty acid product by a culture of a control microorganism cultured identically, and in which the control microorganism is substantially identical to the non-native dehydrogenase gene-expressing microorganism except that the control microorganism lacks the non-native dehydrogenase gene. In some embodiments, the amount of a free fatty acid, fatty acid derivative, or glycerolipid produced by a culture of a microorganism expressing the non-native dehydrogenase gene and a non-native lipid biosynthesis gene is at least 1%, at least 5%, at least 8%, at least 10%, at least 15%, at least 20%, at least 30%, at least 40%, at least 50%, at least 60%, at least 70%, at least 80%, at least 90%, at least 100%, at least 150%, or at least 200% more than the free fatty acid, fatty acid derivative, or glycerolipid produced by a culture of the control microorganism lacking the non-native dehydrogenase gene. The microorganism can be a photosynthetic microorganism.

Additionally or alternatively, the expression of a non-native gene encoding a dehydrogenase and the expression of gene encoding a polypeptide for lipid biosynthesis in a recombinant microorganism can increase the intracellular ratio of NADPH to $NADP^+$ relative to the ratio of NADPH to $NADP^+$ in an otherwise identical microorganism that lacks the non-native dehydrogenase gene. For example, the NADPH to $NADP^+$ ratio in cells expressing the non-native dehydrogenase gene and non-native lipid biosynthesis gene can be at least 1%, at least 5%, at least 8%, at least 10%, at least 15%, at least 20%, at least 30%, at least 40%, at least 50%, at least 60%, at least 70%, at least 80%, at least 90%, at least 100%, at least 150%, or at least 200% higher than the NADPH to $NADP^+$ ratio of an otherwise identical control microorganism lacking the non-native dehydrogenase gene during a culture period in which lipid is being produced. The microorganism can be a photosynthetic microorganism.

Further additionally or alternatively, the expression of a non-native gene encoding a dehydrogenase and the expression of gene encoding a polypeptide for lipid biosynthesis in a recombinant microorganism can increase the propagation rate and/or the proliferation rate of the engineered microorganism relative to the propagation and/or proliferation rate of an otherwise identical microorganism that lacks the non-native dehydrogenase gene. For example, the propagation rate or the proliferation rate can be at least 1%, at least 5%, at least 8%, at least 10%, at least 15%, at least 20%, at least 30%, at least 40%, at least 50%, at least 60%, at least 70%, at least 80%, at least 90%, at least 100%, at least 150%, or at least 200% higher than the propagation rate and/or the proliferation rate of a control microorganism that expresses the non-native lipid biosynthesis gene but does not include the non-native gene encoding a dehydrogenase. For example, a culture of the engineered microorganism that includes a non-native gene encoding a dehydrogenase and a non-native gene encoding a polypeptide for lipid biosynthesis can achieve a higher cell density after three, four, five, six, or more days in culture that can be achieved by a culture of an otherwise identical microorganism that does not include the non-native gene encoding the dehydrogenase, where the culture is producing a lipid. The microorganism can be a photosynthetic microorganism.

The amount of the free fatty acids, fatty acid derivatives, or lipids produced by the photosynthetic microorganism according to the invention can be at least 290 mg, at least 330 mg, at least 370 mg, at least 400 mg, at least 500 mg, at least 600 mg per liter of culture. Additionally, the method of producing a fatty acid product can further comprise isolating at least one fatty product from the photosynthetic microorganism or from the growth media.

In a further aspect, the invention provides an isolated nucleic acid molecule comprising a nucleic acid sequence encoding a polypeptide sequence that includes an amino acid sequence at least 65% identical, at least 75% identical, at least 85% identical or at least 95% identical to SEQ ID NO:2 or SEQ ID NO:29 or an active fragment thereof. The encoded polypeptide can have dehydrogenase activity, for example, D-2-hydroxyacid dehydrogenase activity. The nucleic acid molecule can further comprise a promoter, which can be heterologous with respect to the dehydrogenase encoding sequence, and can be regulatable, for example, inducible. The nucleic acid molecule can be provided in a vector.

DETAILED DESCRIPTION OF THE INVENTION

Figure 1:
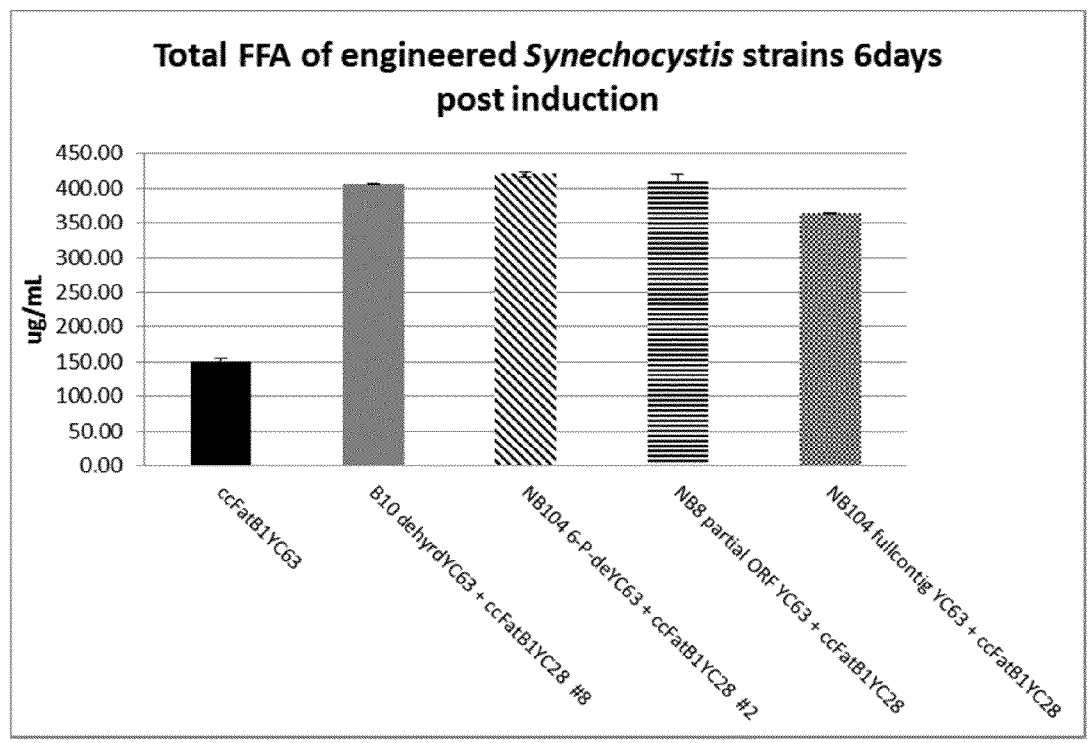
FIG. 1 depicts the total free fatty acids produced by engineered *Synechocystis* strains. *Synechocystis* strains expressing the B10 ORF ("dehydrd"; SEQ ID NO:1), the NB8 partial ORF fragment (SEQ ID NO:5), the NB104 ORF ("6-P-de"; SEQ ID NO:9), and NB104 ORF full contig fragment (SEQ ID NO:8), along with Cc1FatB1 acyl-ACP thioesterase gene (SEQ ID NO:20), produced higher levels of free fatty acids as compared to the control strain that contained the CclFatB 1 gene alone.

Photosynthetic organisms synthesize fatty acids for the production of membrane and storage lipids using fixed carbon from $CO_2$, as well as ATP and NADPH that are also generated from photosynthesis. NADPH can also be generated by the activity of dehydrogenases. The term "dehydrogenase" is used herein to refer to an enzyme that catalyzes the oxidation of a substrate by transferring one or more hydrides (H—) to an acceptor such as NAD+ or NADP+. The invention provides recombinant microorganisms that express at least one non-native gene encoding a dehydrogenase and produce one or more lipids, such as, for example, one or more fatty acids, one or more fatty acid derivatives, and/or one or more glycerolipids (e.g., one or more triglycerides). The recombinant microorganisms in some aspects demonstrate better proliferation rates while producing a lipid than comparable microorganisms that do not express a non-native gene encoding a dehydrogenase, and furthermore cultures of the recombinant microorganisms that express a non-native dehydrogenase gene can produce more lipid than is produced by control cultures of microorganisms that are identical in all respects to the dehydrogenase gene-expressing microorganisms, with the exception that the control microorganisms do not express a non-native dehydrogenase gene. The recombinant microorganisms may be recombinant photosynthetic microorganisms. Also provided are methods for producing a lipid by providing a culture of a microorganism that includes at least one non-native gene encoding a dehydrogenase, in which the culture produces more of the lipid than a culture identical in all respects except that the microorganism does not include a non-native gene encoding a dehydrogenase. The microorganism can be a photosynthetic microorganism and in some examples can be cultured photoautotrophically. The microorganism can additionally include one or more non-native genes encoding a polypeptide that participates in the synthesis of a lipid.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, or insertional mutation) or having decreased expression due to alteration of gene regulatory sequences.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, and gene replacement, promoter replacement, deletion, or insertion, as well as introduction of transgenes or synthetic genes into the organism. Recombinant or genetically engineered organisms can also be organisms into which constructs for gene "knock down" have been introduced. Such constructs include, but are not limited to, RNAi, microRNA, shRNA, siRNA, antisense, and ribozyme constructs. Also included are organisms whose genomes have been altered by the activity of meganucleases or zinc finger nucleases. An exogenous or recombinant nucleic acid molecule can be integrated into the recombinant/genetically engineered organism's genome or in other instances are not integrated into the recombinant/genetically engineered organism's genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. Non-limiting examples of promoters include, for example, the T7 promoter, the cytomegalovirus (CMV) promoter, the SV40 promoter, and the RSV promoter. Examples of inducible promoters include the lac promoter, the pBAD (araA) promoter, the Tet promoter (U.S. Pat. Nos. 5,464,758 and 5,814,618), and the Ecdysone promoter (No et al., *Proc. Natl. Acad. Sci.* (1996) 93 (8): 3346-3351).

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, polyA addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

This application discloses and refers to nucleic acids and polypeptides by identifiers used in long-established and extensively referenced databases maintained by the National Center for Biotechnology Information (NCBI). Accession numbers, commonly provided herein in parenthesis after a gene or species name, are unique identifiers for a sequence record publicly available at the National Center for Biotechnology Information website (ncbi.nlm.nih.gov) maintained by the United States National Institutes of Health. The "Gen-Info Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 65%, 70%, 75%, 80%, or 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

The term "secreted" includes movement of polypeptides or fatty acid products produced by the recombinant microorganisms or methods of the invention to the periplasmic space or extracellular milieu. "Increased secretion" includes secretion in excess of the naturally-occurring amount of secretion, e.g., that is at least 1%, 2%, 3%, 4%, 5%, 6%, 7%, 8%, 9%, or 10%, or at least 20%, 30%, 40%, 50%, 60%, 70%, 80%, 90%, 100%, 200%, 300%, 400%, 500%, 600%, 700%, 800%, 900%, 1000%, or more, as compared to the naturally-occurring level of secretion.

Included herein are aspects of engineering a microorganism in which the "insertion," e.g., the addition, integration, incorporation, or introduction of certain nucleic acid molecules or particular polynucleotide sequences within microorganisms or host cells in order to affect the expression of a gene in the microorganism. For example, a microorganism of interest may be engineered by site directed homologous recombination to insert a particular gene of interest with or without an expression control sequence such as a promoter, into a particular genomic locus, or to insert a promoter into a genetic locus of the host microorganism to affect the expression of a particular gene or set of genes at the locus.

Additional aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

The term "Pfam" refers to a large collection of protein domains and protein families maintained by the Pfam Consortium and available at several sponsored world wide web sites, including: pfam.sanger.ac.uk/(Welcome Trust, Sanger Institute); pfam.sbc.su.se/(Stockholm Bioinformatics Center); pfam.janelia.org/(Janelia Farm, Howard Hughes Medical Institute); pfam.jouy.inra.fr/(Institut national de la Recherche Agronomique); and pfam.ccbb.re.kr. The latest release of Pfam is Pfam 26.0 (November 2011) based on the UniProt protein database release 15.6, a composite of Swiss-Prot release 57.6 and TrEMBL release 40.6. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research Database Issue* 34, D247-251; Finn (2010) *Nucleic Acids Research Database Issue* 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

As used herein, a "long chain length" fatty acid or acyl-ACP is a fatty acid or acyl-ACP having a chain length of greater than 14 carbons and a "medium chain length" fatty acid or acyl-ACP is a fatty acid or acyl-ACP having a chain length of from 8-14 carbons.

"Substrate preference" refers to the substrate or substrates an enzyme is most active on. For example, different acyl-ACP thioesterases may have different degrees of chain length specificity, sometimes referred to as the enzyme's "preference" for cleaving a particular length of fatty acid from ACP, and thioesterases are typically most active in cleaving a particular chain length fatty acid while having lesser activity in cleaving one or more other chain length fatty acids.

As used herein, the term "fatty acid product" includes free fatty acids; mono-, di- or triglycerides; fatty aldehydes; fatty alcohols; fatty acid esters (including, but not limited to, wax esters); and hydrocarbons (including, but not limited to, alkanes and alkenes).

"Propagation rate" or "replicative rate", as used interchangeably herein, is measured commonly in microorganisms by measuring the doubling time of a given culture. Methods for measuring the rate of propagation of microorganisms are well known in the art. For example, optical density (OD) measurements may be taken over periods of time to measure the rate of propagation (increase in the number of cells) or proliferation (increase in cell number as well as increases in cell size and/or cellular contents). Alternatively, the concentration of microorganisms in suspension can be determined by using a hemocytometer or similar apparatus to determine the concentration of cells in a given volume of a culture. By taking multiple data points at various times, the propagation or replicative rate of cells in a culture can be assessed. An increase in culture density over a period of time (for example, as measured by OD) is indicative of propagation and/or proliferation.

Metabolic Pathways for Producing Fatty Acid Products

The lipids produced by the recombinant microorganisms disclosed herein can be fatty acid products, including free fatty acids and products that are derived from fatty acids and/or incorporate the acyl chains of fatty acids produced by the cell, including, without limitation: mono-, di- or triglycerides; fatty aldehydes; fatty alcohols; fatty acid esters (including, but not limited to, wax esters); and hydrocarbons (including, but not limited to, alkanes and alkenes). The fatty acid biosynthesis pathway, highly conserved in prokaryotes and in the chloroplasts of eukaryotic algae and higher plants, starts from the central metabolite acetyl-CoA. Fatty acid biosynthesis is initiated by the conversion of acetyl-CoA to malonyl-CoA, catalyzed by acetyl-CoA carboxylase (ACCase). Malonyl-CoA is then converted to malonyl-ACP, catalyzed by malonyl-CoA-ACP transacylase (FabD in *E. coli*). Malonyl-ACP is then converted to acyl-ACP, catalyzed by the enzyme complex fatty acid synthase (FAS). The fatty acid synthase complex initiates the elongation cycle by first condensing malonyl-ACP with acetyl-ACP, catalyzed by a beta-ketoacyl-ACP synthase III (e.g., FabH of *E. coli*). The β-ketoacyl-ACP (3-ketoacyl-ACP) formed by the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to form the 2 carbon-elongated acyl-ACP product. Subsequent cycles are initiated by a beta-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is transferred to another molecule (e.g. glycerol 3-phosphate) by a transacylase or cleaved from ACP by a thioesterase, such as FatA or FatB in chloroplasts, to form free fatty acids.

Unlike plant chloroplasts, cyanobacteria do not produce free fatty acids, and unlike *E. coli* and other heterotrophic bacteria, cyanobacteria do not produce acyl-CoA (Kaczmarzyk and Fulda (2010) *Plant Physiol.* 152: 1598-1610). Following fatty acid elongation in which the acyl chain is covalently bound to acyl carrier protein, acyl transferases of cyanobacteria transfer the acyl chain to a glycerol backbone to produce membrane lipids.

To produce free fatty acids in a microorganism, such as, but not limited to, a cyanobacterium, an exogenous or recombinant thioesterase gene, such as but not limited to a gene encoding an acyl-ACP thioesterase, a gene encoding an acyl-CoA thioesterase, or a gene encoding a hydroxybenzoyl thioesterase, can be expressed in the microorganism. To produce fatty acid derivatives such as fatty alcohols, fatty aldehydes, wax esters, alkanes, or alkenes in microorganisms, one or more enzymes to convert acyl-thioester intermediates (e.g., acyl-CoA or acyl-ACP) to the desired end product (e.g., an alcohol, aldehyde, alkane, alkene, or wax ester) may be introduced into the host cell, optionally in combination with an exogenous or recombinant gene encoding a thioesterase and, optionally, an exogenous gene encoding an acyl-CoA synthetase. For example, if fatty aldehydes and/or alkanes are the desired end product, a gene encoding an aldehyde-forming fatty aldehyde reductase (e.g., aldehyde-forming acyl-CoA reductase, 1.2.1.42 or 1.2.1.50; see also U.S. Pat. No. 6,143, 538) may be introduced to reduce acyl-CoA to fatty aldehydes; additionally or alternatively, an aldehyde-forming acyl-ACP reductase (e.g., as disclosed in WO 2009/140696 or WO 2011/066137) or a carboxylic acid reductase gene (see, e.g., WO 2010/135624 and WO 2010/042664) may be introduced to reduce free fatty acids to fatty aldehydes. Alternatively or in addition, a gene encoding a fatty alcohol oxidase (e.g., 1.1.3.20) or a fatty alcohol dehydrogenase (e.g., 1.1.1.164) may be introduced to convert fatty alcohols to fatty aldehydes. Fatty aldehydes may optionally be processed further to alkanes with the introduction of a gene encoding a fatty aldehyde decarbonylase (e.g., 4.1.99.5). If fatty alcohols, alkenes and/or wax esters are the desired end product, a gene encoding an alcohol-forming fatty acyl reductase (e.g., an alcohol-forming acyl-CoA reductase, 1.2.1.50) may be introduced into the host cell. Further, a fatty aldehyde reductase gene may be introduced to reduce fatty aldehydes to fatty alcohols. Fatty alcohols may be processed further to alkenes with the introduction of one or more genes encoding a fatty alcohol dehydratase. Fatty acid esters, including wax esters, may be formed by introducing genes encoding polypeptides that catalyze condensation of an alcohol with a fatty acyl thioester, such as acyltransferases and wax synthases.

In some examples, the conversion of acyl-ACP to fatty alcohol may occur via synthesis of a fatty aldehyde, wherein an acyl reductase (e.g., an aldehyde-forming acyl-CoA reductase or aldehyde-forming acyl-ACP reductase) expressed in the host cell first reduces acyl-ACP to a fatty aldehyde. For example, in certain embodiments, the host cell can be engineered to overexpress an endogenous fatty aldehyde-forming reductase (e.g., by inserting promoter and/or enhancer transcriptional control elements near the fatty aldehyde-forming reductase gene). In other embodiments, the host cell may be engineered to express an exogenous fatty aldehyde-forming reductase. The host cell may further include an exogenous gene that encodes a fatty aldehyde reductase or alcohol dehydrogenase that reduces the fatty aldehyde to a fatty alcohol.

Wax esters may be formed by introducing a gene encoding a wax ester synthase to catalyze condensation of a fatty alcohol with a fatty acyl thioester. A wax ester synthase can be, for example, an enzyme of the class EC 2.3.1.26 (long chain alcohol O-fatty acyltransferase), EC 2.3.1.20 (diacylglycerol acyltransferase), EC 2.3.1.51 (acyltransferase), or 2.3.1.75 (wax ester synthase/acyl-CoA diacylglycerol acyltransferase).

For production of glycerolipids, such as, for example, monoacylglycerides, diacylglycerides, and triacylglycerides ("TAGs"), a recombinant microorganism as disclosed herein that includes a non-native gene encoding a dehydrogenase can further include a non-native gene encoding an enzyme that participates in the production of glycerolipids, including, but not limited to, a glycerolphosphate acyltransferase (GPAT), a lysophosphatidic acid acyltransferase (dehydrogenase), a phosphatidic acid phosphatase (PAP), or a diacylglycerol O-acyltransferase (DGAT).

Dehydrogenases

The present invention provides a recombinant microorganism that includes a non-native gene encoding a dehydrogenase and produces at least one fatty acid product. For example, a recombinant microorganism as disclosed herein can be transformed with an isolated nucleic acid molecule comprising a nucleic acid sequence that encodes a dehydrogenase. Alternatively or in addition, the recombinant microorganism can include an endogenous nucleic acid sequence encoding a dehydrogenase, in which at least one regulatory sequence has been inserted into the genome of the microorganism to regulate expression of the endogenous dehydrogenase gene. Additionally, the microorganism can be transformed with one or more exogenous genes, and/or can be engineered to overexpress one or more endogenous genes, that participate in the production of a lipid, such as a fatty acid product.

Dehydrogenases that can be expressed in the recombinant microorganisms disclosed herein include, without limitation, aldehyde dehydrogenases (including aldehyde dehydrogenases (EC 1.2.1.3), succinate-semialdehyde dehydrogenases (EC 1.2.1.16), methylmalonate semialdehyde dehydrogenases (EC 1.2.1.27), lactaldehyde dehydrogenases (EC 1.2.1.22), benzaldehyde dehydrogenases (EC 1.2.1.28), non-phosphorylating glyceraldehyde-3-phosphate dehydrogenases (EC 1.2.1.9), NADP-dependent (phosphorylating) glyceraldehyde-3-phosphate dehydrogenases (EC 1.2.1.13), delta-1-pyrroline-5-carboxylate dehydrogenases (EC 1.5.1.12), acetaldehyde dehydrogenases (EC: 1.5.1.10), and glutamate semialdehyde dehydrogenases (EC: 1.5.1.41)), 2-hydroxyacid dehydrogenases (e.g., isocitrate dehydrogenases, lactate dehydrogenases, malate dehydrogenases, succinate dehydrogenases, alpha ketoglutarate dehydrogenases), D-2-hydroxyacid dehydrogenases e.g., D-2-hydroxyisocaproate dehydrogenases, formate dehydrogenases, D-glycerate dehydrogenases, vancomycin-resistant protein H, D-2-phosphoglycerate dehydrogenases, and D-lactate dehydrogenases (1.1.1.28)), malic enzymes (1.1.1.40), glucose-6-phosphate dehydrogenases (1.1.1.49), 6-phosphogluconate dehydrogenases (1.1.1.43, 1.1.1.44), glutamate dehydrogenases, isocitrate dehydrogenases, and sorbitol dehydrogenases. In various examples, the dehydrogenase encoded by a non-native gene introduced into or overexpressed in a microorganism of the present invention is not an alcohol dehydrogenase. In further examples, a dehydrogenase encoded by a non-native gene introduced into or overexpressed in a microorganism of the present invention may not be a pyruvate dehydrogenase or a phosphorylating glyceraldehyde-3-phosphate dehydrogenase (EC 1.2.1.12). Assays for the activity of dehydrogenases are well known in the art (e.g., Wynn et al. (1997) Lipids 32: 605-610; Graupner et al. (2000) J. Bacteriol. 182: 3688-3692; Berrios-Rivera et al. (2002) Metabolic Engineering 4: 217-229; Shinoda et al. (2005) J. Biol. Chem. 280: 17068-17075; Domenech and Ferrer (2006) Biochim. Biophys. Acta 1760: 1667-1674; Lo and Chen (2010) Mol. Biotechnol 46: 157-167).

Of particular interest are dehydrogenases that generate NADPH, although dehydrogenases that produce NADH are also considered for use in the methods and microorganisms of the invention. For example, NADH may be converted to NADPH in cells via the activity of NADPH:NAD+ oxidoreductases (B-specific) sometimes referred to as NADPH-NAD+ transhydrogenases (see, e.g., US 2005/0196866) which may be native to the host cell, or a gene encoding an NADPH-NAD+ transhydrogenases may be introduced into the host microorganism.

Malic enzyme (EC 1.1.1.40), also known as malate dehydrogenase (oxaloacetate-decarboxylating) (NADP(+)) or NADP-malic enzyme, which catalyzes the irreversible decarboxylation of malate to pyruvate while reducing NADP+ to NADPH, is an example of a dehydrogenase that can be produced in a recombinant host cell by expression of a non-native gene. A non-native gene encoding malic enzyme can be derived from any organism, and can be heterologous or homologous with respect to the host microorganism. Nonlimiting examples of a malic enzyme that can be encoded by a non-native gene in a microorganism as disclosed herein include polypeptides that recruit to Pfam PF00390 (malic enzyme, N-terminal domain) with a bit score greater than the gathering cutoff of 19.2, and/or recruit to Pfam PF03949 (malic enzyme NAD binding domain) with a bit score higher than the gathering cutoff of 23.5. A crystal structure of a malic enzyme has been reported by Yang et al. (*Protein Sci.* 11: 332-341 (2002)). Nonlimiting examples of malic enzymes include those from *Mucor circinelloides* (ABM45933, AAO26053.1), *Thalassiosira pseudonana* (XP_002290550), *Phaeodactylum tricornutum* (XP_002177890), *Ostreococcus lucimarinus* (XP_001420849), *Ricinus communis* (XP_002526507), *Oryza sativa* (NP_001064998), *Arabidopsis thaliana* (AEE36294), *Chlorella variabilis* (EFN53662), *Homo sapiens* (NP_002386), *Chlamydomonas reinhardtii* (XP_001696240), *Synechocystis* sp. PCC 6803 (BAA16663), *Microcystis aeruginosa* (YP_001655800), and '*Nostoc azollae*' (YP_003720944). Without limitation, malic enzymes encoded by a non-native gene in a microorganism as provided herein can be polypeptides with malic enzyme activity having at least 80%, at least 85%, at least 90%, or at least 95% amino acid sequence identity to these malic enzymes or others as listed in sequence databases, conservative variants thereof, and N-terminally and/or C-terminally truncated or modified variants thereof. For example, a recombinant microorganism as provided herein can include a non-native gene encoding a polypeptide that includes an amino acid sequence having at least 95% identity to a polypeptide identified as a malic enzyme, or to an active fragment thereof.

Glucose-6-phosphate dehydrogenase (EC 1.1.1.49) is an NADPH-generating enzyme of the pentose phosphate pathway that can be produced by expression of a non-native gene in a microorganism as provided herein. The gene encoding glucose-6-phosphate can be derived from a plant, animal, or microbe, including a fungus, heterokont, alga, bacterium, or cyanobacterium. For example, the dehydrogenase can be a polypeptide that recruits to Pfam PF00479 "Glucose-6-phosphate dehydrogenase, NAD binding domain" with a bit score greater than the gathering cut-off of 21.7, and/or can recruit to Pfam, PF02781 "Glucose-6-phosphate dehydrogenase, C-terminal domain" with a bit score greater than the gathering cut-off of 19.5. Nonlimiting examples of glucose-6-phosphate dehydrogenases that can be expressed by a microorganism as provided herein include the glucose 6-phosphate dehydrogenase of *Synechocystis* sp. PCC 6803 (BAA17451), *Synechococcus* sp. BL107 (ZP_01468297), *Prochlorococcus marinus* str. AS9601 (YP_001009571), *Lyngbya* sp. PCC 8106 (ZP_01620414), *Thalassiosira pseudonana* CCMP1335 (EED92550), *Micromonas* sp. RCC299 (XP_002508505); *Ostreococcus tauri* (XP_003079573), *Glycine max* (XP_003533032), *Vitis vinifera* (XP_002266930), *Oryza sativa* Japonica Group (AAQ02671), *Mus musculus* (NP_000393; NP_032088), and *Homo sapiens* (NP_000393). Without limitation, glucose-6-phosphate dehydrogenases that can be expressed from non-native genes in the engineered microorganisms provided herein can be polypeptides with glucose-6-phosphate dehydrogenase activity having at least 80%, at least 85%, at least 90%, or at least 95% amino acid sequence identity to these glucose-6-phosphate dehydrogenases or others as listed in sequence databases, including conservative variants thereof, and can be N-terminally and/or C-terminally truncated or modified variants thereof. For example, a recombinant microorganism as provided herein can include a non-native gene encoding a glucose-6-phosphate dehydrogenase having at least 95% identity to a polypeptide identified as a glucose-6-phosphate dehydrogenase, or to an active fragment thereof.

Another NADPH-producing enzyme of the pentose phosphate pathway is 6-phosphogluconate dehydrogenase. "Phosphogluconate dehydrogenase" or "6-phosphogluconate dehydrogenase" (EC 1.1.1.43 or EC 1.1.1.44) as used herein, refers to an enzyme that catalyzes the decarboxylating reduction of 6-phosphogluconate into ribulose-5-phosphate in the presence of $NADP^+$. As a result of the catalysis, the NADP is reduced to NADPH. The invention includes recombinant microorganisms that include a non-native gene encoding a 6-phosphogluconate dehydrogenase, and preferably, at least one additional gene encoding a protein for the production of a lipid. A 6-phosphogluconate dehydrogenase expressed by a recombinant microorganism of the invention can be from a plant, animal, or microbe, including a fungus, heterokont, alga, bacterium, or cyanobacterium. As disclosed herein, expression of non-native genes encoding 6-phosphogluconate dehydrogenase can enhance fatty acid biosynthesis by the host microorganism. Phosphogluconate dehydrogenases that may be useful in the microorganisms and methods disclosed herein include 6-phosphogluconate dehydrogenases that recruit to Pfam PF03446 "NAD binding domain of 6-phosphogluconate dehydrogenase" (gathering cut-off 21.0) and, preferably, recruit to Pfam PF00393 "6-phosphogluconate dehydrogenase, C-terminal domain" (gathering cut-off 20.4). Crystal structures of 6-phosphogluconate dehydrogenases have been published (e.g., Adams et al. (1994) *Structure* 2:651-658). Examples of phosphogluconate dehydrogenases that may be encoded by a non-native gene in an engineered microorganism as provided herein include but are not limited to a 6-phosphogluconate dehydrogenase of *Synechocystis* sp. PCC 6803 (BAA10105), *Cyanothece* sp. PCC 7822 (ADN14972), *Nostoc azollae* 0708 (ADI63566), *Synechococcus* sp. PCC 7002 (YP_001733490), *Arabidopsis thaliana* (AED94705), *Glycine max* (BAA22812), *Pinus sylvestris* (ADP03060), *Bombyx mori* (gb DAA21283), *Bos taurus* (DAA21283), *Saccharomyces cerevisiae* (AAA53637), *Aspergillus terreus* NIH2624 (EAU33612), *Streptococcus pneumoniae* SP-BS293 (EFL69841), *Escherichia coli* (AAG35237), and variants thereof. Additionally or alternatively, a microorganism as disclosed herein can include a non-native gene encoding a 6-phosphogluconate dehydrogenase that includes an amino acid sequence having at least 50%, at least 55%, at least 60%, at least 65%, at least 70%, at least 75%, at least 80%, at least 85%, at least 90%, or at least 95% amino acid sequence identity to SEQ ID NO:10, SEQ ID NO:11, SEQ ID NO:13, or an active fragment thereof. Nonlimiting examples of 6-phosphogluconate dehydrogenases having amino acid sequences with homology to the polypeptide of SEQ ID NO:10 include the 6-phosphogluconate dehydrogenase of *Carnobacterium* sp. AT7 (ZP_02185894), the 6-phosphogluconate dehydrogenase of *Anaerococcus vaginalis* ATCC 51170 (ZP_05473398), the 6-phosphogluconate dehydrogenase of *Enterococcus casseliflavus* (ZP_05646912), and the 6-phosphogluconate dehydrogenase-like protein of *Clostridium beijerinckii* NCIMB 8052 (YP_001309315). Nonlimiting examples of 6-phosphogluconate dehydrogenases having amino acid sequences with homology to the polypeptide of SEQ ID NO:13 include the 6-phosphogluconate dehydrogenase of *Cyanothece* sp. PCC 8801(YP_002372435, *Microcystis aeruginosa* NIES-843 (YP_001656536), *Synechococcus* sp. PCC 7002 (YP_001733490), *Arthrospira platensis* str. Paraca (ZP_06383632), *Nostoc* sp. PCC 7120 (NP_

489315), *Oscillatoria* sp. PCC 6506 (ZP_07110168), and *Thermosynechococcus elongatus* BP-1 (NP_681366). Without limitation, 6-phosphogluconate dehydrogenases that can be expressed from non-native genes in the engineered microorganisms provided herein can be polypeptides with phosphogluconate dehydrogenase activity having at least 80%, at least 85%, at least 90%, or at least 95% amino acid sequence identity to the above-cited phosphogluconate dehydrogenases or others as listed in publications or sequence databases, including conservative variants of identified phosphogluconate dehydrogenases, and including N-terminally and/or C-terminally truncated or modified variants. In some instances, a nucleic acid molecule useful in the invention can encode a 6-phosphogluconate dehydrogenase that has at least 95% sequence identity to a 6-phosphogluconate dehydrogenase as provided herein or identified in a sequence database or an N-terminally and/or C-terminally truncated variant thereof (for example, a 6-phosphogluconate dehydrogenase that lacks the chloroplast transit peptide of the reference enzyme, or alternatively has an added chloroplast transit peptide not present in the reference enzyme), a conservative variant thereof, or modified variants thereof.

As demonstrated in the examples, a non-native gene encoding an aldehyde dehydrogenase can also be expressed in a recombinant microorganism of the invention to improve lipid production by the recombinant microorganism. "Aldehyde dehydrogenase" refers herein to an enzyme that catalyzes the oxidation of aldehydes to carboxylic acids. Aldehyde dehydrogenases useful in the microorganisms and methods disclosed herein include aldehyde dehydrogenases that recruit to Pfam PF00171 "Aldehyde dehydrogenase family" (gathering cut-off 23.0), and include aldehyde dehydrogenases of EC 1.2.1.3, succinate-semialdehyde dehydrogenases (EC 1.2.1.16), methylmalonate semialdehyde dehydrogenases (EC 1.2.1.27), lactaldehyde dehydrogenases (EC 1.2.1.22), benzaldehyde dehydrogenases (EC 1.2.1.28), non-phosphorylating glyceraldehyde-3-phosphate dehydrogenases (EC 1.2.1.9), NADP-dependent glyceraldehyde-3-phosphate dehydrogenases (EC 1.2.1.13), delta-1-pyrroline-5-carboxylate dehydrogenases (EC 1.5.1.12), acetaldehyde dehydrogenases (EC: 1.5.1.10), and glutamate semialdehyde dehydrogenases (EC: 1.5.1.41). The aldehyde substrate can be, for example, acetaldehyde, propionaldehyde, butyraldehyde, valeraldehyde, isovaleraldehyde, benzaldehyde, glyceraldehyde-3-phosphate, or another aldehyde. An example of a crystal structure of an aldehyde dehydrogenase is provided in Di Costanzo et al. (2007) *J. Mol. Biol.* 366: 481-493. Aldehyde dehydrogenases useful in the microorganisms and methods of the invention may be aldehyde dehydrogenases that are able to use NADP+ as a cofactor (see, for example, Lo and Chen (2010) *Mol Biotechnol* 46:157-167). Nonlimiting examples of aldehyde dehydrogenases include the aldehyde dehydrogenase of *Bacillus licheniformis* (YP_089937), *Bacillus stearothermophilus* SIC1 (YP_688823), *E. coli* (NP_287888), *Saccharomyces cerevisiae* (NP_015264), *Homo sapiens* (NP_000680), *Mus musculus* (AAB32754), and the NADP-dependent glyceraldehyde-3-phosphate dehydrogenases of *Streptococcus mutans* (Q59931), *Zea mays* (NP_001105589), and *Pisum sativum* (P81406). Additionally or alternatively, a microorganism as disclosed herein that includes a non-native gene encoding an aldehyde dehydrogenase can encode a polypeptide that includes an amino acid sequence having at least 50%, at least 55%, at least 60%, at least 65%, at least 70%, at least 75%, at least 80%, at least 85%, at least 90%, or at least 95% amino acid sequence identity to SEQ ID NO:4, SEQ ID NO:6, or SEQ ID NO:7, or to an active fragment thereof. Examples of aldehyde dehydrogenases having homology to amino acid sequences of SEQ ID NO:4, SEQ ID NO:6, and SEQ ID NO:7 include aldehyde dehydrogenases from *Bacillus* species, including, without limitation, the aldehyde dehydrogenases of *Bacillus thuringiensis* serovar *berliner* (ZP_041101108); *Bacillus thuringiensis* IBL 200 (ZP_04070879); *Bacillus thuringiensis* IBL 4222 (ZP_04064201); *Bacillus thuringiensis* servovar *kurstaki* (ZP_04113863), *Bacillus cereus* ATCC 10876 (ZP_04316482), *Bacillus thuringiensis* serovar *huazhongensis* (ZP_04083445), *Bacillus cereus* (ZP_03228808), *Bacillus cereus* 172560W (ZP_04305164), *Bacillus cytotoxicus* NVH 391-98 (YP_001374327); *Bacillus megaterium* WSH-002 (AEN89990); *Bacillus mycoides* Rock3-17 (ZP_04156127), *Bacillus cereus* AH621 (ZP_04293977), and *Bacillus thuringiensis* str. Al Hakam (YP_894009). Without limitation, an aldehyde dehydrogenase that can be expressed from a non-native gene in the engineered microorganisms provided herein can be a polypeptide with aldehyde dehydrogenase activity that includes an amino acid sequence having at least 85%, at least 90%, or at least 95% amino acid sequence identity to any of the above-cited aldehyde dehydrogenases or others listed in publications or sequence databases, or active fragments thereof, including conservative variants of identified aldehyde dehydrogenases, and including N-terminally and/or C-terminally truncated or modified variants. In some instances, a nucleic acid molecule useful in the invention can encode an aldehyde dehydrogenase that has at least 95% sequence identity to an aldehyde dehydrogenase as provided herein or identified in a sequence database or an N-terminally and/or C-terminally truncated variant thereof.

In some instances the aldehyde dehydrogenase encoded by a gene introduced into or overexpressed in the host microorganism may be a methylmalonate semialdehyde dehydrogenase (EC 1.2.1.27). A crystal structure of a methylmalonate semialdehyde dehydrogenase is found in Dubourg et al. (2004) *Acta Crystallogr D. Biol. Crystallogr.* 60: 1435-1437. Nonlimiting examples of methylmalonate semialdehyde dehydrogenases include the methylmalonate semialdehyde dehydrogenases of *Rattus norvegicus* (AAA41638); *Pseudomonas aeruginosa* (AAA25891); *Homo sapiens* (CAB76468); *Geobacillus thermoglucosidasius* C56-YS 93 (YP_004588333); *Hanseniella* sp. 'Han2' (ACY45298); *Medicago truncatula* (XP_003608372); *Arabidopsis thaliana* (AEC06286); *Acinetobacter baumannii* 6014059 (ZP_08442960); and *Rhodococcus erythropolis* PR4 (BAH34663). Alternatively or in addition, a microorganism as disclosed herein that includes a non-native gene encoding an aldehyde dehydrogenase can encode a methylmalonate semialdehyde dehydrogenase comprising an amino acid sequence having at least 50%, at least 55%, at least 60%, at least 65%, at least 70%, at least 75%, at least 80%, at least 85%, at least 90%, or at least 95% amino acid sequence identity to SEQ ID NO:18 or SEQ ID NO:19, or to an active fragment thereof. Nonlimiting examples of methylmalonate semialdehyde dehydrogenases having homology to SEQ ID NO:18 or SEQ ID NO:19 include the methylmalonate semialdehyde dehydrogenase of *Bacillus atrophaeus* 1942 (YP_003975426; ADP34495), *Bacillus licheniformis* ATCC 14580 (YP_081323; AAU25685), *Paenibacillus dendritiformis* C454 (ZP_09676636), *Paenibacillus terrae* HPL-003 (YP_005075546; AET59323), *Bacillus clausii* KSM-K$_{16}$ (YP_173925; BAD62964), *Listeria monocytogenes* FSL F2-208 (EFR85827), *Listeria marthii* FSL S4-120 (ZP_07869657; EFR88847), and *Alicyclobacillus acidocaldarius* LAA1 (ZP_03495181; EED06125). Without limitation, an aldehyde dehydrogenase encoded by a non-native gene in an engineered microorganism as provided herein can be a polypeptide with methylmalonate semialdehyde dehydrogenase activity having at least 80%, at least 85%, at least 90%, or at least 95% amino acid sequence identity to any of these methylmalonate semialdehyde dehydrogenase or others as listed in sequence databases, conservative variants thereof, and N-terminally and/or C-terminally truncated or modified variants thereof. For example, a nucleic acid molecule useful in the invention can encode a methylmalonate semialdehyde dehydrogenase that has at least 95% sequence identity to a polypeptide as cited herein, or to another aldehyde dehydrogenase identified in a publication or sequence databases, or to an active fragment thereof.

A microorganism as disclosed herein can alternatively or in addition include a non-native gene encoding an aldehyde dehydrogenases that is a non-phosphorylating glyceraldehyde-3-phosphate dehydrogenase (E.C. 1.2.1.9), also referred to as an NADP+-requiring glyceraldehyde-3-phosphate dehydrogenase (non-phosphorylating). A crystal structure of a non-phosphorylating glyceraldehyde-3-phosphate dehydrogenase is provided in Lorentzen et al. (2004) *J. Mol. Biol.* 341: 815-828. Nonlimiting examples of a non-phosphorylating glyceraldehyde-3-phosphate dehydrogenase that can be encoded by a recombinant nucleic acid molecule in a microorganism as provided herein include those derived from *Arabidopsis thaliana* (NP_180004), *Chlorella variabilis* (EFN50637), *Glycine max* (XP_003549550), *Brachypodium distachyon* (XP_003574540), *Sorghum bicolor* (XP_002444416), *Zea mays* (ACF84575), *Chlamydomonas reinhardtii* (XP_001753784), *Ostreococcus lucimarinus* (XP_001418445), *Bacillus cereus* (ZP_04196022.1), and *Selaginella moellendorffii* (XP_002981587.1). Without limitation, a non-phosphorylating glyceraldehyde-3-phosphate dehydrogenase encoded by a non-native gene in an engineered microorganism as provided herein can be polypeptides with non-phosphorylating glyceraldehyde-3-phosphate dehydrogenase activity having at least 80%, at least 85%, at least 90%, or at least 95% amino acid sequence identity to any of these non-phosphorylating glyceraldehyde-3-phosphate dehydrogenases or others as listed in sequence databases, including conservative variants thereof, and including N-terminally and/or C-terminally truncated or modified variants thereof. For example, a nucleic acid molecule useful in the invention can encode a non-phosphorylating glyceraldehyde-3-phosphate dehydrogenase that has at least 85% or at least 90% sequence identity to a polypeptide as provided herein or an N-terminally and/or C-terminally truncated or modified variant, or to another non-phosphorylating glyceraldehyde-3-phosphate dehydrogenase identified in sequence listings or databases or to an active fragment thereof. In some instances, a nucleic acid molecule useful in the invention can encode an aldehyde dehydrogenase that has at least 95% sequence identity to a polypeptide as provided herein or identified in a sequence listing or database.

Yet another type of dehydrogenase that can be produced by expression of a non-native gene in a recombinant microorganism as provided herein is a D-isomer specific 2-hydroxyacid dehydrogenase (a D-2-hydroxyacid dehydrogenase), such as, for example, a D-2-hydroxyisocaproate dehydrogenase, a formate dehydrogenase, a D-glycerate dehydrogenase, a vancomycin-resistant protein H, a D-2-photoglycerate dehydrogenase, or a D-lactate dehydrogenase. "D-2-hydroxyacid dehydrogenase" as used herein, refers to an enzyme that catalyzes the oxidation of an α-hydroxy carboxylic acid to an α-keto carboxylic acid, e.g. a lactate compound to a pyruvate compound. In the process, NAD(P)$^+$ is reduced to yield NAD(P)H. While many D-2-hydroxyacid dehydrogenases prefer NAD+ as a cofactor, others have been found to use NADP+ as a cofactor (Domenech and Ferrer (2006) *Biochim Biophys Acta* 1760: 1667-1674). An example of a crystal structure of a D-2-hydroxyacid dehydrogenases can be found in Dengler et al. (1997) *J. Mol. Biol.* 267: 640-660. D-2-hydroxyacid dehydrogenases useful in the microorganisms and methods disclosed herein include D-2-hydroxyacid dehydrogenases that recruit to Pfam PF02826 "D-2-hydroxyacid dehydrogenase family" (gathering cut-off 25.1). Nonlimiting examples of D-2-hydroxyacid dehydrogenases include the D-2-hydroxyacid dehydrogenases of Haloferax mediterranei (ABB30004), *Enterococcus faecalis* (AAB05626), *Haloarcula marismortui* ATCC 43049 (AAV47467), *Bacillus* sp. 2 A 57 CT2 (ZP_08008412), *Streptococcus pyogenes* MGAS2096 (ABF36015.1), *Lactobacillus plantarum* subsp. *plantarum* NC8 (EHS 81987.1), *Staphylococcus aureus* subsp. *aureus* 50385 (CAQ50990.1), *Rhizobium leguminosarum* bv. trifolii WSM2304 (ACI57766.1), *Nostoc punctiforme* ATCC 29133 (YP_001869125), *Micromonas* sp. RCC299 (ACO70365), *Phaeodactylum tricornutum* CCAP 1055/1 (XP_002183675), *Ostreococcus tauri* (XP_003081992), and *Aedes aegypti* (EAT43121), as well as the formate dehydrogenase of *Neurospora crassa* (CAC1825). Alternatively or in addition, a microorganism as disclosed herein that includes a non-native gene encoding a D-2-hydroxyacid dehydrogenase can include a non-native gene encoding a polypeptide that includes an amino acid sequence having at least 50%, at least 55%, at least 60%, at least 65%, at least 70%, at least 75%, at least 80%, at least 85%, at least 90%, or at least 95% amino acid sequence identity to SEQ ID NO:2, SEQ ID NO:29, SEQ ID NO:15, or SEQ ID NO:16, or to an active fragment thereof. For example, provided herein is a nucleic acid molecule comprising a nucleotide sequence that encodes a polypeptide having dehydrogenase activity that includes an amino acid sequence having at least at least 65%, at least 70%, at least 75%, at least 80%, at least 85%, at least 90%, or at least 95% amino acid sequence identity to SEQ ID NO:2 or SEQ ID NO:29, such as, for example, an amino acid sequence having at least 85%, at least 90%, or at least 95% amino acid sequence identity to SEQ ID NO:2 or SEQ ID NO:29. Alternatively, a nucleic acid molecule as provided herein can include a nucleotide sequence that encodes a polypeptide having dehydrogenase activity that includes an amino acid sequence having at least 80%, at least 85%, at least 90%, or at least 95% amino acid sequence identity to SEQ ID NO:15 or SEQ ID NO:16.

Nonlimiting examples of D-2-hydroxyacid dehydrogenases having homology to SEQ ID NO:2 or SEQ ID NO:29 include the D-2-hydroxyacid dehydrogenase of *Polymorphum gilvum* SL003B-26A1 (YP_004302702), *Stappia aggregata* IAM 12614 (ZP_01545666; EAV45595), *Marinomonas* sp. MWYL1 (YP_001342133, ABR72198), *Labrenzia alexandrii* DFL-11 (ZP_05115584, EEE46183); *Delftia acidovorans* SPH-1 (YP_001566649, ABX38264), *Burkholderia* sp. CCGE1001 (YP_004230861; ADX57801), *Rhodobacter sphaeroides* ATCC 17029 (YP_001044959; ABN78187), *Rhodobacter sphaeroides* ATCC 17025 (YP_001168251; ABP70946); *Rhodobacter sphaeroides* WS8N (ZP_08415419; EGJ20215), *Rhodobacter sphaeroides* KD131 (YP_002520541; ACM03468), and *Burkholderia* sp. Ch1-1 (ZP_06839743; EFG72573). Without limitation, a D-2-hydroxyacid dehydrogenase encoded by a non-native gene in an engineered microorganism as provided herein can be polypeptides with D-2-hydroxyacid dehydrogenase activity having at least 80%, at least 85%, at least 90%, or at least 95% amino acid sequence identity to any of these non-phosphorylating D-2-hydroxyacid dehydrogenases or others as listed in sequence databases, including conservative variants thereof, and N-terminally and/or C-terminally truncated or modified variants thereof. For example, a nucleic acid molecule useful in the invention can encode a D-2-hydroxyacid dehydrogenase that includes an amino acid sequence that has at least 85% or at least 90% sequence identity to SEQ ID NO:2, SEQ ID NO:29, or to a polypeptide cited herein, or that has at least 85% or at least 90% sequence identity to another D-2-hydroxyacid dehydrogenase identified in a publication or sequence database or to an active fragment thereof. In some instances, a nucleic acid molecule useful in the invention can encode a D-2-hydroxyacid dehydrogenase that has at least 95% sequence identity to a polypeptide as provided herein or identified in a sequence database. In some instances, a nucleic acid molecule useful in the invention can encode a D-2-hydroxyacid dehydrogenase that includes an amino acid sequence that has at least 95% sequence identity to SEQ ID NO:2 or SEQ ID NO:29.

Additional D-isomer specific 2-hydroxyacid dehydrogenases useful in the recombinant microorganisms and methods herein include those having homology to SEQ ID NO:15 or SEQ ID NO:16 such as but not limited to the D-2-hydroxyacid dehydrogenase of *Clostridium beijerinckii* NCIMB 8052 (YP_001309316), *Enterococcus gallinarum* EG2 (ZP_05648199); *Enterococcus casseliflavus* ATCC 12755 (ZP_08145011); the *Carnobacterium* sp. AT7 (ZP_02185893); and *Enterococcus faecium* E1636 (ZP_06695345). Without limitation, a D-2-hydroxyacid dehydrogenase encoded by a non-native gene in an engineered microorganism as provided herein can be polypeptides with D-2-hydroxyacid dehydrogenase activity having at least 85%, at least 90%, or at least 95% amino acid sequence identity to any of these non-phosphorylating D-2-hydroxyacid dehydrogenases or others as listed in publications or sequence databases, including conservative variants thereof and N-terminally and/or C-terminally truncated or modified variants thereof. For example, a nucleic acid molecule useful in the invention can encode a D-2-hydroxyacid dehydrogenase that includes an amino acid sequence that has at least 85% or at least 90% sequence identity to SEQ ID NO:15, SEQ ID NO:16, or to another D-2-hydroxyacid dehydrogenase identified in a sequence listing or database or to an active fragment thereof. In some instances, a nucleic acid molecule useful in the invention can encode a D-2-hydroxyacid dehydrogenase that has at least 95% sequence identity to a polypeptide as provided herein or identified in a sequence database. In some instances, a nucleic acid molecule useful in the invention can encode a D-2-hydroxyacid dehydrogenase that includes an amino acid sequence that has at least 95% sequence identity to SEQ ID NO:15 or SEQ ID NO:16.

Alternatively or in addition, an isocitrate dehydrogenase gene can be expressed in a recombinant microorganism as provided herein. Examples of isocitrate dehydrogenases that can be expressed by microorganisms of the invention include, without limitation, the isocitrate dehydrogenase of *Candidatus Regiella insecticola* LSR1 (EFL92794); *Mycobacterium tuberculosis* CDC1551(AAK47786); *Blattabacterium* sp. (*Cryptocercus punctulatus*) str. Cpu (AEU09317); *Treponema azotonutricium* ZAS-9 (AEF80142); *Staphylococcus pseudintermedius* ED99 (ADX76379); *Paenibacillus polymyxa* E681 (ADM69426); *Escherichia coli* IHE3034 (ADE91794); *Acidithiobacillus ferrooxidans* ATCC 23270 (ACK80956); *Coxiella burnetii* RSA 331 (ABX78669); *Burkholderia pseudomallei* 1106a (AB005966); *Burkholderia mallei* NCTC 10247 (ABO05966); *Burkholderia mallei* NCTC 10229 (ABNO2935); *Burkholderia mallei* SAVP1 (ABM52803); *Mycobacterium avium* 104 (ABK66771); and *Aeromonas hydrophila* subsp. hydrophila ATCC 7966 (ABK38368). In some instances, a nucleic acid molecule useful in the invention can encode an isocitrate dehydrogenase that has at least 85%, at least 90%, or at least 95% sequence identity to a polypeptide as provided herein or identified in a sequence database, including conservative variants thereof and N-terminally and/or C-terminally truncated or modified variants thereof.

A glutamate dehydrogenase that can be encoded by a non-native nucleic acid molecule can include, as nonlimiting examples, the glutamate dehydrogenase of *Chaenocephalus aceratus* (P82264), *Bos Taurus* (NP 872593), *Arabidopsis thaliana* (NP_197318), *Medicago truncatula* (XP_003618972), *Chlorella variabilis* (EFN57943), *Chlamydomonas reinhardtii* (XP_001702270), *Rhodopirellula baltica* SH 1 (NP_867538) *Ktedonobacter racemifer* DSM 44963 (ZP_06967738), or *Roseiflexus* sp. RS-1 (YP_001276062) or a glutamate dehydrogenase that has at least 85%, 90%, or 95% sequence identity to a polypeptide as provided herein or identified in a sequence database, including a conservative variant thereof and/or an N-terminally and/or C-terminally truncated or modified variant thereof.

Microorganisms and Host Cells

The invention provides a recombinant microorganism that expresses a non-native gene encoding a dehydrogenase, in which the recombinant microorganism produces a lipid, where a culture of the recombinant microorganism expressing the dehydrogenase produces a greater amount of the lipid than does a control culture identical to the culture of the dehydrogenase-expressing microorganism, except that the microorganism of the control culture does not include the non-native gene encoding a dehydrogenase. The recombinant microorganism can further include at least one additional non-native gene for the production of a lipid, such as, for example, a non-native gene encoding an enzyme for the production of fatty acids, fatty acid derivatives, and/or glycerolipids. In some examples, a microorganism that includes a non-native gene encoding a dehydrogenase and a non-native gene encoding a polypeptide that participates in synthesis of a lipid has a higher propagation and/or proliferation rate than does a control microorganism identical in all respects to the microorganism expressing a non-native dehydrogenase gene and a non-native gene encoding a polypeptide that participates in the production of a lipid, except that the control microorganism does not include the non-native gene encoding a dehydrogenase. For example, a culture of a recombinant microorganism as disclosed herein that includes a non-native gene encoding a dehydrogenase and a non-native gene encoding a polypeptide for production of a lipid (e.g., fatty acid product) synthesis can achieve a higher cell density after three, four, five, six, or more than six days in culture than the cell density achieved by a control microorganism identical in all respects to the microorganism expressing a non-native dehydrogenase gene and a non-native gene encoding a polypeptide that participates in the production of a lipid, except that the control microorganism does not include the non-native gene encoding a dehydrogenase. For example, a culture of the recombinant microorganism expressing a non-native dehydrogenase gene and a non-native gene that encodes a polypeptide that participates in the production of a lipid can achieve a higher cell density than a control culture of a microorganism lacking the non-native dehydrogenase gene under culture conditions in which the lipid, e.g., a fatty acid product, is being produced. The fatty acid product may be a lipid not naturally made by the host microorganism (i.e., not made by the host microorganism lacking the non-native gene that participates in the production of the lipid).

Recombinant microorganisms or host cells of the invention may be of prokaryotic or eukaryotic origin, including, without limitation, fungi, heterokonts, algae, eubacteria, archaebacteria, green nonsulfur bacteria, purple nonsulfur bacteria, or cyanobacteria. Recombinant host cells can be, but are not limited to, photosynthetic organisms. Photosynthetic organisms include higher plants (i.e., vascular plants), bryophytes, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "picoplankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria).

Algae for use in the invention, include without limitation, microalgae, such as but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halo cafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachlorella, Tetraselmis, Thalassiosira, Viridiella,* or *Volvox* species. For example, the host microorganism can be a diatom, and can be of a genus selected from the group consisting of *Amphora, Chaetoceros, Cyclotella, Fragilaria, Navicula, Phaeodactylum,* or *Thalassiosira*. Alternatively, in some examples the host strain can be a eustigmatophyte, such as a species of *Nannochloropsis* or *Ellipsoidon* or a green alga, such as, but not limited to, a species of *Chlorella, Chlorogonium, Pseudochlorella, Scenedesmus,* or *Tetraselmis*.

Alternatively, the recombinant microorganism can be a species of cyanobacteria. More than thirty cyanobacterial genomes have been completely sequenced to date, including, for example, the genomes of various *Acaryochloris, Arthrospira, Cyanobacterium, Cyanothece, Gloeobacter, Microcystis, Nostoc, Prochlorococcus, Synechococcus, Synechocystis,* and *Thermosynechococcus* species, and many cyanobacterial species been manipulated using molecular biological techniques, including for example the cyanobacteria *Leptolyngbya* sp. Strain BL0902, *Anabaena* (Nostoc) sp. PCC 7120, *Anabaena variabilis* ATCC 29413, *Nostoc punctiforme* ATCC 29133, *Nostoc* sp. PCC 7422, *Synechocystis* sp. PCC 6803, *Synechococcus elongatus* PCC 7942, *Synechococcus elongatus* PCC 7002, etc. (Taton et al. (2012) *PLoS One* Vol. 7, Iss. 1 e30910; Ruffing (2011) *Bioengineered Bugs* 2:136-149). The recombinant microorganisms provided herein can be, as non-limiting examples, of any of the following genera of cyanobacteria: *Agmenellum, Anabaena, Anabaenopsis, Anacystis, Aphanizomenon, Arthrospira, Asterocapsa, Borzia, Calothrix, Chamaesiphon, Chroococcus, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*. For example, the recombinant photosynthetic microorganism can be a *Synechococcus, Synechocystis,* or *Thermosynechococcus* species. Alternatively, the recombinant photosynthetic microorganism can be a *Cyanobium, Cyanothece,* or *Cyanobacterium* species, or further alternatively, the recombinant photosynthetic microorganism can be a *Gloeobacter, Lyngbya,* or *Leptolyngbya* species.

The recombinant microorganism can include a non-native gene encoding any dehydrogenase disclosed herein. In some examples, the microorganism expresses a non-native gene encoding an NADPH-producing dehydrogenase, such as, for example, NADP-dependent glyceraldehyde-3-phosphate dehydrogenase (nonphosphorylating) (EC 1.2.1.9), malic enzyme, isocitrate dehydrogenase, glutamate dehydrogenase, glucose-6-phosphate dehydrogenase, or 6-phosphogluconate dehydrogenase. Alternatively or in addition, the recombinant microorganism can express a gene encoding an aldehyde dehydrogenase, a methylmalonate semialdehyde dehydrogenase, or a D-2-hydroxyacid dehydrogenase. In particular examples, a recombinant microorganism as provided herein can include a non-native nucleic acid molecule comprising a nucleic acid sequence that encodes a polypeptide comprising an amino acid sequence having at least 50%, at least 55%, at least 60% at least 65%, at least 70%, at least 75%, at least 80%, or at least 85%, for example at least 90%, at least 95%, at least 96%, at least 97%, at least 98%, at least 99%, or about 100% sequence identity to the amino acid sequence of SEQ ID NO:10, SEQ ID NO:11, SEQ ID NO:13, SEQ ID NO:4, SEQ ID NO:6, SEQ ID NO:7, SEQ ID NO:18, SEQ ID NO:19, SEQ ID NO:15, SEQ ID NO:16, SEQ ID NO:2, or SEQ ID NO:29, operably linked to a heterologous promoter.

For example, a recombinant microorganism can include a non-native gene encoding a dehydrogenase of the pentose phosphate pathway, such as a glucose-6-phosphate dehydrogenase or a 6-phosphogluconate dehydrogenase, such as, for example, any disclosed herein. The 6-phosphogluconate dehydrogenase can be derived from any organism, prokaryotic or eukaryotic, and can, for example, be from the same species as the host microorganism, where the non-native gene may be an introduced gene or an endogenous gene that is overexpressed by genetically engineering a promoter operably linked to the endogenous 6-phosphogluconate dehydrogenase gene. Alternatively or in addition, the 6-phosphogluconate dehydrogenase may include an amino acid sequence having at least 50%, at least 55%, at least 60%, at least 65%, at least 70%, at least 75%, at least 80%, at least 85%, at least 90%, or at least 95% sequence identity to SEQ ID NO:10, SEQ ID NO:11 or to an active fragment thereof. For example, the 6-phosphogluconate dehydrogenase can include an amino acid sequence having at least 85%, at least 90%, at least 95%, at least 96%, at least 97%, at least 98%, at least 99%, or 100% sequence identity to SEQ ID NO:10 or SEQ ID NO:11 or to an active fragment thereof. Alternatively or in addition, the 6-phosphogluconate dehydrogenase may include an amino acid sequence having at least 50%, at least 55%, at least 60%, at least 65%, at least 70%, at least 75%, at least 80%, at least 85%, at least 90%, or at least 95% sequence identity to SEQ ID NO:13 or to an active fragment thereof. For example, the 6-phosphogluconate dehydrogenase can include an amino acid sequence having at least 85%, at least 90%, at least 95%, at least 96%, at least 97%, at least 98%, at least 99%, or 100% sequence identity to SEQ ID NO:13 or to an active fragment thereof. The host microorganism can further include, in addition to a non-native gene encoding a encoding a 6-phosphogluconate dehydrogenase, at least one additional non-native gene that encodes a polypeptide that participates in lipid biosynthesis, e.g., synthesis of a fatty acid product. A culture of the recombinant host microorganism that includes a non-native 6-phosphogluconate dehydrogenase gene and a non-native lipid biosynthesis gene can produce a higher amount of a fatty acid product than is produced by a culture of a control microorganism identical in all respects to the recombinant host microorganism, except that the control microorganism does not include a non-native 6-phosphogluconate dehydrogenase gene. Additionally, the recombinant host microorganism that includes a non-native gene encoding a 6-phosphogluconate dehydrogenase and a non-native gene that encodes a polypeptide that participates in synthesis of a fatty acid product can have a higher propagation and/or proliferation rate and/or can achieve a higher cell density than can be achieved by the control microorganism under culture conditions where the fatty acid product is being produced. In particular examples, the lipid produced in a higher amount by a culture of the recombinant microorganism is a fatty acid product that is not produced by the microorganism in the absence of expression of the non-native gene for lipid production.

In further examples, a recombinant microorganism can include a non-native gene encoding an aldehyde dehydrogenase, including, but not limited to, any disclosed herein. The aldehyde dehydrogenase can be derived from any organism, prokaryotic or eukaryotic, and can, for example, be from the same species as the host microorganism, where the non-native gene may be an introduced gene or an endogenous gene that is overexpressed by genetically engineering a promoter operably linked to the endogenous aldehyde dehydrogenase gene. In various illustrative examples, the aldehyde dehydrogenase may include an amino acid sequence having at least 50%, at least 55%, at least 60%, at least 65%, at least 70%, at least 75%, at least 80% or at least 85%, at least 90%, or at least 95% sequence identity to SEQ ID NO:4, SEQ ID NO:6 or SEQ ID NO:7, or to an active fragment thereof. For example, the aldehyde dehydrogenase can include an amino acid sequence having at least 85%, at least 90%, at least 95%, at least 96%, at least 97%, at least 98%, at least 99%, or 100% sequence identity to SEQ ID NO:4, SEQ ID NO:6, or SEQ ID NO:7. The host microorganism that includes a non-native gene encoding an aldehyde dehydrogenase can further include an additional non-native gene that encodes a polypeptide that participates in lipid biosynthesis, e.g., synthesis of a fatty acid product. A culture of the recombinant host microorganism that includes a non-native aldehyde dehydrogenase gene and a non-native lipid biosynthesis gene can produce a higher amount of a fatty acid product than is produced by a culture of a control microorganism identical in all respects to the recombinant host microorganism, except that the control microorganism does not include a non-native aldehyde dehydrogenase gene. Additionally, the recombinant host microorganism that includes a non-native gene encoding an aldehyde dehydrogenase and a non-native gene that encodes a polypeptide that participates in synthesis of a fatty acid product can have a higher propagation and/or proliferation rate and/or can achieve a higher cell density than can be achieved by the control microorganism under culture conditions where the fatty acid product is being produced. In particular examples, the lipid produced in a higher amount by the recombinant microorganism is a fatty acid product that is not produced by the microorganism in the absence of expression of the non-native gene for encoding a polypeptide for lipid production.

For example, the aldehyde dehydrogenase can be a methylmalonate semialdehyde dehydrogenase, and the host microorganism can include a non-native gene encoding a methylmalonate semialdehyde dehydrogenase, such as, but not limited to, any disclosed herein. For example, a methylmalonate semialdehyde dehydrogenase can include an amino acid sequence having at least 50%, at least 55%, at least 60%, at least 65%, at least 70%, at least 75%, at least 80%, at least 85%, at least 90%, or at least 95%, identity to SEQ ID NO:18 or SEQ ID NO:19, or to an active fragment thereof. In some examples, the host microorganism can include a non-native gene encoding a methylmalonate semialdehyde dehydrogenase having at least 85%, at least 90%, at least 95%, at least 96%, at least 97%, at least 98%, at least 99%, or 100% sequence identity to SEQ ID NO:18 or SEQ ID NO:19.

In further examples, a recombinant microorganism can include a non-native gene encoding a D-2-hydroxyacid dehydrogenase, such as, but not limited to, any disclosed herein. The D-2-hydroxyacid dehydrogenase can be derived from any organism, prokaryotic or eukaryotic, and can be from the same species as the host microorganism, where the non-native gene may be an introduced gene or an endogenous gene that is overexpressed, for example, by genetically engineering a promoter operably linked to the endogenous D-2-hydroxyacid dehydrogenase gene. In various examples, the microorganism includes a non-native gene encoding a D-2-hydroxyacid dehydrogenase that includes an amino acid sequence that has at least 50%, at least 55%, at least 60%, at least 65%, at least 70%, at least 75%, at least 80% at least 85%, at least 90%, or at least 95% sequence identity to SEQ ID NO:2 or SEQ ID NO:29, or to an active fragment thereof. For example, the D-2-hydroxyacid dehydrogenase can include an amino acid sequence having at least 85%, at least 90%, or at least 95%, at least 96%, at least 97%, at least 98%, at least 99%, or 100% sequence identity to SEQ ID NO:2 or SEQ ID NO:29. In further examples, the microorganism includes a non-native gene encoding a D-2-hydroxyacid dehydrogenase that includes an amino acid sequence that has at least 50%, at least 55%, at least 60%, at least 65%, at least 70%, at least 75%, at least 80% at least 85%, at least 90%, or at least 95% sequence identity to SEQ ID NO:15 or SEQ ID NO:16, or to an active fragment thereof. For example, the D-2-hydroxyacid dehydrogenase can include an amino acid sequence having at least 85%, at least 90%, or at least 95%, at least 96%, at least 97%, at least 98%, at least 99%, or 100% sequence identity to SEQ ID NO:15 or SEQ ID NO:16. The host microorganism that includes a non-native gene encoding a D-2-hydroxyacid dehydrogenase can further include an additional non-native gene that encodes a polypeptide that participates in lipid biosynthesis, e.g., synthesis of a fatty acid product. A culture of the recombinant host microorganism that includes a non-native D-2-hydroxyacid dehydrogenase gene and a non-native lipid biosynthesis gene can produce a higher amount of a fatty acid product than is produced by a culture of a control microorganism identical in all respects to the recombinant host microorganism, except that the control microorganism does not include the non-native D-2-hydroxyacid dehydrogenase gene. Additionally, the recombinant host microorganism that includes a non-native gene encoding a D-2-hydroxyacid dehydrogenase and a non-native gene that encodes a polypeptide that participates in synthesis of a fatty acid product can have a higher propagation and/or proliferation rate and/or can achieve a higher cell density than can be achieved by the control microorganism under culture conditions where the fatty acid product is being produced. The lipid produced in a higher amount by the recombinant microorganism may in some examples be a fatty acid product that is not produced by the microorganism in the absence of expression of the non-native gene for encoding a polypeptide for lipid production.

In particular nonlimiting examples, the recombinant microorganism comprising a non-native gene encoding a dehydrogenase and an additional non-native gene encoding a polypeptide that participates in the production of a fatty acid product not normally produced by the microorganism (e.g., not produced by the species or strain of microorganism used as a host microorganism when not transformed with a non-native gene encoding a polypeptide that participates in the production of a fatty acid product) can be a recombinant photosynthetic microorganism, in which a culture of the recombinant photosynthetic microorganism produces a greater amount of the fatty acid product than is produced by a control culture identical in all respects except that the recombinant photosynthetic microorganism of the control culture does not include or does not express the non-native gene encoding the dehydrogenase. For example, the host microorganism can be a species of eukaryotic microalgae that does not naturally produce, e.g., free fatty acids, fatty aldehydes, fatty alcohols, fatty acid esters (e.g., fatty acid alkyl esters), or wax esters, where the recombinant host microorganism transformed with a dehydrogenase gene and a gene for production of a fatty acid product is able to produce one or more of a free fatty acid, fatty aldehyde, fatty alcohol, alkane, alkene, fatty acid ester, or wax ester. Alternatively, the host microorganism can be a species of cyanobacteria that does not naturally produce, e.g., a free fatty acid, fatty alcohol, alkane, alkene, fatty acid ester, wax ester, or triglyceride, where the recombinant host microorganism transformed with a dehydrogenase gene and a gene for production of a fatty acid product is able to produce one or more of a free fatty acid, fatty alcohol, alkane, alkene, fatty acid ester, wax ester, or triglyceride.

Preferably, a culture of the photosynthetic microorganism that includes a non-native gene encoding a dehydrogenase and a non-native gene encoding a polypeptide that participates in the production of a lipid produces a greater amount of a fatty acid product than is produced by a culture of an otherwise identical photosynthetic microorganism that lacks the non-native gene encoding the dehydrogenase. For example, a photoautotrophic culture of the photosynthetic microorganism that includes a non-native gene encoding a dehydrogenase and a non-native gene encoding a polypeptide that participates in the production of a lipid can preferably produce a greater amount of a fatty acid product than is produced by a photoautotrophic culture of an otherwise identical photosynthetic microorganism that lacks the non-native gene encoding the dehydrogenase. Additionally or alternatively, a culture of the recombinant photosynthetic microorganism can achieve a higher cell density while producing a lipid under photoautotrophic conditions, e.g., using inorganic (non-reduced) carbon as the carbon source for production of the fatty acid product.

Genetic Modifications for Production of Fatty Acid Products

A recombinant microorganism as provided herein can be engineered to produce a lipid, such as, for example, a fatty acid, a fatty acid derivative (e.g., a fatty aldehyde, a fatty alcohol, a fatty acid ester, a wax ester, an alkane, or an alkene), or a glycerolipid (e.g., a triglyceride). For example, the recombinant microorganism can include at least one non-native gene that encodes one or more of an acyl-ACP thioesterase, an acyl-CoA thioesterase, a hydroxybenzoyl thioesterase, a polypeptide having lipolytic activity, an acyl-ACP reductase, an acyl-CoA reductase, a carboxylic acid reductase, a wax synthase, a decarbonylase, a decarboxylase, a glycerolphosphate acyltransferase (GPAT), a lysophosphatidic acid acyltransferase (dehydrogenase), a phosphatidic acid phosphatase (PAP), or a diacylglycerol O-acyltransferase (DGAT).

In various nonlimiting and illustrative examples, a recombinant microorganism that includes a non-native dehydrogenase gene can include, for example, one or more of an acyl-ACP thioesterase, acyl-CoA thioesterase, hydroxybenzoyl thioesterase, and a polypeptide having lipolytic activity for the production of free fatty acids or for the production of fatty aldehydes, fatty alcohols, fatty acid esters, wax esters, alkanes, or alkenes generated from fatty acids. The recombinant microorganism can include, for example, a non-native gene encoding an acyl-ACP thioesterase, such as any disclosed herein, such as, for example, a higher plant FatB thioesterase. In an illustrative example, the microorganism can include a non-native gene encoding a *Cuphea* acyl-ACP thioesterase or a variant thereof, for example, the acyl-ACP thioesterase of SEQ ID NO:21. The recombinant microorganism can be a microalga, for example, a cyanobacterium.

Alternatively or in addition, a recombinant microorganism that includes a non-native dehydrogenase gene can include a non-native acyl reductase gene for the production of a fatty aldehyde, and optionally, a decarbonylase that converts a fatty aldehyde to an alkane. The aldehyde-forming acyl reductase can be an acyl-ACP reductase or an acyl-CoA reductase. Further alternatively or additionally, a recombinant microorganism that includes a non-native dehydrogenase gene can include an acyl reductase gene for the production of a fatty alcohol, and optionally, a wax synthase that converts a fatty alcohol to a wax ester. The alcohol-forming acyl reductase can be an acyl-ACP reductase or an acyl-CoA reductase. A wax synthase can optionally be a wax synthase that is able to use acyl-ACP as a substrate. The recombinant microorganism can further include an acyl-CoA synthetase, or, in examples where enzymes such as acyl reductases and/or wax synthases or acyltransferases are able to use acyl-ACP as a substrate, may not include a non-native gene encoding an acyl-CoA synthetase. In particular examples, the recombinant microorganism used for the production of a fatty acid derivative is a cyanobacterial species that does not naturally include a gene encoding either of an acyl-CoA synthetase or an acyl-ACP thioesterase and further does not include an exogenous (i.e., introduced) gene encoding either or both of an acyl-CoA synthetase or an acyl-ACP thioesterase.

Alternatively or in addition, a recombinant microorganism that includes a non-native dehydrogenase gene can include a non-native gene encoding an acyl transferase, such as, but not limited to, a DGAT, LPAAT, or GPAT, and can optionally additionally or alternatively include a non-native gene encoding a PAP.

Specifically included for use in the constructs and microorganisms disclosed herein are nucleic acid sequences that encode polypeptides having at least 65%, 70%, 75%, 80%, 85%, 86%, 87%, 88%, 89%, 90%, 91%, 92%, 93%, 94%, 95%, 96%, 97%, 98%, or 99%, amino acid sequence identity to known or suspected enzymes of a given class, including but not limited to the examples below, where the encoded polypeptides have activity of the enzyme class. For example, a nucleic acid sequence that encodes a thioesterase, lipase, acyl-CoA synthetase, aldehyde forming reductase, alcohol-forming reductase, carboxylic acid reductase, decarbonylase, decarboxylase, wax synthase, acyltransferase, or transporter useful in the microorganisms and methods provided herein can have at least 85%, at least 90%, or at least 95% amino acid sequence identity to an identified thioesterase, lipase, acyl-CoA synthetase, aldehyde forming reductase, alcohol-forming reductase, carboxylic acid reductase, decarbonylase, decarboxylase, wax synthase, or acyltransferase, e.g., a sequence annotated in a database, including but not limited to those disclosed herein.

Thioesterases

For example, in addition to an expression system for one or more recombinant genes encoding a dehydrogenase, a host microorganism can include a non-native gene encoding a thioesterase. As used herein, the term "thioesterase" is intended to include hydrolases capable of acting on a thioester bond to release fatty acids. Host microorganisms can produce free fatty acids or can convert the fatty acids released by a thioesterase to other products, such as fatty alcohols or wax esters. Thioesterases can correspond to, e.g., Enzyme Commission Number 3.1.2.2, 3.1.2.14, 3.1.2.18, 3.1.2.19, 3.2.1.20, 3.1.2.22, 3.1.2.23, or 3.1.2.27. An exogenous thioesterase expressed in the host microorganism can be, for example, an acyl-ACP thioesterase, an acyl-CoA thioesterase, or a hydroxylbenzoyl thioesterase. For example, a microorganism for the production of free fatty acids in some embodiments can be transformed with a gene encoding an exogenous acyl-ACP thioesterase, such as a gene encoding a polypeptide that when queried against the Pfam database, provides a match with Pfam PF01643 having a bit score of less than or equal to 20.3 (the gathering cut-off for PF01643). The exogenous acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g. *Cuphea carthagenensis, Cuphea wrightii* (e.g., GenBank Accession AAC49784), *Cuphea lanceolata* (e.g., GenBank Accession CAA54060), *Cuphea palustris*, (e.g., GenBank Accessions AAC49783; AAC49179); *Cuphea hookeriana* (e.g., GenBank Accessions AAC72882; AAC49269; AAC72881; AAC72883), *Cuphea calophylla* (e.g., GenBank Accession ABB71580) or genes of various *Cuphea* species disclosed in United States patent application publication US 2011/0020883, incorporated by reference herein) or genes from other higher plant species. In further examples, a microorganism used in the methods and cultures disclosed herein can include a gene encoding an acyl-ACP thioesterase from species such as but not limited to, *Arabidopsis* (e.g., GenBank Accessions XP_002885681; NP_172327); *Arachis hypogaea* (e.g., GenBank Accession AB038556); *Brassica* species (e.g., GenBank Accession CAA52069.1), *Camellia oleifera* (e.g., GenBank Accession ACQ57189); *Cinnamonum camphorum* (e.g., GenBank Accession AAC49151); *Cocos nucifera* (e.g., GenBank Accessions AEM72519; AEM72520; AEM72521); *Glycine max* (e.g., GenBank Accession ABD91726); *Garcinia mangostana* (e.g., GenBank Accession AAB51525); *Gossypium hirsutum* (e.g., GenBank Accession AAD01982); *Helianthus annuus* (e.g., GenBank Accession AAQ08226); *Jatropha curcas* (e.g., GenBank Accession ABU96744); *Macadamia tetraphylla* (e.g., GenBank Accession ADA79524); *Elaeis oleifera* (e.g., GenBank Accession AAM09524); *Elaeis guineensis* (e.g., GenBank Accession AAD42220); *Oryza sativa* (e.g., GenBank Accession BAA83582); *Populus tomentosa* (e.g., GenBank Accession ABC47311); *Umbellularia californica* (e.g., GenBank Accession AAC49001); *Ulmus Americana* (e.g., GenBank Accession AAB71731); and *Zea mays* (e.g., GenBank Accession ACG41291), or any of those disclosed in U.S. Pat. Nos. 5,455,167; 5,654,495; and 5,455,167; and in U.S. Patent Appl. Pub. Nos. 2009/0298143 and 2011/0020883; all incorporated by reference herein in their entireties. Further included are acyl-ACP thioesterases from mosses (*Bryophyta*), such as, for example, *Physcomitrella patens* (e.g., GenBank Accession XP 001770108). The foregoing examples are not limiting with regard to the types or specific examples of acyl-ACP thioesterase genes that can be used.

Further included are acyl-ACP thioesterase genes from prokaryotic organisms. Illustrative examples of prokaryotic acyl-ACP thioesterases that may be expressed by a microorganism useful in the methods and cultures provided herein include, but are not limited to acyl-ACP thioesterases from *Desulfovibrio desulfuricans* (e.g. Q312L1); *Elusimicrobium minutum* (e.g. ACC98705); *Carboxydothermus hydrogenoformans* (e.g. YP_359670); *Clostridium thermocellum* (e.g. YP_001039461); *Moorella thermoacetica* (e.g. YP_431036); *Geobacter metallireducens* (e.g. YP_384688); *Salinibacter ruber* (e.g. YP_444210); *Microscilla marina* (e.g. EAY28464); *Parabacteroides distasonis* (e.g. YP_001303423); *Enterococcus faecalis* (e.g. ZP_03949391); *Lactobacillus plantarum* (e.g. YP_003062170); *Leuconostoc mesenteroides* (e.g. YP_817783); *Oenococcus oeni* (e.g. ZP_01544069); *Mycobacterium smegmatis* (e.g. ABK74560); *Mycobacterium vanbaalenii* (e.g. ABM11638); *Rhodococcus erythropolis* (e.g. ZP_04385507; *Rhodococcus opacus* (e.g. YP_002778825), or any of those disclosed in the co-pending, commonly-assigned patent application Ser. No. 13/324,623 entitled "Prokaryotic Acyl-ACP Thioesterases for Producing Fatty Acids in Genetically Engineered Microorganisms", filed on Dec. 13, 2011, which is incorporated herein by reference in its entirety.

In additional examples, a gene encoding an acyl-CoA thioesterase can be introduced into a host microorganism that includes an exogenous nucleic acid molecule encoding a dehydrogenase. An acyl-CoA thioesterase gene transformed into a microorganism for the production of free fatty acids or fatty acid derivatives can be from a plant, animal, or microbial source. For example, a gene encoding the TesA or TesB thioesterase of *E. coli*, or a variant thereof, for example, an acyl-CoA thioesterase such as not limited to a variant as disclosed in WO 2010/075483, incorporated by reference herein in its entirety, can be introduced into a microorganism. Also included are genes encoding proteins that when queried against the Pfam database of protein families are identified as members of Pfam PF02551 (acyl-CoA thioesterase), where the bit score is equal to or greater than the gathering cut off (20.7).

Alternately or in addition, the microorganism can include one or more genes encoding an exogenous hydroxybenzoyl thioesterase, for example an exogenous 4-hydroxybenzoyl thioesterase or 4-chlorobenzoate thioesterase. Genes encoding hydroxybenzoyl thioesterases that may be useful in a microorganism for producing free fatty acids can include, for example, those disclosed in the co-pending, commonly-assigned patent application Ser. No. 13/324,607 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 13, 2011, and which is incorporated herein by reference in its entirety, 4-hydroxybenzoyl thioesterases from *Bacillus* species and Geobacillus species, as well as 4-hydroxybenzoyl thioesterases of *Acidiphilium, Bartonella, Rhodopseudomonas, Magnetospirillum, Burkholderia, Granulibacter, Rhizobium,* and *Labrenzia* species, or the like, or combinations thereof.

Acyl-ACP thioesterases typically can be active to some degree on acyl-ACP substrates having a plurality of different acyl chain lengths, but can have higher activity on (e.g., have a substrate preference for) one or more acyl-ACP substrates having particular acyl chain lengths than on other chain length substrates. For example, an acyl-ACP thioesterase may have a substrate preference for one or more of acyl-ACP substrates having acyl chain lengths of 8, 10, 12, 14, 16, 18, 20, 22, and/or 24 carbons. Additionally or alternately, the acyl-ACP thioesterase can hydrolyze one or more acyl-ACP substrates having an acyl chain length from 8 to 18 carbons, for example from 12 to 16 carbons.

Polypeptides having Lipolytic Activity

Alternatively or in addition to a non-native gene encoding a thioesterase, a recombinant microorganism or host cell of the invention can include one or more non-native genes encoding one or more polypeptides having lipolytic activity, where the polypeptide(s) having lipolytic activity are capable of producing free fatty acids from membrane lipids or storage lipids, e.g., phospholipids, triacylglycerols, diacylglycerols, monoacylglycerols, or the like, or combinations thereof. The polypeptides having lipolytic activity can be, for example, lipases, esterases, cutinases, or amidases. Lipases are enzymes that catalyze the hydrolysis of ester bonds in glycerolipids, including, but not limited to, mono-, di-, and triacyl glycerols, as well as combinations thereof, to release free fatty acids and alcohols.

The use of genes encoding polypeptides having lipolytic activity in microorganisms for the production of free fatty acids is disclosed in commonly-assigned U.S. patent application Ser. No. 13/324,653 entitled "Production of Free Fatty Acids and Fatty Acid Derivatives by Recombinant Microorganisms Expressing Polypeptides Having Lipolytic Activity," filed on Dec. 13, 2011, and which is incorporated herein by reference in its entirety. The polypeptide having lipolytic activity can be for example a lipase, e.g., that liberates a fatty acid from a glycerolipid (including a monoglyceride, a diglyceride, a triglyceride, a phospholipid, a galactolipid, etc.) or can be an amidase. For example, the recombinant microorganism can include a non-native gene encoding a lipase, such as but not limited to a lipase that is a member of a Pfam belonging to the AB Hydrolase Pfam clan (CL0028). For example, a non-native gene encoding a polypeptide having lipolytic activity can encode a lipase that includes a LipA domain identified as conserved protein domain COG1075, or is included in the protein family Pfam PF01674 (Lipase 2); a non-native nucleic acid molecule that encodes a lipase that includes a Lipase 3 domain identified as conserved protein domain COG3675, or is included in the protein family Pfam PF01764 (Lipase 3); a non-native nucleic acid molecule that encodes a lipase that is included in the protein family Pfam PF07819 (PGAP1); or a non-native nucleic acid molecule that encodes a polypeptide that is included in any of the protein families Pfam PF03583, Pfam PF00151 (Lipase), Pfam PF00561 (Ab hydrolase 1), Pfam PF02230 (Ab hydrolase 2), Pfam PF07859 (Ab hydrolase 3), Pfam PF08386 (Ab hydrolase 4), Pfam PF12695 (Ab hydrolase 5), Pfam PF12697 (Ab hydrolase 6), Pfam PF12715 (Ab hydrolase 7), Pfam PF04083 (Ab hydro lipase). Further, the recombinant microorganism can include a non-native gene encoding an amidase having lipolytic activity, such as but not limited to an amidase that recruits to Pfam PF01425 (Amidase) with a bit score greater than the gathering cutoff of 20.1 and can catalyze the release of fatty acids from lipids.

Additionally or alternately contemplated are recombinant microorganisms that are engineered to include gene regulatory sequences that induce or increase expression of an endogenous lipase gene. For example, a microorganism can be engineered such that a heterologous promoter is inserted upstream of a coding region of an endogenous lipase gene. The heterologous promoter can replace an endogenous promoter and/or can be inserted upstream or downstream of the endogenous promoter that regulates expression of the endogenous lipase gene, for example using homologous recombination or site-specific recombination. The heterologous promoter can be a constitutive promoter or an inducible promoter that increases expression of the endogenous lipase gene.

Additionally but optionally, a recombinant microorganism engineered to include an exogenous gene encoding a thioesterase for the production of fatty acids or fatty acid derivatives can further include an exogenous gene encoding a lysophosphatidic acid acyltransferase (LPAAT), where the LPAAT has a different acyl-ACP substrate preference than the acyl-ACP substrate preference of the thioesterase. Alternatively, the genetically engineered microorganism, which can be a genetically engineered cyanobacterium, can overexpress an endogenous LPAAT gene having a different substrate preference than the substrate preference of an exogenous thioesterase gene. The engineering of microorganisms such as cyanobacteria to increase fatty acid production by expression of LPAAT genes is disclosed in co-pending and commonly-assigned U.S. patent application Ser. No. 13/404,7171 entitled "Enhanced Production of Fatty Acids and Fatty Acid Derivatives by Recombinant Microorganisms" filed Feb. 24, 2012, and incorporated herein by reference in its entirety.

Acyl-CoA Synthetases

A recombinant or isolated nucleic acid molecule used in the microorganisms and methods of the invention can optionally comprise a nucleic acid sequence encoding an acyl-CoA synthetase, where the acyl-CoA synthetase may couple a free fatty acid generated by a thioesterase or lipase to coenzyme A to provide acyl-CoA, which is a substrate for many reductases, wax synthases, and acyltransferases that can produce aldehydes, alcohols, wax esters, and glycerolipids using an acyl-CoA substrate. The acyl-CoA synthetase can be, for example, a prokaryotic acyl-CoA synthetase, for example, such as FadD (NP_416319) or FadK of *E. coli* (NP_416216), or their homologs in other bacterial species, including, as nonlimiting examples, the acyl-CoA synthetase of *Vibrio splendidus* (EGU44230) or *Marinobacter adhaerens* HP15 (ADP96803). Additional nonlimiting examples of prokaryotic proteins known to have or suspected of having acyl-CoA synthetase activity include, but are not limited to, *Acinetobacter* sp. ADP1 fadD (YP_045024), *Haemophilus influenza* RdKW20 fadD (NP_438551), *Bacillus halodurans* C-125 BH3103 (NP_243969), *Bacillus subtilis* yhfL (NP_388908), *Pseudomonas fluorescens* Pfo-1 Pfl-4354 (YP_350082), *Comamonas testosteroni* KF-1 EAV15023 (ZP_01520072), *Pseudomonas aeruginosa* fadD1 (NP_251989), *Pseudomonas aeurginosa* PAO1 fadD2 (NP_251990), *Rhizobium etli* CFN42 fadD (YP_468026), *Rhodopseudomonas palustris* Bis B18 RPC_4074 (YP_533919), *Rasltonia Solanacearum* GM1 1000 fadD1 (NP_520978), *Mycobacterium tuberculosis* H37Rv fadDD35 (NP_217021), *Myco-*

*bacterium tuberculosis* H37Rv fadDD22 (NP_217464), and *Stenotrophomonas Maltophilia* R551-3 PRK0059 (ZP_01644857).

In further examples, the nucleic acid sequence encoding an acyl-CoA synthetase can encode an acyl-CoA synthetase derived from a fungal species, such as, for example, a *Saccharomyces cerevisiae* acyl-CoA synthetase (e.g., the medium chain fatty acyl-CoA synthetase Faa2p (NP_010931) or the SCRG_04483 acyl-CoA synthetase (EDV08843) or a *Yarrowia lipolytica* acyl-CoA synthetase (e.g., CAG77892). Additional acyl-CoA synthetase genes that may be used in the constructs and microorganisms disclosed herein include acyl-CoA synthetases of plants, such as, for example, the long chain acyl-CoA synthetase of *Brassica napus* (CAC19877) or the long chain acyl-CoA synthetase of *Arabidopsis thaliana* (AEE74324), or the Yng-1-like acyl-CoA synthetase of *Glycine max* (XP_003524920), and acyl-CoA synthetases of algal species, such as, for example, the long chain acyl-CoA synthetase of *Chlamydomonas reinhardtii* (XP_001693692), or acyl-CoA synthetases of Nannochloropsis oculata (e.g., ADP09391), or *Chlorella variabilis* (e.g., EFN56588). Further considered are acyl-CoA synthetases of animal species, including insects (e.g., *Apis mellifera*, for example, the acyl-CoA synthetase family member 2, mitochondrial precursor, NP_001193902) and mammals such as *Mus musculus* (e.g., the "MACS" acyl-CoA synthetase, EDL17174).

Alternatively, recombinant microorganisms as provided herein may not include an exogenous or overexpressed gene encoding an acyl-CoA synthetase, a thioesterase, and/or a lipase. For example, a recombinant microorganism as provided herein may produce one or more of a fatty aldehyde, fatty alcohol, alkane, alkene, or wax ester without utilizing or generating an acyl-CoA substrate. For example, methods for producing fatty alcohols and wax esters using non-acyl-CoA substrates are provided in the co-pending, commonly-assigned U.S. patent application No. 61/539,640 entitled "Fatty Alcohol-Forming Acyl-ACP Reductases", filed on Sep. 27, 2011, incorporated herein by reference in its entirety, and in the co-pending, commonly-assigned U.S. patent application Ser. No. 13/413,426 entitled "Acyl-ACP Wax Ester Synthases", filed on Mar. 6, 2012 also incorporated herein by reference in its entirety.

Aldehyde-producing Reductases

For the production of fatty aldehydes, which can optionally be further converted to products such as fatty alcohols, wax esters, or alkanes, a transgenic microorganism as provided herein can include an exogenous gene(s) that encodes an aldehyde-forming reductase, such as, for example, an aldehyde-forming acyl-CoA reductase, an aldehyde-forming acyl-ACP reductase, or a carboxylic acid reductase. Genes or portions of genes that are listed in GenBank and other genetic databases and that are predicted to encode proteins that are homologous to known acyl-CoA reductases that produce fatty aldehydes, referred to herein as "aldehyde-generating fatty acyl-CoA reductases", can be introduced into various microorganisms in order to test for the production of specific fatty aldehydes or fatty alcohols produced therefrom. Nonlimiting examples of fatty aldehyde-generating acyl-CoA reductases include the Acr1 gene of *Acinetobacter baylyi* (AAC45217.1), the AcrM-1 gene of *Acinetobacter* sp. M-1 (YP_001086217), and the luxC and luxE genes of various photoluminescent bacteria, e.g, an *Altermonas, Photobacterium, Shewanella, Vibrio,* or *Xenorhabdus* species. The enzymes encoded by these and other genes identified, for example, by sequence homology or protein domain can be tested to determine their substrates and products using assays know in the art.

In some examples, the host cell can include a non-native gene encoding an aldehyde-forming acyl-ACP reductase such as but not limited to any of those disclosed in US 2010/0221798 (WO 2009/140696), incorporated by reference herein in its entirety. For example, the recombinant host cell may comprise an aldehyde-forming acyl-ACP reductase that has at least 60%, 70%, 80%, 90% or 95% sequence identity to an aldehyde-forming reductase, e.g., as disclosed in WO 2009/140696 or WO 2011/066137, such as, for example, any of the reductases having the accession numbers AAM82647; AAM82647; BAD78241; ABA22149; BAB76983; ZP_03763674; ACL42791; ZP_01628095; ZP_01619574; YP_001865324; YP_721978; NP_682102; YP_001518341; YP_002371106; ZP_05027136; ZP_03273554; NP_442146; ZP_01728620; ZP_05039135; YP_001802846; NP_926091; YP_001660322; ZP_00516920; CA090781; ZP_01085337; YP_001227841; ABD96327; NP_897828; YP_001224378; ABD96480; ZP_01123215; ABB92249; ZP_01079773; YP_377636; NP_874926; NP_895058; ABD96274; ABD96442; ZP_01469469; ZP_05045052; YP_001014416; YP_001010913; YP_381056; YP_001550421; NP_892651; YP_001090783; ZP_01472595; YP_293055; ZP_05138243; YP_731192; YP_001483815; YP_001008982; YP_473896; YP_478638; or YP_397030. In some examples the recombinant host cell includes an exogenous gene encoding an aldehyde-forming acyl-ACP reductase, where the aldehyde-forming acyl-ACP reductase can be from a cyanobacterial species, and may be from the same species as the host microorganism, or may be from a different species. Alternatively, a cyanobacterial host can be engineered to overexpress an endogenous acyl-ACP reductase gene.

Nonlimiting examples of gene encoding carboxylic acid reductases that can be used in the invention include the *Nocardia* CAR gene (AY495697) and homologs thereof, some of which are disclosed in US2010/0105963, incorporated by reference herein in its entirety.

Alcohol-Forming Fatty Acyl Reductases

For production of a fatty alcohol (that can, optionally, be used as a substrate by a wax ester synthase) a nucleic acid molecule as provided herein can further a sequence encoding a fatty alcohol-forming acyl reductase or "FAR" that can reduce acyl-CoA to a fatty alcohol. FARs have been identified in, e.g., *Euglena* (see, e.g., Teerawanichpan et al., *Lipids* 45:263-273 (2010)), *Arabidopsis* (see, e.g., Rowland et al., *Plant Physiol.* 142:866-877 (2006), Doan et al., *J. Plant Physiol.* 166:787-796 (2009) and Domergue et al., *Plant Physiol.* 153:1539-1554 (2010)), *Artemisia* (see, e.g., Maes et al., *New Phytol.* 189:176-189 (2011)), jojoba (see, e.g., Metz et al., *Plant Physiol.* 122:635-644 (2000)), moth (see, e.g., Lienard et al., *Proc. Natl. Acad. Sci.* 107:10955-10960 (2010)), bee (see, e.g., Teerawanichpan et al., *Insect Biochemistry and Molecular Biology* 40:641-649 (2010)) and mammals (see, e.g., Honsho et al., *J. Biol. Chem.* 285:8537-8542 (2010)). An alcohol-forming fatty acyl reductase useful in microorganisms and methods of the invention can be any alcohol-forming reductase that has activity in the host microorganism.

Nonlimiting examples of other alcohol-forming fatty acyl reductases that can be used include, but are not limited to, bfar from *Bombyx mori* (BAC79426), jjfar from *Simmondsia chinensis* (AAD38039), an acyl-CoA reductase from *Triticum aestivum* (CAD30694 or CAD30692), mfar1 from *Mus*

*musculus* (NP_081655), mfar2 from *Mus musculus* (NP_848912), hfar from *H. sapiens* (NP_115604), FARXIII from *Ostrinia scapulalis* (ACJ06520), MS2 from *Z. mays* (NP_001151388 or EU970865), or MS2 (NP_187805), FAR4 (NP_001030809 or NP_190040), FARE (67633703), CER4 (NP_567936) or Ath (NP567936) from *Arabidopsis thaliana*, Yev-pgFAR from *Yponomeuta evonymellus* (GQ907231-GQ907233), Yro-pgFAR from *Yponomeuta rorellus* (GQ907234), Ypa-pgFAR from *Yponomeuta padellus* (GQ907235), OnuE from *Ostrinia nubilalis* (FJ807735), Has from *Homo sapiens* (AAT42129), etc.

An alcohol-forming fatty acyl reductase useful in microorganisms and methods of the invention can also or alternatively be a prokaryotic alcohol-forming acyl-CoA reductase such as *Marinobacter aquaeolei* VT8 Maqu_2220 (YP_959486), *Marinobacter algicola* DG893 (ZP_01892457); *Hahella chejuensis* KCTC 2396 HCH_05075 (YP_436183); *Oceanobacter* sp. RED65 (ZP_01305629), or *Marinobacter aquaeoli* VT8 2220 Maqu_2507 gene (ABM19582).

Alcohol-forming reductases that are able to use acyl-ACP as a substrate (and can be used for the production of fatty alcohols and wax esters in recombinant microorganisms that lack an exogenous and/or endogenous acyl-CoA synthetase gene) are disclosed in commonly assigned copending U.S. Patent application 61/539,640 filed Sep. 27, 2011 entitled "Fatty Alcohol-Forming acyl-ACP Reductases" which is incorporated herein by reference in its entirety, and in the co-pending, commonly-assigned U.S. patent application Ser. No. 13/413,426 entitled "Acyl-ACP Wax Ester Synthases", filed on Mar. 6, 2012 also incorporated herein by reference in its entirety.

Wax Ester Synthases

Wax esters are the product of a condensation reaction between a fatty acyl-thioester substrate and a fatty alcohol, catalyzed by a wax ester synthase. Polypeptides having wax ester synthase activity may be polypeptides identified as wax synthases, O-acyltransferases, including membrane-bound O-acyltransferases (MBOATs), diacylglycerol O-acyltransferases (e.g., EC 2.3.1.20), alcohol acyltransferases (AATs, EC 2.3.1.84), long-chain alcohol O-fatty-acyltransferases (e.g., 2.3.1.75). or alcohol synthase/acyl-CoA:diacylglycerol acyltransferases. Some polypeptides identified as diacylglycerol acyltransferases (DGATs) may be found to have wax ester synthase activity. Wax ester synthases have been identified in, e.g., *Acinetobacter* (Ishige et al., *Appl. Environ. Microbiol.* 68:1192-1195 (2002); Kalscheuer and Steinbuchel, *J. Biol. Chem.* 278:8075-8082 (2003); Kalscheuer et al., *Appl. Environ. Microbiol.* 72:1373-1379 (2006)), *Marinobacter* (Holtzapple and Schmidt-Dannert, *J. Bacteriol.* 189:3804-3812 (2007)), *Arabidopsis* (Li et al., *Plant Physiol.* 148:97-107 (2008)), petunia (King et al., *Planta* 226:381-394 (2007)), jojoba (Lardizabal et al., *Plant Physiol.* 122:645-655 (2000), and mammalian species (Cheng and Russell, *J. Biol. Chem.* 279:37798-37807 (2004); Yen et al., *J. Lipid Res.* 46:2388-2397 (2005)).

Wax ester synthases may be identified using methods known in the art, based on structural domain or sequence similarity to a set of known wax ester synthase/DGAT sequences. As nonlimiting examples, a gene that encodes a polypeptide that recruits to Pfam PF03007 (wax ester synthase like acyl-CoA acyltransferase domain) with a bit score greater than the gathering cutoff of 20.6 and an E value of 0.01 or less or recruits to Pfam PF13813 ("MBOAT_2") with a bit score greater than the gathering cutoff of 25.0 and an E value of 0.01 or less can be selected for use in the nucleic acid molecules and microorganisms provided herein.

Wax ester synthesis proteins encoded by nucleic acid molecules provided herein can include, but are not limited to: acyltransferases or wax synthases, fatty acyl transferases, diacylglycerol acyltransferases, acyl-coA wax alcohol acyltransferases, and bifunctional wax ester synthase/acy 1-CoA: diacylglycerol acy transferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter (Alcanivorax) jadensis, Arabidopsis thaliana*, or *Alkaligenes eutrophus*. Wax synthases can also be from a multienzyme complex from *Alkaligenes eutrophus* and other organisms known in the literature to produce wax and fatty acid esters.

Proteins known or suspected of having wax ester synthase activity that are considered for use in the nucleic acid molecules and transgenic microorganisms provided herein include wax synthases from prokaryotic species, such as but not limited to, *Marinobacter hydrocarbonoclasticus* WS 1 (AB021020), *M. hydrocarbonoclasticus* DSM 8798 WS2 (AB021021), *M.* sp. ELB 17 (GenBank Accession EBA00388), *M. aquaeolei* Maqu_0168 WS (YP_957462), *M. adhaerens* HP15 WS (ADP99639), *Hahella chejuensis* KCTC 2396 (YP_432512), *Acinetobacter baumannii* wax ester synthase (EGJ63408), *A. calcoaceticus* WS/DGAT (ZP_06058985) *Acinetobacter baylyi* ADP1 wax ester synthase (AA017391 or Q8GGG1), *Bradyrhizobium japonicum* USDA 110 (NP_769520), *Erythrobacter litoralis* HTCC 2594 (YP_457389), *Rhodococcus opacus* wax ester synthase (BAH53702), *Mycobacterium tuberculosis* wax ester synthase (NP_334638), *M. smegmatis* wax ester synthase (ABK74273), the "WS/DGAT/MGAT" subfamily proteins of *Alcanivorax* species (CAL17252; EDX90960; EDX89052; ZP_05043539; ZP_05041631), wsadp1 from *Nocardia farcinica* IFM 10152 (YP_117375), *Photobacterium profundum* SS9 (YP_130413), *Rhodoferax ferrireducens* DSM 15236 (ZP_00691704), and *Salinibacter ruber* DSM 13855 (YP_446603).

Examples of eukaryotic polypeptides that may be useful as wax synthases include, without limitation, jojoba wax ester synthase JjWS (AF149919), *Euglena gracilis* wax ester synthase (ADI60058), *Arabidopsis thaliana* WSD10-acyltransferase (NP_568547), *Arabidopsis thaliana* GPAT acyltransferase (NP_174499), the putative long-chain-alcohol O-fatty-acyltransferase 4 of *Arabidiopsis thaliana* (NP_200346) *Murraya koenigii* wax ester synthase, acyl-CoA wax alcohol acyltransferase 2 from *H. sapiens* (NP_001002254), mWS from *Mus musculus* (Q6E1M8), SAAT from *Fragaria xananas* (AAG13130), the membrane bound O-acyltransferase (MBOAT) of *Zea mays* (NP_001131179), mdAAT2 from *Malus×domestica* (AAS79797), as well as insect wax ester synthases, etc.

Wax ester synthases that are able to use acyl-ACP as a substrate and can be used, for example, for the production of wax esters in recombinant microorganisms that lack either or both of an exogenous or endogenous gene encoding an acyl-CoA synthetase or a thioesterase include those disclosed in commonly assigned, copending U.S. patent Ser. No. 13/413, 426 entitled "Acyl-ACP Wax Ester Synthases", filed on Mar. 6, 2012 incorporated herein by reference in its entirety. The wax ester synthases able to use acyl-ACP as a substrate can also have DGAT activity and can be useful in the production of triglycerides in recombinant microorganisms such as but not limited to cyanobacteria that lack acyl-CoA, and/or microorganisms that lack either or both of an exogenous or endogenous gene encoding an acyl-CoA synthetase or a thioesterase.

Alternatively or in addition to any of the above non-native genes, a recombinant microorganism of the invention can comprise at least one nucleic acid molecule encoding an exogenous fatty acid decarboxylase or an exogenous fatty aldehyde decarbonylase, and additionally but optionally at least one exogenous nucleic acid molecule encoding an exogenous acyl-CoA reductase, carboxylic acid reductase, or acyl-ACP reductase, and can produce an alkane and/or alkene. For example, a recombinant microorganism as provided herein can include an exogenous nucleic acid molecule encoding a decarbonylase, such as, for example, CER1 of *Arabidopsis thaliana* (NP__171723) or an ortholog of another species, or derivatives thereof, or any of the decarbonylases disclosed in US 20110124071 (WO 2011/062987), incorporated herein in their entireties, which may be expressed along with a non-native gene encoding an aldehyde forming acyl reductase, such as any disclosed hereinabove. Alternatively, the recombinant microorganism as provided herein can include a non-native gene encoding a gene for the production of olefins (alkenes) such as but not limited to any disclosed in US 20100235934 or U.S. Pat. No. 8,110,093, both of which are incorporated herein by reference in their entireties. Alkanes and alkenes produced by the recombinant microorganisms or host cells of the invention can, for example, have chain lengths of 7, 9, 11, 13, 15, 17, 19, 21, and/or 23 carbons, including, for example, chain lengths of 7, 9, 11, 13, 15, and/or 17 carbons, or chain lengths of 7, 9, 11, 13, and/or 15 carbons, or chain lengths of 11, 13, and/or 15 carbons.

To engineer a microorganism for the production of triglycerides (TAGs), a non-native gene encoding one or more of a glycerol-3-phosphate acyltransferase (hereinafter also referred to as "GPAT"; EC 2.3.1.15), "lysophosphatidic acid acyltransferase" or "LPAAT", EC 2.3.1.51, phosphatidate phosphatase (PAP, 3-sn-phosphatidate phosphohydrolase), or diacylglycerol acyltransferases (DGATs, E.C. 2.3.1.20) can be introduced into the microorganism. The genes can be from any source, prokaryotic or eukaryotic. Genes belonging to all of these classes of enzymes are known in the art, and references to genes having these activities can be found, for example, in U.S. patent application publications 2007/0184538, US 2010/0159110, and 20100255551, and in commonly assigned, copending U.S. patent application Ser. No. 13/404,7171 entitled "Enhanced Production of Fatty Acids and Fatty Acid Derivatives by Recombinant Microorganisms" filed Feb. 24, 2012, all of which are incorporated herein by reference in their entireties.

Alternatively or in addition to any of the above modification, a recombinant microorganism of the invention can optionally include an exogenous or recombinant nucleic acid molecule that encodes an enzyme that affects in fatty acid production. For example, a recombinant microorganism as provided herein can include one or more exogenous nucleic acid molecules that encodes a polypeptide that participates in the synthesis of a fatty acid, including, but not limited to, an acetyl-CoA carboxylase, a malonyl CoA: ACP transacylase, or a beta-ketoacyl-ACP synthase, or can be engineered to overexpress an endogenous gene encoding a polypeptide for fatty acid or lipid production.

Further additionally, the recombinant host cell may optionally be engineered to express an exogenous transmembrane transporter to facilitate secretion of one or more fatty acid products. For example, the recombinant host cell can include a non-native gene encoding an ATP-binding cassette (ABC) transporter or an RND pump. In some embodiments, the transporter is at least 80% identical in sequence to a transporter protein encoded by an *Arabidopsis* genes CER5, WBC11, AtMRPS, AmiS2 and AtPGP1, or fatty acid transporter (FATP) genes from *Saccharomyces, Drosophila*, mycobacterial species, or mammalian species.

The above-described recombinant host cells may be used in any of the methods of producing a fatty acid product as described herein.

Additional Modifications for FFA Production

A recombinant microorganism can further comprise a modification of an endogenous nucleic acid molecule that encodes, e.g., an acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof. In certain embodiments, the modification downregulates the endogenous nucleic acid and includes partial, substantial, or complete deletion, silencing, or inactivation of the nucleic acid or its regulatory elements.

In some examples, the host microorganism, which may be, for example, a cyanobacterium, can have attenuated expression of an endogenous gene encoding an acyl-ACP synthetase which participates in the recycling of fatty acids into lipids. The endogenous acyl-ACP synthetase gene can be, for example, downregulated by deletion or mutation of the promoter, or the protein-encoding of the gene can be internally deleted or disrupted, for example, by insertional mutagenesis. Alternatively, the entire acyl-ACP synthetase gene can be deleted, for example, by homologous recombination or other genome modification techniques. In yet further alternatives, gene knockdown constructs such as but not limited to ribozyme, antisense, or RNAi constructs can be introduced into the host cell to attenuate expression of the endogenous acyl-ACP synthetase gene.

Alternatively or in addition, a recombinant microorganism (e.g., a recombinant cyanobacterium) of the invention comprises can be modified such that one or more genes that encode storage carbohydrate and/or polyhydroxyalkanoate (PHA) biosynthesis pathway enzymes are inactivated or down-regulated, and/or such that the enzymes themselves that are operative on such pathways are inhibited. Examples include, but are not limited to, enzymes involved in glycogen, starch, or chrysolaminarin synthesis, including glucan synthases and/or branching enzymes. Other examples include enzymes involved in PHA biosynthesis such as acetoacetyl-CoA synthase and PHA synthase.

Genes may be targeted specifically by disruption, deletion, generation of antisense sequences, generation of ribozymes, RNAi, meganuclease genome modification, and/or other recombinant approaches. Inactivation of the genes can additionally or alternately be accomplished by random mutation techniques such as exposure to UV and/or chemical mutagens, and the resulting genes and/or enzymes can be screened for mutants with the desired activity. The proteins themselves can be inhibited by intracellular generation of appropriate antibodies, intracellular generation of peptide inhibitors, or the like, or some combination thereof.

Nucleic Acid Molecules

The nucleic acid molecules and encoded polypeptides described herein can be used in any of the methods of the invention, and may be included in any of the constructs, vectors, or recombinant microorganisms of the invention. Nucleic acid molecules comprising sequences that encode dehydrogenases are provided for use in host microorganisms and methods for producing fatty acid products, including free fatty acids, fatty aldehydes, fatty alcohols, fatty acid esters, wax esters, alkanes, alkenes, and/or glycerolipids, such as triglycerides. A nucleic acid molecule as disclosed herein can be isolated and/or purified.

The invention provides isolated nucleic acid molecules that comprise a nucleic acid sequence encoding a dehydrogenase, such as any disclosed herein or any active fragment thereof. For example, a nucleic acid molecule as provided herein can include a nucleic acid sequence encoding an aldehyde dehydrogenase, a 2-hydroxyacid dehydrogenase, a D-2-hydroxyacid dehydrogenase, a glyceride-3-phosophate dehydrogenase (non-phosphorylating), a malic enzyme, a glucose-6-phosphate dehydrogenase, a 6-phosphogluconate dehydrogenase, a glutamate dehydrogenase, an isocitrate dehydrogenase, or a sorbitol dehydrogenase.

Expression in a host microorganism (such as a recombinant microorganism that expresses a non-native gene encoding a polypeptide that participates in the synthesis of a lipid) of a sequence of a recombinant nucleic acid molecule that encodes a dehydrogenase as described herein can result in a higher production level of a fatty acid product by a culture of the host microorganism than the production level of a culture of a control microorganism, where the control microorganism is cultured under the same conditions and is substantially identical to the microorganism expressing the nucleic acid sequence encoding a dehydrogenase in all respects, with the exception that the control microorganism does not express a non-native nucleic acid sequence that encodes a dehydrogenase. Additionally, a recombinant host microorganism that includes a recombinant nucleic acid molecule or sequence as provided herein that encodes a dehydrogenase can have a higher propagation and/or proliferation rate than a control microorganism that is identical to the host microorganism comprising the non-native nucleic acid molecule encoding a dehydrogenase in all respects, with the exception that the control microorganism does not include a non-native nucleic acid molecule or sequence that encodes a dehydrogenase. The recombinant host microorganism that includes a recombinant nucleic acid molecule provided herein that includes a sequence encoding a dehydrogenase can have a higher propagation and/or proliferation rate than a control microorganism lacking the non-native nucleic acid molecule encoding a dehydrogenase during a culture period in which the recombinant microorganism is producing a lipid. The recombinant microorganism can be, for example, a photosynthetic microorganism.

In particular examples, a recombinant nucleic acid molecule as provided herein can encode a dehydrogenase that includes an amino acid sequence having at least 50%, at least 55%, at least 60%, at least 65%, at least 70%, at least 75%, at least 80%, at least 85%, at least 90%, at least 95%, at least 96%, at least 97%, at least 98%, at least 99% identity or 100% identity to the amino acid sequence of SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13, or an active fragment thereof.

For example, the invention provides an isolated or recombinant nucleic acid molecule comprising a nucleic acid sequence that encodes a polypeptide having an amino acid sequence that has at least at least 50%, at least 55%, at least 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO:29, or to a portion thereof, for example, to a functional fragment of the polypeptide of SEQ ID NO:29. For example, a nucleic acid molecule as provided herein can encode a polypeptide that includes an amino acid sequence having at least 85% sequence identity to the amino acid sequence of SEQ ID NO:29, or having at least 90% sequence identity to the amino acid sequence of SEQ ID NO:29, or, for example, having at least 95% sequence identity to the amino acid sequence of SEQ ID NO:29, and can comprise a nucleotide sequence that encodes a polypeptide comprising the amino acid sequence of SEQ ID NO:29.

The invention further provides an isolated or recombinant nucleic acid molecule encoding an dehydrogenase can comprise a nucleic acid sequence that encodes a polypeptide having dehydrogenase activity that includes an amino acid sequence that has at least 50%, at least 55%, at least 60%, at least 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO:2, or to a portion thereof, for example, to a functional fragment of the polypeptide. For example, a nucleic acid sequence that encodes a polypeptide having dehydrogenase activity can include an amino acid sequence having at least 85% sequence identity to the amino acid sequence of SEQ ID NO:2, or a functional fragment thereof, or can include an amino acid sequence having at least 90% sequence identity to the amino acid sequence of SEQ ID NO:2, or a functional fragment thereof, or, for example, can include an amino acid sequence having at least 95% sequence identity to the amino acid sequence of SEQ ID NO:2, or a functional fragment thereof, and can comprise a nucleotide sequence that encodes a polypeptide comprising an amino acid sequence that is identical to all or an active fragment of the amino acid sequence of SEQ ID NO:2.

The invention encompasses variations of the nucleotide sequences of the invention, such as those encoding functional fragments or variants of the polypeptides as described herein. Such variants can be naturally-occurring or non-naturally-occurring, such as those induced by various mutagens and mutagenic processes. Variations include, but are not limited to, addition, deletion, and substitution of one or more nucleotides which can result in conservative or non-conservative amino acid changes or amino acid additions and deletions. A given nucleic acid sequence may be modified, for example, by chemical synthesis of nucleic acid molecules or portions thereof, DNA amplification methods that introduce random or directed mutations, standard chemical or irradiation mutagenesis and/or artificial evolution (selection) or domain swapping methods to produce modified sequences. Further dehydrogenase ORFs may be derived from a collection of transcripts, such as a cDNA library, and the sequence of the transcript may be unknown. Accelerated evolution methods are described, e.g. by Stemmer (1994) Nature 370, 389-391, and Stemmer (1994) *Proc. Natl. Acad. Sci. USA* 91, 10747-10751. Mutations include but are not limited to codon optimization to enhance expression of the wild-type sequence in transgenic species such as algae or cyanobacteria (e.g. Burgess-Brown (2008) *Protein Expr. Purif.* 59, 94-102) and mutations resulting from site-specific mutagenesis that alter the amino acid sequence of the dehydrogenases of the invention. Such alteration in amino acid sequence may increase the biological activity of a dehydrogenase of the invention. For example, the nucleotide sequences of the genes encoding the dehydrogenase proteins of the invention may be mutated so as to increase their biological activity so as to increase fatty acid, fatty acid derivative, or lipid production.

For example, the invention provides fragments and variants of a dehydrogenase that have increased activity in comparison to the reference polypeptide, and in certain embodiments, the dehydrogenase fragment or variant may have activity that is increased by at least 5%, 10%, 20%, 30%, 40%, 50%, 60%, 70%, 80%, 90%, 100%, 200%, 300%, 400%, 500%, 600%, 700%, 800%, 900%, or 1000% in comparison to the activity of the dehydrogenase from which the variant is derived. In certain embodiments, the amount of fatty acid product produced by a culture of a host cell expressing the fragment or variant is at least 5%, 10%, 20%, 30%, 40%, 50%, 60%, 70%, 80%, 90%, 100%, 200%, 300%, 400%, 500%, 600%, 700%, 800%, 900% or 1000% of the amount of fatty acid product made by a culture of the host cell expressing the dehydrogenase from which the fragment or variant is derived.

Additionally or alternatively, the invention provides nucleic acid molecules encoding variants of naturally-occurring dehydrogenase amino acid sequences, such as but not limited to variants of dehydrogenase sequences of SEQ ID NO:4, SEQ ID NO:6, SEQ ID NO:7, SEQ ID NO:18, SEQ ID NO:19, SEQ ID NO:2, SEQ ID NO:29, SEQ ID NO:15, SEQ ID NO:16, SEQ ID NO:10, SEQ ID NO:11, or SEQ ID NO:13 or fragments thereof in which at least one amino acid residue has been added or deleted N- and/or C-terminal to, and/or within, the reference sequence. For example, a cellular targeting signal may be added to a protein for directing the protein to a location in the cell, such as the chloroplast.

The invention also encompasses nucleic acid molecules encoding deletion mutants of a dehydrogenase where one or more amino acids have been deleted from the protein. For example, the encoded polypeptide can lack at least 1, 2, 3, 4, 5, 6, 7, 8, 9, 10, 20, 30, 40, 50, 60, 70, or 80 amino acids from the N- and/or C-terminus and can have an amino acid sequence at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13. In some examples, the deleted sequences may include targeting sequences, for example, at least a portion of a chloroplast transit peptide, at least a portion of a mitochondrial targeting sequence, at least a portion of an endoplasmic reticulum targeting sequence, etc.

A substitution, insertion or deletion can adversely affect the protein when the altered sequence substantially inhibits a biological function associated with the protein. In certain embodiments, a variant of an dehydrogenase may have activity that is reduced by not more than about 1%, 2%, 3%, 4%, 5%, 6%, 7%, 8%, 9%, 10%, 15%, 20%, 30%, 40%, or 50%, in comparison to the activity of the dehydrogenase from which the variant is derived (e.g., any of SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13, or other dehydrogenases). In some embodiments, the amount of a fatty acid product produced by a culture of the host cell expressing the dehydrogenase variant is not less than about 99%, 98%, 97%, 96%, 95%, 94%, 93%, 92%, 91%, 90%, 85%, 80% or 75% of the amount of the fatty acid product produced by a culture of the host cell expressing the dehydrogenase from which the variant is derived (e.g., e.g., any of SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13, or other dehydrogenases).

Thus, the present invention also includes an isolated nucleic acid molecule comprising a nucleic acid sequence encoding a polypeptide comprising an amino acid sequence having the amino acid sequence at least 50%, at least 55%, at least 60%, at least 65%, 70%, 75%, 80%, or 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the peptide sequence of SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13; fragments thereof comprising a consecutive sequence of at least 50, for example at least 75, at least 100, at least 125, at least 150 or more amino acid residues of the entire protein; amino acid sequence variants of such sequences, wherein at least one amino acid residue has been inserted N- and/or C-terminal to, and/or within, the disclosed sequence(s) which contain(s) the insertion and substitution; amino acid sequence variants of the disclosed sequence, and/or their fragments as defined above. The contemplated variants can additionally or alternately include those containing predetermined mutations by, e.g. homologous recombination or site-directed or PCR mutagenesis, and the corresponding proteins of other species, including, but not limited to, those described herein, the alleles or other naturally occurring variants of the family of proteins which contain the insertion and substitution; and/or derivatives wherein the protein has been covalently modified by substitution, chemical, enzymatic, or other appropriate means with a moiety other than a naturally occurring amino acid which contains the insertion and substitution (for example, a detectable moiety such as an enzyme).

The "nucleic acids" or "nucleic acid molecules" of the invention can be DNA or RNA, for example, mRNA. The nucleic acid molecules can be double-stranded or single-stranded; single stranded RNA or DNA can be the coding, or sense, strand or the non-coding, or antisense, strand. Additionally, chemical or enzymatic alteration of expressed nucleic acids and polypeptides may be performed by standard methods. For example, sequences can be modified by addition of phosphate groups, methyl groups, lipids, sugars, peptides, organic or inorganic compounds, by the inclusion of modified nucleotides or amino acids, or the like.

Additionally, the nucleic acids may encode any dehydrogenase as disclosed herein, or an active fragment thereof, as a fusion protein that includes a polypeptide as disclosed herein or an active fragment thereof. For example, the nucleic acids of the invention include polynucleotide sequences that encode dehydrogenases of the invention or active fragments thereof fused to glutathione-S-transferase (GST), poly-histidine (e.g. His$_6$), poly-HN, poly-lysine, hemagglutinin, HSV-Tag or at least a portion of HIV-Tat.

The invention described herein also relates to fragments of the isolated nucleic acid molecules described herein encompassing a portion of a nucleotide sequence described herein which is from at least 20 contiguous nucleotides to at least 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g. nucleic acid molecules which specifically hybridize to a nucleotide sequence encoding polypeptides described herein and encode a dehydrogenase). Hybridization probes include synthetic oligonucleotides which bind in a base-specific manner to a complementary strand of nucleic acid. Suitable probes include polypeptide nucleic acids, as described in Nielsen (1991) *Science*, 254, 1497-1500.

Such nucleic acid molecules can be detected and/or isolated by specific hybridization e.g. under high stringency conditions. "Stringency conditions" for hybridization is a term of art that refers to the incubation and wash conditions, e.g. conditions of temperature and buffer concentration, which permit hybridization of a particular nucleic acid to a second nucleic acid; the first nucleic acid may be perfectly complementary, i.e. 100%, to the second, or the first and second may share some degree of complementarity, which is less than perfect, e.g. 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology (2011) John Wiley & Sons). The exact conditions which determine the stringency of hybridization depend not only on ionic strength, e.g. 0.2×SSC, 0.1×SSC of the wash buffers, temperature, e.g. 23° C., 42° C., 68° C., etc. and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause (1991) *Methods in Enzymology,* 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

The nucleic acid molecules of the invention can optionally comprise additional non-coding sequences such as non-coding 3' and 5' sequences (including, e.g., regulatory sequences) that may be homologous or heterologous to the dehydrogenase gene. Alternatively or in addition, any of the provided nucleic acid molecules can optionally further comprise an additional nucleic acid sequence of at least 50, 60, 70, 80, 90, 100, 150, 200, 250, 300, 350, 400, 450, 500, 550, 600, 700, 800, 900, 1000, or 1500 nucleotides from a photosynthetic organism. The nucleic acid molecules and polypeptides described herein can be used in any of the methods of the invention, and may be included in any of the vectors or recombinant microorganisms of the invention. Nucleic acid molecules comprising sequences that encode dehydrogenases are provided for use in host microorganisms and methods for producing fatty acid products, including free fatty acids, fatty aldehydes, fatty alcohols, fatty acid esters, wax esters, alkanes, alkenes, monoglycerides, diglycerides, and triglycerides.

Nucleic Acid Constructs

The invention also provides constructs comprising a nucleic acid sequence encoding a dehydrogenase or a polypeptide that participates in the production of a lipid that can further include one or more sequences that regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that may be operably linked to the gene of interest (e.g., a dehydrogenase gene) in an expression construct or "expression cassette." The promoter may be regulatable, e.g., inducible.

In aspects where the nucleic acid construct does not contain a promoter in operable linkage with the nucleic acid sequence encoding the gene of interest (e.g., a dehydrogenase gene) the nucleic acid sequence can be transformed into the cells such that it becomes operably linked to an endogenous promoter by, e.g., homologous recombination, site specific integration, and/or vector integration. In some instances, genomic host sequences included in a nucleic acid construct for mediating homologous recombination into the host genome may include gene regulatory sequences, for example, a promoter sequence, that can regulate expression of an dehydrogenase gene of the nucleic acid construct. In such examples, the transgene(s) of the construct can become operably linked to a promoter that is endogenous to the host microorganism. The endogenous promoter(s) may be regulatable, e.g., inducible.

A promoter operably linked to a nucleic acid sequence encoding a dehydrogenase may be a promoter that is heterologous with respect to the dehydrogenase gene. In some embodiments, the promoter may be an inducible promoter, i.e., a promoter that mediates transcription of an operably linked gene in response to a particular stimulus. Such promoters may be advantageous, e.g., to minimize any deleterious effects on the growth of the host cell and/or to maximize production of the fatty acid product. An inducible promoter can be responsive to, e.g., light or dark or high or low temperature, and/or can be responsive to specific compounds. The inducible promoter may be, an ara promoter, a lac promoter, a trp promoter, a tet promoter (e.g., U.S. Pat. No. 5,851,796), a hybrid promoter that includes a portion of a trp, lac, or tet promoter, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689, 044), or the like, or some combination thereof. An inducible promoter can also be responsive to light or dark (U.S. Pat. Nos. 5,750,385, 5,639,952), metals (*Eukaryotic Cell* 2:995-1002 (2003)) or temperature (U.S. Pat. No. 5,447,858; Abe et al. *Plant Cell Physiol.* 49: 625-632 (2008); Shroda et al. *Plant J.* 21: 121-131 (2000)). The foregoing list is exemplary and not limiting. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

For transformation of cyanobacteria, a variety of promoters that function in cyanobacteria can be utilized, including, but not limited to, the ara, lac, tac, and trc promoters, as well as derivatives that are also inducible by the addition of isopropyl β-D-1-thiogalactopyranoside (IPTG) such as the trcY or trcE promoter. Other promoters that may find use in the invention include promoters that are naturally associated with transposon- or bacterial chromosome-borne antibiotic resistance genes (e.g., neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. For example, the promoter(s) can be selected from prokaryotic promoters from a range of species, including eubacterial and cyanobacterial species, such as, for example, an araC or pBAD promoter, a rha promoter, a Pm promoter, a xylS promoter, a nir promoter, a nar promoter, a pho promoter, a tet promoter, a cys promoter, a metallothionien promoter, an ftf promoter, a gln promoter, a heat shock promoter, a cold-inducible promoter or a viral promoter. The foregoing promoters are exemplary and are not limiting. Promoters isolated from cyanobacteria that can be used can include but are not limited to the following: nrs (nickel-inducible), secA (secretion; controlled by the redox state of the cell), rbc (Rubisco operon), psaAB (PS I reaction center proteins; light regulated), psbA (D1 protein of PSII; light-inducible), and the like, and combinations thereof. In some embodiments, the promoters are regulated by nitrogen compounds, such as, for example, nar, ntc, nir or nrt promoters. In some embodiments, the promoters are regulated by phosphate (e.g., pho or pst promoters) or metals, e.g., the nrs promoter (Liu and Curtis (2009) *Proc Natl Acad Sciences USA* 106: 21550-21554), or the petE promoter (Buikema and Haselkorn (2001) *Proc Natl Acad Sciences USA* 98: 2729-2734)). Inducible promoters, as used in the constructs of the present invention, can use one or more portions or domains of the aforementioned promoters and/or other inducible promoters fused to at least a portion of a different promoter that can operate in the host organism, e.g., to confer inducibility on a promoter that operates in the host species.

Likewise, a wide variety of transcriptional terminators can be used for expression vector construction. Examples of possible terminators can include, but are not limited to, psbA, psaAB, rbc, secA, T7 coat protein, and the like, and combinations thereof.

In some embodiments, an isolated or recombinant nucleic acid molecule of the invention can comprise both a nucleic acid sequence that encodes a dehydrogenase and a nucleic acid sequence that encodes a polypeptide that participates in the synthesis of a lipid, e.g., a thioesterase or other lipid production polypeptide. The nucleic acid sequences encoding the dehydrogenase and the lipid production polypeptide may be, for example, any of the nucleic acid sequences described herein. In certain embodiments, the nucleic acid sequence that encodes a dehydrogenase and the nucleic acid sequence that encodes a polypeptide that participates in the production of a lipid can be operably linked to the same promoter and/or enhancer. For example, in particular embodiments the two genes (encoding an dehydrogenase and, for example, a thioesterase) may be organized as an operon, in which, for example, a promoter sequence is followed, in the 5' to 3' direction, by a thioesterase-encoding sequence (or other polypeptide encoding sequence) and then an dehydrogenase-encoding sequence, or vice versa. In any of the above embodiments of operons that include a dehydrogenase gene and a gene encoding a polypeptide for lipid synthesis, one or more additional regulatory sequences can be included in the isolated nucleic acid molecule, for example, a sequence for enhancing translation can be included upstream of any of the gene-encoding sequences, and/or a transcriptional terminator can optionally be included at or near the 3' end of the synthetic operon.

In addition to a dehydrogenase gene and a gene encoding a polypeptide that participates in the production of a lipid, one or more additional genes can optionally be included in a synthetic operon as provided herein, where the one or more additional genes may include, for example, one or more additional genes encoding enzymes or proteins of the fatty acid synthesis or a fatty acid synthesis or lipid synthesis pathway and/or one or more genes encoding enzymes or proteins that may enhance fatty acid product synthesis, one or more genes that may enhance photosynthesis or carbon-fixation, and/or one or more reporter genes or selectable markers.

In some embodiments, the nucleic acid sequence that encodes a dehydrogenase and the nucleic acid sequence that encodes a polypeptide that participates in the production of a lipid can be provided on the same nucleic acid construct where they are operably linked to different promoters and/or transcriptional enhancers. The promoters and enhancers may be, e.g., any of the promoters and transcriptional enhancers described herein.

In certain embodiments, the vector comprising a nucleic acid sequence encoding a dehydrogenase is designed for transformation into cyanobacteria. In a particular embodiment, the vector permits homologous recombination of the dehydrogenase-encoding sequence with the cyanobacterial genome.

An isolated nucleic acid molecule of the present invention can include the sequences disclosed herein that encode a dehydrogenase or other polypeptide in a vector, such as, but not limited to, an expression vector. A vector can be a nucleic acid that has been generated via human intervention, including by recombinant means and/or direct chemical synthesis, and can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism. A vector can be an expression vector that includes one or more specified nucleic acid "expression control elements" that permit transcription and/or translation of a particular nucleic acid in a host cell. The vector can be a plasmid, a part of a plasmid, a viral construct, a nucleic acid fragment, or the like, or a combination thereof.

The vector can be a high copy number vector, a shuttle vector that can replicate in more than one species of cell, an expression vector, an integration vector, or a combination thereof. Typically, the expression vector can include a nucleic acid comprising a gene of interest operably linked to a promoter in an "expression cassette," which can also include, but is not limited to, a transcriptional terminator, a ribosome binding site, a splice site or splicing recognition sequence, an intron, an enhancer, a polyadenylation signal, an internal ribosome entry site, and similar elements. According to some embodiments, the present invention can involve recombinant microorganisms transformed with an isolated nucleic acid comprising a gene of interest under control of a heterologous promoter. Alternatively, if the vector does not contain a promoter operably linked with an isolated nucleic acid comprising a gene of interest, the isolated nucleic acid can be transformed into the microorganisms or host cells such that it becomes operably linked to an endogenous promoter by homologous recombination, site specific integration, and/or vector integration.

In some embodiments, the present invention additionally provides recombinant microorganisms or host cells transformed with an isolated nucleic acid comprising a gene of interest that is operably linked to one or more expression control elements. In some instances, it can be advantageous to express the protein at a certain point during the propagation of the recombinant microorganism, e.g., to minimize any deleterious effects on the growth or proliferation of the recombinant microorganism and/or to maximize production of the triglyceride or fatty acid product of interest. In such instances, one or more exogenous genes introduced into the recombinant microorganism or host cell can be operably linked to an inducible promoter, which mediates transcription of an operably linked gene in response to a particular stimulus.

Transformation vectors can additionally or alternately include a selectable marker, such as, but not limited to, a drug resistance gene, an herbicide resistance gene, a metabolic enzyme and/or factor required for survival of the host (for example, an auxotrophic marker), or the like, or a combination thereof. Transformed cells can be selected based upon the ability to grow in the presence of the antibiotic and/or other selectable marker under conditions in which cells lacking the resistance cassette or auxotrophic marker could not grow. Further, a non-selectable marker may be present on a vector, such as a gene encoding a fluorescent protein or enzyme that generates a detectable reaction product.

Transformation of Microorganisms and Host Cells

A vector comprising an isolated nucleic acid comprising a gene of interest can be introduced into cyanobacteria via conventional transformation and/or transfection techniques. The terms "transformation," "transfection," "conjugation," and "transduction," as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

Host cells such as plants for use in the invention can be transformed by any feasible means, including, without limitation, the use of *Agrobacterium*, particle gun-mediated transformation, laser-mediated transformation, or electroporation. Algae and photosynthetic bacteria can be transformed by any suitable methods, including, as nonlimiting examples, natural DNA uptake (Chung et al. (1998) *FEMS Microbiot Lett.* 164: 353-361; Frigaard et al. (2004) *Methods Mol. Biol.* 274: 325-40; Zang et al. (2007) *J. Microbiol.* 45: 241-245), conjugation (Wolk et al. (1984) *Proc. Natl. Acad. Sci. USA* 81, 1561-1565), transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl. Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly (amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

Methods of Producing Fatty Acid Products

The invention encompasses methods of producing a fatty acid product by culturing the recombinant microorganisms as described herein that include a non-native gene encoding a dehydrogenase under conditions in which the dehydrogenase is expressed and at least one fatty acid product is produced. The methods can further comprise isolating at least one fatty acid product. Expression of the non-native gene encoding a dehydrogenase can optionally be induced during the culturing period. Optionally, at least a portion of the fatty acid and/or fatty acid derivative produced by the recombinant microorganisms can be released or secreted into the growth media by the microorganism.

Also provided herein is a method for producing a lipid comprising culturing a recombinant microorganism that includes a non-native gene encoding a dehydrogenase and at least one non-native gene encoding a polypeptide that participates in the production of a lipid, under conditions in which the non-native gene encoding a dehydrogenase and the at least one gene encoding a polypeptide for the production of a lipid are expressed, to produce a lipid. The methods can further comprise isolating at least one lipid. The lipid can be, for example, a fatty acid product.

In any of the methods provided herein, the culture of the recombinant microorganism that includes a non-native dehydrogenase gene can produce more of the lipid (e.g., fatty acid product) than is produced by a control culture of control microorganism that is identical in all respects to the culture of the recombinant microorganism that includes a non-native dehydrogenase gene except that the control microorganism does not include the non-native gene encoding the dehydrogenase. In any of the methods provided herein, the recombinant microorganism that includes a non-native dehydrogenase gene have a higher propagation and/or proliferation rate that a control microorganism identical in all respects to the recombinant microorganism that includes a non-native dehydrogenase gene except that the control microorganism does not include the non-native gene encoding the dehydrogenase. For example, the culture of the recombinant microorganism that includes a non-native dehydrogenase gene can achieve a higher cell density that is achieved by the control culture after one, two, three, four, five, six, or more than six days of culturing. The recombinant microorganism used in the methods can be a photosynthetic microorganism, and the culturing can be under photoautotrophic conditions, where inorganic carbon is substantially the sole source of carbon for proliferation of the culture and production of the lipid.

In some examples, the lipid (e.g., fatty acid product) that is produced in greater amounts by the recombinant microorganism that includes a non-native dehydrogenase gene and at least one non-native lipid production gene can be a lipid that is not naturally produced by the microorganism, for example, a lipid that is not produced by a microorganism of the same species that lacks the at least one non-native gene that encodes a polypeptide that participates in the production of a lipid, such as a fatty acid product.

Releasing and secreting, as used herein in the context of products of the invention, are used interchangeably to refer to a process by which active and/or passive transport mechanisms allow products of the invention to cross the cell membrane to exit the cell. Examples of such transport mechanisms can include, but are not limited to, gradient diffusion, facilitated diffusion, active transport, and combinations thereof.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the expression of a dehydrogenase gene by lipid-producing cells results in increased cell density of the culture with respect to a culture of lipid producing cells that do not include the non-native dehydrogenase gene.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown heterotrophically, using a reduced carbon source, or mixotrophically, using both light and a reduced carbon source. Additionally or alternately, the microorganism or host cell can be cultured phototrophically. When growing phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic carbon molecule or compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other hydrocarbon constituents can vary and may be optimized to promote growth, propagation, or production of a product such as a lipid. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx) (visited Sep. 20, 2011); Culture Collection of Algae and Protozoa (www.ccap.ac.uk) (visited Sep. 20, 2011); and Katedra Botaniky (botany.natur.cuni.cz/algo/caup-media.html) (visited Sep. 20, 2011).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Table 5), or a modified medium such as ATCC Medium 854 (BG-11 modified to contain vitamin B12) or ATCC Medium 617 (BG-11 modified for marine cyanobacteria, containing additional NaCl and vitamin B 12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation. For example, by using the excess amount of metal (e.g., calcium) in the medium, at least a portion of the fatty acid(s) can be sequestered as soap precipitates, which may result in decreasing the toxic effects of free fatty acid(s). Addition of metal (e.g., calcium) in the medium can additionally or alternately increase the tolerance of microorganism in media with a relatively high concentration of free fatty acids. Additionally or alternately, fatty acid-producing strains can advantageously be more robust with excess metal (e.g., calcium) content. Although the excess component is described herein as a metal, it is contemplated that the component can more generally be described as a carboxylate counterion source, for example a soap-forming counterion source, a metal ion source (noted as "metal" herein), a multivalent (i.e., having a valence of +2 or higher) counterion source, a divalent counterion source, or some combination thereof. Other details regarding this metal/carboxylate counterion source are described in the co-pending, commonly-assigned U.S. patent application Ser. No. 13/324,636, entitled "Culturing a Microorganism in a Medium with an Elevated Level of a Carboxylate Counterion Source", filed on Dec. 13, 2011.

The culture methods can include inducing expression of one or both of a dehydrogenase gene as described and a gene encoding a protein that participates in the production of fatty acid products and triglycerides, and/or regulating metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the recombinant microorganisms or host cells can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use as food, microorganisms or host cells are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Microorganisms and host cells can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pretreat such sources such that the CO level introduced into the (photo)bioreactor do not constitute a dangerous and/or lethal dose with respect to the growth, proliferation, and/or survival of the microorganisms.

The methods include culturing a recombinant microorganism, such as a photosynthetic microorganism, such as, for example, a microalga or cyanobacterium, that includes a non-native gene encoding a dehydrogenase as described herein to produce at least one fatty acid product, in which the method results in production by the culture of at least or about 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 300%, 400%, 500%, 600%, 700%, 800%, 900%, or 1000% more than the amount of the fatty acid product produced by a culture of an otherwise identical microorganism not including the non-native gene encoding the dehydrogenase, cultured under identical conditions. Additionally or alternately, the methods include producing at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, per liter of culture of a fatty acid product by culturing the recombinant microorganisms described herein. Although many times the goal can be to produce and/or recover as much fatty acid product as possible, in some instances the amount of the fatty acid product produced and/or recovered by the method described herein can be limited to about 2 g or less per liter of culture, for example, 1.5 g or less per liter of culture, 1 g or less per liter of culture, 800 mg or less per liter of culture 600 mg or less per liter of culture, for example about 550 mg or less per liter of culture, or about 500 mg or less per liter of culture.

Fatty acid products can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. patent application Ser. No. 13/407,817 entitled "Solvent Extraction of Products from Algae", filed on Feb. 29, 2012, which is incorporated herein by reference in its entirety.

When fatty acid products are sufficiently released or secreted from the microorganisms into the culture medium, the recovery method can be adapted to efficiently recover only the released fatty acid products, only the fatty acid products produced and stored within the microorganisms, or both the produced and released fatty acid products. Fatty acid products secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acid products can then be eluted from the particulate adsorbents, e.g., by the use of an appropriate solvent. In such circumstances, one isolation method can include carrying out evaporation of the solvent, followed by further processing of the isolated fatty acid products, to yield chemicals and/or fuels that can be used for a variety of commercial purposes.

In some examples, the level of a fatty acid product, for example a C8-C24 fatty acid, a C10-C22 fatty acid, or a C12-C18 fatty acid, such as, for example, at least one of a C12, C14, C16, and/or a C18 fatty acid, can be increased in the culture with respect to a culture of an otherwise identical microorganism or host cell, but lacking the non-native dehydrogenase gene. The invention further includes compositions that include free fatty acids, fatty acid derivatives, or glycerolipids produced by the methods of the invention.

Additionally or alternatively, the present invention can include one or more of the following embodiments:

Embodiment 1. A recombinant microorganism comprising a first non-native nucleic acid molecule comprising a nucleotide sequence encoding a dehydrogenase and at least a second non-native nucleic acid molecule comprising a sequence encoding a polypeptide that participates in lipid biosynthesis; wherein a culture of the recombinant microorganism produces a greater amount of a lipid than is produced by a control culture of a microorganism identical in all respects to the recombinant microorganism that includes the first and second non-native nucleotide sequences, except that the control microorganism does not include the first non-native nucleotide sequence encoding a dehydrogenase, wherein the recombinant microorganism has a higher propagation and/or proliferation rate than the control microorganism under conditions in which the lipid is produced.

Embodiment 2. A recombinant microorganism according to embodiment 1, wherein the dehydrogenase is selected from the group consisting of an aldehyde dehydrogenase, acetaldehyde dehydrogenase, alcohol dehydrogenase, glutamate dehydrogenase, glyceraldehyde 3-phosphate dehydrogenase, 2-hydroxyacid dehydrogenase, isocitrate dehydrogenase, lactate dehydrogenase, malate dehydrogenase, methylmalonate semialdehyde dehydrogenase, succinate dehydrogenase, pyruvate dehydrogenase, alpha ketoglutarate dehydrogenase, D-2-hydroxyacid dehydrogenase, D-2-hydroxyisocaproate dehydrogenase, formate dehydrogenase, D-glycerate dehydrogenase, vancomycin-resistant protein H, D-2-photophoglycerate dehydrogenase, D-lactate dehydrogenase, glucose-6-phosphate dehydrogenase, 6-phosphogluconate dehydrogenase, and a sorbitol dehydrogenase, and/or the dehydrogenase comprises an amino acid sequence having at least 50% identity to SEQ ID NO:4, SEQ ID NO:6, SEQ ID NO:7, SEQ ID NO:18, or SEQ ID NO:19, SEQ ID NO:2, SEQ ID NO:29, SEQ ID NO:15, SEQ ID NO:16, SEQ ID NO:10, SEQ ID NO:11, or SEQ ID NO:13.

Embodiment 3. A recombinant microorganism according to embodiment 1 or 2, wherein the polypeptide that participates in lipid biosynthesis is selected from the group consisting of: an acyl-ACP thioesterase, an acyl-CoA thioesterase, a 4-hydroxybenzoyl-thioesterase, a polypeptide having lipolytic activity, an aldehyde-forming acyl-CoA reductase, an aldehyde-forming acyl-ACP reductase, a carboxylic acid reductase, an alcohol-forming acyl-CoA reductase, an alcohol-forming acyl-ACP reductase, a wax synthase, a decarbonylase, a decarboxylase, a GPAT, an LPAAT, a PAP, and a DGAT; further optionally wherein the lipid is a fatty acid product selected from the group consisting of: a free fatty acid, a fatty aldehyde, a fatty alcohol, an alkane, an alkene, a fatty acid ester, a wax ester, a monoacylglyceride, a diacylglyceride, and a triacylglyceride.

Embodiment 4. A recombinant microorganism according to any of the previous embodiments wherein the first non-native nucleic acid molecule comprises:

a nucleotide sequence encoding an aldehyde dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO.:4, SEQ ID NO.:6, or SEQ ID NO.:7;

a nucleotide sequence encoding a methylmalonate semialdehyde dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO:18 or SEQ ID NO:19;

a nucleotide sequence encoding a D-2-hydroxyacid dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO:2 or SEQ ID NO:29;

a nucleotide sequence encoding a D-2-hydroxyacid dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO:15 or SEQ ID NO:16.

a nucleotide sequence encoding a phosphogluconate dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO:10 or SEQ ID NO:11; or a nucleotide sequence encoding a phosophogluconate dehydrogenase that includes an amino acid sequence having at least 50%, at least 55%, at least 60%, at least 65%, at least 70%, at least 75%, at least 80%, at least 85%, at least 90%, at least 95%, or between 95% and 100% identity to SEQ ID NO:13.

Embodiment 5. A recombinant microorganism according to any of the previous embodiments, wherein a culture of the recombinant microorganism that includes a first non-native nucleic acid molecule encoding a dehydrogenase and a second non-native nucleic acid molecule encoding a polypeptide that participates in the production of a lipid produces a greater amount of a lipid than is produced by a control culture of a microorganism identical in all respects to the recombinant microorganism that includes the first non-native nucleotide and the second non-native nucleotide sequence, except that the control microorganism does not include the first non-native nucleotide sequence encoding a dehydrogenase;

wherein the lipid is a fatty acid product not produced by a microorganism of the same species or strain as the recombinant microorganism that does not include the second non-native nucleic acid molecule.

Embodiment 6. A recombinant microorganism according to any of the previous embodiments wherein the recombinant microorganism is a photosynthetic microorganism.

Embodiment 7. A recombinant microorganism according to any of the previous embodiments, wherein the photosynthetic microorganism is a cyanobacterium, optionally selected from the group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus*; or the photosynthetic microorganism is a microalga, optionally selected from the group consisting of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachlorella, Tetraselmis, Thalassiosira, Viridiella,* and *Volvox*.

Embodiment 8. A recombinant photosynthetic microorganism according to embodiment 6 or 7, wherein the expression of the first nucleic acid molecule encoding the dehydrogenase increases the intracellular ratio of NADPH to NADP+ relative to the ratio of NADPH to NADP+ in an otherwise identical microorganism that lacks the first nucleic acid, for example wherein intracellular NADPH/NADP+ ratio about 5% higher, about 10% higher, about 20% higher, about 30% higher, about 40% higher, about 60% higher, about 80% higher, about 100% higher, about 150% higher, about 200% higher, about 300% higher, about 500% higher, about 700% higher, about 900% higher, about 1000% higher, or about 2000% higher than an otherwise identical microorganism lacking the first nucleic acid.

Embodiment 9. A recombinant photosynthetic microorganism according to any of embodiments 6-8, wherein a culture of the recombinant microorganism produces about 1% more, about 5% more, about 10% more, about 20% more, about 30% more, about 40% more, about 50% more, about 60% more, about 70% more, about 80% more, about 90% more, about 100% more, about 200% more, about 500% more, about 700% more, about 1000% more, or about 2000% more of a fatty acid product compared to a culture of an otherwise identical microorganism lacking said first nucleic acid.

Embodiment 10. A recombinant photosynthetic microorganism of any of embodiments 6-9, wherein the recombinant photosynthetic microorganism has a replicative rate about 5% higher, about 10% higher, about 20% higher, about 30% higher, about 40% higher, about 60% higher, about 80% higher, about 100% higher, about 150% higher, about 200% higher, 400% higher, about 600% higher, about 800% higher, about 1000% higher, or at least 2000% higher than an otherwise identical photosynthetic microorganism lacking said first non-native nucleic acid molecule.

Embodiment 11. A method of producing a lipid comprising culturing a recombinant microorganism according to any one of the preceding embodiments in a suitable culture medium for a sufficient amount of time to produce a lipid, optionally wherein the lipid is a fatty acid product selected from the group consisting of a free fatty acid, a fatty aldehyde, a fatty alcohol, an alkane, an alkene, a fatty acid ester, a wax ester, a monoacylglyceride, a diacylglyceride, and a triacylglyceride.

Embodiment 12. A method according to embodiment 11, wherein the recombinant microorganism is a photosynthetic microorganism and the recombinant photosynthetic microorganism is cultured photoautotrophically.

Embodiment 13. A method according to embodiment 11 or 12, wherein the method includes inducing expression of one or both of the nucleic acid encoding the dehydrogenase and the nucleic acid sequence encoding a polypeptide that participates in the production of a lipid.

Embodiment 14. A method according to any of embodiments 11-13, wherein the method further comprises recovering the lipid from the culture.

Embodiment 15. A method of increasing the growth and/or proliferation rate of a microorganism that produces a lipid, wherein the method includes expressing a recombinant nucleic acid molecule that encodes a dehydrogenase in a microorganism that produces a lipid, and culturing the microorganism under conditions that support the growth and/or proliferation of the microorganism, wherein the growth and/or proliferation rate of the microorganism is greater than that of a control microorganism that is cultured under the same conditions and is identical in all respects to the recombinant microorganism, except that the control microorganism does not express a recombinant nucleic acid molecule that encodes a dehydrogenase.

Embodiment 16. A method according to any of embodiments 11-15, wherein the culture reaches a higher optical density after three, four, five, or six days of culture than the culture density reached by an identical culture of a microorganism identical in all respects except that it lacks the non-native gene encoding the dehydrogenase.

Embodiment 17. A cell culture comprising a recombinant microorganism of any one of embodiments 1-10, optionally wherein the recombinant microorganism is a photosynthetic recombinant microorganism and the culture does not include a substantial amount of a reduced carbon source.

Embodiment 18. An isolated nucleic acid molecule comprising a nucleic acid sequence encoding a polypeptide that includes an amino acid sequence having at least 50%, at least 55%, at least 60%, at least 65%, at least 70%, at least 75%, at least 80%, at least 85%, at least 90%, or at least 95% identity to SEQ ID NO:2 or SEQ ID NO:29.

EXAMPLES

Example 1

Screens were designed for identification of genes encoding proteins that were able to enhance fatty acid production by microbes. The Nile Blue screen used an *E. coli* Top 10 strain that carried an N-terminally truncated version of the Cc1FatB1 acyl-ACP thioesterase from *Cuphea carthagenensis* (nucleotide sequence codon-optimized for *Synechocystis*, SEQ ID NO:20, amino acid sequence SEQ ID NO:21; see US 2011/0020883, incorporated by reference herein) as the background for transformation of a metagenomic library containing DNA fragments from an environmental sample removed from a shipping channel in Laguna Madre, Tex. A plate-based assay was used to identify recombinant *E. coli* colonies producing free fatty acids on a solid media that contained 10 μg/mL Nile Blue A (Alfa Aesar, Ward Hill, Mass. #A17174). Nile blue stains fatty acids blue. Colonies were examined by visual inspection for staining by positioning plates on a standard light box. Colonies displaying a high level of Nile Blue A staining over background controls that expressed the CclFatB 1 thioesterase but did not include library fragments were selected, grown up, and further screened to determine the amount of total non-esterified free fatty acid (FFA) using a free fatty acid Detection kit (#SFA-1, Zenbio, Inc, Research Triangle Park, N.C.).

The free fatty acid content of *E. coli* clones exhibiting elevated free fatty acid levels over background controls in the Nile Blue plate assay and subsequently by assay with the free fatty acid detection kit were analyzed further by gas chromatography (GC) with flame ionization detection (GC-FID). Two hundred isolates showing elevated free fatty acid levels in GC-FID analysis over background controls were selected and the nucleotide sequences of the clones were determined. The cloned fragments in these isolates contained from one to at least five open reading frames (potential genes) each, based on bioinformatic analysis of their sequences. Following DNA sequencing and removal of redundant clones, sequences were analyzed again to identify recurring protein domains. Clones denoted "NB" were isolated from the Nile Blue assay. A separate genetic assay for detecting enhanced biosynthesis of fatty acids using a metagenomic library made from isolation of DNA from water samples taken from ponds at Pacific Aquafarms located North of the Salton Sea in southern California was also performed resulting in the isolation of clone B10 (Table 1).

Several clones were identified as having open reading frames encoding polypeptides containing dehydrogenase domains (Table 1). Clones B10 and NB 106 were identified as including sequences encoding D-isomer specific 2-hydroxyacid dehydrogenases; NB8 and NB 112 were identified as encoding aldehyde dehydrogenases; and NB 104 was identified as encoding a 6-phosphogluconate dehydrogenase. Thus, genes encoding three distinct types of dehydrogenase were identified in the cloned fragments isolated in the functional screens.

TABLE 1

Clones selected from Assays.

| Library hit | Pfam | Pfam Annotation, Closest BLAST hit |
|---|---|---|
| B10 | PF02826 | D-isomer specific 2-hydroxyacid dehydrogenase (NAD binding domain) *Polymorphum gilvum* SL003B-26A1 YP_004302702 |
| NB106 | PF00389 | D-isomer specific 2-hydroxyacid dehydrogenase (catalytic domain) *Enterococcus faecalis* ZP_05597403 |
| NB8 | PF00171 | Aldehyde dehydrogenase ywdH *Bacillus thuringiensis* serovar *berliner* ZP_04101108 |
| NB112 | PF00171 | Methylmalonate semialdehyde dehydrogenase *Bacillus amyloliquefaciens* YP_001423238 |
| NB104 | PF000393 | 6-phosphogluconate dehydrogenase *Enterococcus faecalis* TX4248 ZP_07551842 |

The B10 insert included an open reading frame (ORF) (SEQ ID NO:1) encoding a polypeptide (SEQ ID NO:2) that was identified as belonging to Pfam 02826 ("D-isomer specific 2-hydroxyacid dehydrogenase, NAD binding domain", gathering cutoff, 25.1) with a bit score of 159.3 and an e value of 4.2 e-47. The B10 ORF encodes a polypeptide having an amino acid sequence that is 64% identical to the D-isomer specific 2-hydroxyacid dehydrogenase, NAD-binding protein of *Polymorphum gilvum* SL003B-26A1 (Gene ID: 328542593; accession YP_004302702); 57% identical to the D-isomer specific 2-hydroxyacid dehydrogenase of *Labrenzia alexandrii* DFL-11 (Gene ID: 254503433; accession ZP_05115584); 56% identical to the 2-hydroxyacid dehydrogenase of *Stappia aggregata* IAM126114 (Gene ID: 118438963; accession ZP_01545666); and 55% identical to the D-isomer specific 2-hydroxyacid dehydrogenase (NAD-binding) of *Marinomonas* sp. MWYL1 (Gene ID: 5367846; accession YP_001342133). The first twelve amino acids of the B10 ORF (SEQ ID NO:2) were upstream of a methionine that is the first amino acid of the *Polymorphum gilvum* D-isomer specific 2-hydroxyacid dehydrogenase, NAD-binding protein, thus these amino acids may not be part of the native protein encoded by the B10 ORF: the encoded polypeptide is likely to comprise amino acids 13-326 of SEQ ID NO:2. SEQ ID NO:29 represents amino acids 13-326 of SEQ ID NO:2.

The NB 106 insert included an open reading frame (SEQ ID NO:14) that encoded a polypeptide (SEQ ID NO:15) identical to amino acids 1-137 of as the D-isomer specific 2-hydroxyacid dehydrogenase of *Enterococcus faecalis* (ZP_05597403; SEQ ID NO:16) This polypeptide sequence recruited to Pfam PF00389 ("D-isomer specific 2-hydroxyacid dehydrogenase, catalytic domain", gathering cutoff, 24.6) with a bit score of 57.6 and an e value of 7.8 e-16. Additional D-isomer specific 2-hydroxyacid dehydrogenases having homology to the polypeptide encoded by the NB106 ORF (SEQ ID NO:14) include the D-isomer specific 2-hydroxyacid dehydrogenase of *Enterococcus gallinarum* EG2 (ZP_05648199; EEV31532) (79% identity); the D-isomer specific 2-hydroxyacid dehydrogenase of *Enterococcus casseliflavus* ATCC 12755 (ZP_08145011; EGC69912) (78% identity); the D-isomer specific 2-hydroxyacid dehydrogenase of *Carnobacterium* sp. AT7 (ZP_02185893; EDP67348) (72% identity); the D-isomer specific 2-hydroxyacid dehydrogenase of *Enterococcus faecium* E1636 (ZP_06695345; EFF23321) (78% identity); the 2-hydroxyacid dehydrogenase of *Pediococcus acidilactici* 7_4 (ZP_06196181; EFA27324) (63% identity); the 2-hydroxyacid dehydrogenase of *Lactobacillus brevis* ATCC 367 (YP_794343; ABJ63312) (63% identity); the 2-hydroxyacid dehydrogenase of *Lactobacillus coleohominis* 101-4-CHN (ZP_05553013; EEU30233) (64% identity); and the D-isomer specific 2-hydroxyacid dehydrogenase of *Clostridium beijerinckii* NCIMB 8052 (YP_001309316.1 GI:150017062) (75% identity).

The NB8 insert or included an ORF (SEQ ID NO:3) encoding a polypeptide (SEQ ID NO:4) that was identified as belonging to Pfam 00171 ("aldehyde dehydrogenase", gathering cutoff, 23.0) with a bit score of 280.5 and an e value of 1.4 e-83. The ORF, which begins at the 5'-most end of the insert, has at least 99% identity to amino acids 95-455 of a *Bacillus thuringiensis serovar thuringiensis* aldehyde reductase (Gene ID: 118438963; accession ZP_01432004; SEQ ID NO:7). NB8 appears to encode a truncated *Bacillus* aldehyde reductase, as the ORF is missing amino acids homologous to the N-terminal-most 90-100 amino acids of the *Bacillus thuringiensis aldehyde reductase* (SEQ ID NO:7). Further, due to a cloning error that was not realized when the expression experiments were performed, only a subportion of this ORF was cloned into the integration vector for expression in *Synechocystis*. Amino acids N-terminal to amino acid 95 and C-terminal of amino acid 347 of SEQ ID NO:7 (the *Bacillus* aldehyde dehydrogenase) therefore do not appear to be required for activity, as expression of the NB8 partial ORF (SEQ ID NO:5), which encodes a polypeptide (SEQ ID NO:6) that lacks 94 amino acids of the N-terminal and 108 amino acids of the C-terminal of the *Bacillus* aldehyde dehydrogenase, demonstrated effects on proliferation and fatty acid productivity (see Example 2). Other *Bacillus* aldehyde dehydrogenases including amino acid sequences having sequence homology to SEQ ID NO:4 include the ywdH aldehyde dehydrogenase of *Bacillus thuringiensis serovar berliner* (Gene ID: 228938499; accession ZP_041501108) (99% identity); the ywdH aldehyde dehydrogenase of *Bacillus thuringiensis* IBL 200 (Gene ID: 228907013; accession ZP_04070879) (98% identity); the aldehyde dehydrogenase (NAD) family protein of *Bacillus thuringiensis* IBL 4222 (Gene ID: 228899962; accession ZP_04064201) (98% identity); the aldehyde dehydrogenase ywdH of *Bacillus thuringiensis servovar kurstaki* (Gene ID: 228951764; ZP_04113863) (98% identity), the aldehyde dehydrogenase ywdH of *Bacillus cereus* ATCC 10876 (Gene ID: 229189465; ZP_04316482) (98% identity), the aldehyde dehydrogenase ywdH of *Bacillus thuringiensis serovar huazhongensis* (Gene ID: 228920096; ZP_04083445) (98% identity), the aldehyde dehydrogenase (NAD) family protein of *Bacillus cereus* (Gene ID: 206967852; ZP_03228808) (98% identity), and the aldehyde dehydrogenase ywdH of *Bacillus cereus* 172560W (Gene ID: 229177791; ZP_04305164) (97% identity). Aldehyde dehydrogenases that include amino acid sequences having at least 50% identity to SEQ ID NO:4 include the aldehyde dehydrogenase of *Bacillus cytotoxicus* NVH 391-98 (Gene ID: 5344056; YP_001374327) (82% identity); the aldehyde dehydrogenase of *Bacillus megaterium* WSH-002 (Gene ID: 345444973; gb AEN89990) (62% identity); aldehyde dehydrogenase ywdH of *Bacillus mycoides* Rock3-17 (Gene ID: 228996488 ZP_04156127) (81% identity), aldehyde dehydrogenase ywdH [*Bacillus cereus* AH621 (gi 229166217; ZP_04293977) (89% identity), and the aldehyde dehydrogenase (NAD(P)$^+$) of *Bacillus thuringiensis* str. Al Hakam (gi 118476858; YP_894009) (90% identity).

The NB 112 insert included an open reading frame (SEQ ID NO:17) that encoded a portion of a polypeptide (SEQ ID NO:18) having 98% identity to the methylmalonate semialdehyde dehydrogenase of *Bacillus amyloliquefaciens* (YP_001423238; SEQ ID NO:19). This polypeptide sequence recruited to Pfam PF00171 ("aldehyde dehydrogenase", gathering cutoff, 23.0) with a bit score of 203.7 and an e value of 3 e-60. Additional methylmalonate semialdehyde dehydrogenases having homology to the polypeptide encoded by the NB 112 ORF (SEQ ID NO:18) include the methylmalonate semialdehyde dehydrogenase of *Bacillus atrophaeus* 1942 (YP_003975426; ADP34495) (92% identity); the methylmalonate-semialdehyde dehydrogenase of *Bacillus licheniformis* ATCC 14580 (YP_081323; gi 52082532) (89% identity); the methylmalonate-semialdehyde dehydrogenase *Paenibacillus dendritiformis* C454 (ZP_09676636) (84% identity); the methylmalonate-semialdehyde dehydrogenase of *Paenibacillus terrae* HPL-003 (YP_005075546; AET59323) (83% identity); the methylmalonate-semialdehyde dehydrogenase of *Bacillus clausii* KSM-$K_{16}$ (YP_173925; BAD62964) (80% identity); the methylmalonate-semialdehyde dehydrogenase of *Listeria monocytogenes* FSL F2-208 (EFR85827) (79% identity); the methylmalonate-semialdehyde dehydrogenase of *Listeria marthii* FSL S4-120 (ZP_07869657; EFR88847) (79% identity); and the methylmalonate-semialdehyde dehydrogenase of *Alicyclobacillus acidocaldarius* LAA1 (ZP_03495181; EED06125) (70% identity).

The NB 104 insert (SEQ ID NO:8) included an open reading frame (SEQ ID NO:9) that encoded a polypeptide (SEQ ID NO:10) identified as a portion of a 6-phosphogluconate dehydrogenase of *Enterococcus faecalis* (e.g., ZP_0521253; SEQ ID NO:11). This polypeptide sequence recruited to Pfam 00393 ("phosphogluconate dehydrogenase", gathering cutoff, 20.4) with a bit score of 55.4 and an e value of 4.4 e-15. The NB 104 open reading frame encodes a polypeptide having 100% identity to amino acids 13-311 of the *Enterococcus faecalis* 6-phosphogluconate dehydrogenase (SEQ ID NO:11). Additional 6-phosphogluconate dehydrogenases having homology to the polypeptide encoded by the NB 104 ORF (SEQ ID NO:10) include the 6-phosphogluconate dehydrogenase of *Carnobacterium* sp. AT7 (Gene ID: 163791487; ZP_02185894; 56% identity), the 6-phosphogluconate dehydrogenase of *Anaerococcus vaginalis* ATCC 51170 (Gene ID: 256546044; ZP_05473398; 51% identity), the 6-phosphogluconate dehydrogenase of *Enterococcus casseliflavus* (Gene ID: 257867259; ZP_05646912; 51% identity), and the 6-phosphogluconate dehydrogenase-like protein of *Clostridium beijerinckii* NCIMB 8052 (Gene ID: 150017061; YP_001309315; 49% identity).

Example 2

Cloned DNA fragments of several of the sequenced clones, including NB8, NB104, and B10 strain (under the control of the IPTG-inducible trcY promoter (SEQ ID NO:22)), were subsequently transformed into a *Synechocystis* PCC 6803 that included an integrated Cc1FatB1 acyl-ACP thioesterase gene at a different locus.

The N-terminally truncated Cc1FatB1 acyl-ACP thioesterase gene (SEQ ID NO:20) was cloned into *Synechocystis* integration vector YC28 (SEQ ID NO:23) which included a PISA origin of replication for *E. coli*, "RS1 up" (SEQ ID NO:24) and "RS1 down" (SEQ ID NO:25) fragments for homologous recombination in *Synechocystis* 6803, a lacIQ repressor for the IPTG-inducible trcE driven *Cuphea* Cc1FatB1 thioesterase gene and a kanamycin resistance marker for selection. DNA source material for PCR amplification of segments of the vector came from *Synechocystis* genomic DNA, a pUC-19 vector, a pACYC-184 vector, and a vector containing a synthesized *Cuphea* Cc1FatB1 gene (DNA2.0, Menlo Park).

Expression vectors were also constructed for overexpressing the fragments identified as having sequences encoding dehydrogenases (or portions thereof) by the functional screen described in Example 1. The B10 ORF (SEQ ID NO:1), the NB104 contig fragment (SEQ ID NO:8), and the NB104 ORF (SEQ ID NO:9), were independently amplified from the "contig" clones identified in the library screen using primers which contained around 15 bp of sequence homologous with cyanobacterial integration vector pSGI-YC63 (SEQ ID NO:28). An NB8 partial ORF fragment (SEQ ID NO:5) was also cloned in the pSGI-YC63 integration vector. pSGI-YC63 contained a spectinomycin marker for selection, homologous "RS2 up" (SEQ ID NO:26) and "RS2 down" (SEQ ID NO:27) arms for integration in the RS2 site of *Synechocystis*, the lacIQ repressor to regulate the trcY promoter (SEQ ID NO:22), and a pUC origin of replication for *E. coli* propagation.

To introduce the Cc1FatB1 acyl-ACP thioesterase gene construct and the dehydrogenase ORF constructs into cyanobacteria, *Synechocystis* sp. PCC 6803 cells were cultured in BG-11 media, which does not include a substantial amount of a reduced carbon source, to an OD (730 nm) of about 0.7-0.9. About 10 mL of the culture was spun down at approximately 2000 g for 15 minutes, and the cell pellet was resuspended in 1 mL fresh BG-11 media. An aliquot of 300 µL of cells was transformed with about 100 ng of integration vector. The cells were incubated under lights (80 µE) for about 6 hours, then spread onto Minipore filters and placed on top of BG-11 agar plates containing no antibiotics. The plates were incubated at about 30° C. under about 80 µE of light for about 24 hours. The filters were then transferred onto fresh BG-11 1.5% agar plates with 20 µg/mL kanamycin and cultured for 7 days. Colonies of *Synechocystis* sp. PCC 6803 were picked and patched onto new agar plates. The putative dehydrogenase-encoding constructs for integration into the *Synechocystis* genome were transformed into Cc1FatB1-transformed strains using the same procedure, except that antibiotic selection included 20 µg/mL spectinomycin in addition to 20 µg/mL kanamycin.

Cultures that included the Cc1FatB1 acyl-ACP thioesterase gene and a dehydrogenase-encoding open reading frame were grown at about 60 uE of light with constant shaking and 1% $CO_2$. OD at the time of induction was 0.6. Cultures were induced with 1 mM IPTG. The strains were grown in 4 mL glass vials with an initial volume of 1.5 mL. At the end of 6 days, the entire vial with about 1 mL of culture remaining in the vial (due to evaporative loss) was submitted for gas chromatography. A strain with the CcFatB1 thioesterase gene (under the control of the TrcY promoter) integrated into the RS2 site of 6803 but not carrying an exogenous dehydrogenase gene served as the control.

Free fatty acids were analyzed by gas chromatography (GC) with flame ionization detection (GC-FID). 1 mL cultures in 4 mL vials capped with PTFE (polytetrafluoroethylene)-lined caps (National Scientific) were submitted to Analytical for analysis. Eighty four microliters of an internal standard (I.S.) set that included the free fatty acids C9:0, C13:0, and C17:0, each at a concentration of 600 µg/ml, in hexane, were added to the culture sample, followed by 83 microliters of 50% $H_2SO_4$, 167 microliters of 5M NaCl, and 1.4 milliliters of hexane. The final concentration of each I.S. was 50 µg/ml relative to sample volume. The fatty acids for making the I.S. set were purchased from Fluka or Nu-Chek Prep, Inc. Three I.S.'s were used given the variable response of the free fatty acids. C8:0 and C10:0 were calibrated w/C9:0 I.S.; C12:0 and C14:0 used the C13:0 I.S.; and the remaining C16:0 through C18:2 cis-9,12 used the C17:0 I.S. Post reagent and I.S. addition, the cultures were vortexed on a multi-tube vortexer at 2,500 rpm for 30 min. The vials were finally centrifuged for 3 min. at 2500 rpm to provide good separation between organic and aqueous phases. The hexane layers were sampled by a Gerstel MPS2L Autosampler. Fatty acid samples were analyzed on an Agilent model 7890A gas chromatograph equipped with an FID (flame ionization detector) that included a J&W Scientific DB-FFAP capillary column (10 m length, 0.10 mm internal diameter, 0.10 µm film thickness). The GC oven was programmed as follows: 120° C. for 0.1 min., then heated at 40° C./min. to 240° C. (hold 3 minutes). The injector temperature was kept at 250° C., and a 40:1 split 1.0 µl injection was used. Hydrogen was used as a carrier gas at a flow rate of 0.5999 ml/min. The FID was set to 320 C. The analytes were identified by comparison of retention times to individually injected standards. The calibration range for the analytes was 2.5 µg/ml to 200 µg/ml for C8:0-C16:1 fatty acids and 0.625 µg/ml to 50 µg/ml for C18:0-C18:2 fatty acids. The limit of quantitation for each analyte was the lowest concentration listed in the calibration range except C18:0, C18:1 cis9 (1.25 ug/mL) and C18:2 cis-9,12 (2.5 ug/mL). Spiking and recovery experiments into whole cell culture showed that the extraction method recovered consistently within a range of 85%-115% for each analyte in this sample batch run except C16:1 cis9 (74%), C18:1 cis9 (63%), and C18:2 cis-9,12 (64%).

Figure 2:
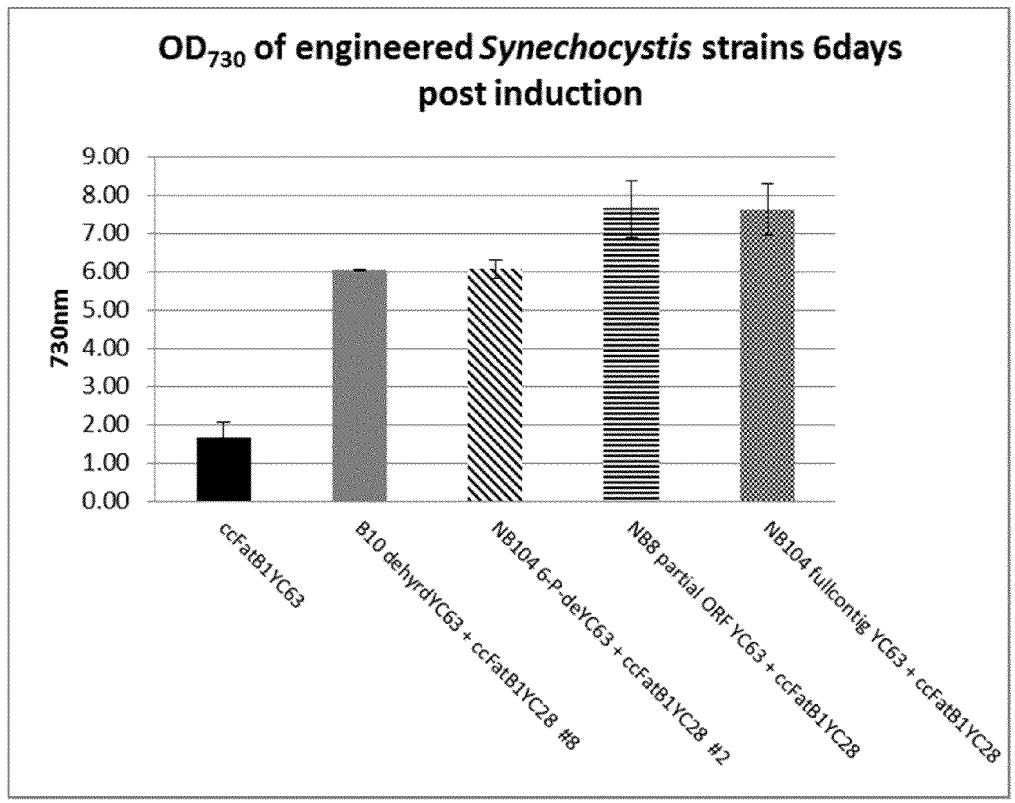
FIG. 2 depicts optical densities of engineered *Synechocystis* PCC6803 strains at the end of six days of growth. All the strains were induced with 1 mM IPTG to express the Cc1FatB1 acyl-ACP thioesterase gene and a dehydrogenase gene. The black bar represents the strain expressing acyl-ACP thioesterase alone. The patterned bars represent strains that contained isolated genes identified as dehydrogenases along with the acyl-ACP thioesterase gene.

The total amount of free fatty acid produced by these engineered *Synechocystis* strains is provided in FIG. 1. It can be seen that *Synechocystis* strains expressing the B10 ORF ("dehydrd"; SEQ ID NO:1), the NB8 partial ORF fragment (SEQ ID NO:5), the NB104 ORF ("6-P-de"; SEQ ID NO:9), and NB104 ORF full contig fragment (SEQ ID NO:8) along with Cc1FatB1 thioesterase encoding sequence (SEQ ID NO:20) produced higher levels of free fatty acids as compared to the control strain that contained the Cc1FatB1 thioesterase gene alone. FIG. 2 demonstrates that in this experiment strains that included a Cc1FatB 1 thioesterase and a dehydrogenase gene obtained from the screen were able to achieve culture that were four to five-fold higher than the cell density of the strain that expressed Cc1FatB1 thioesterase, but lacked a dehydrogenase gene.

Example 3

To further investigate the effects of expressing genes that enhanced fatty acid production, *Synechocystis* strains engineered to express the B10 (2-hydroxyacid dehydrogenase NAD-binding domain protein) gene and the NB 104 (6-phosphogluconate dehydrogenase) gene together with a Cc1FatB1 acyl-ACP thioesterase gene were assessed for their ability to alter the redox state of the cells. As a control, the Cc1FatB1 gene integrated at the RS2 site integration vector pSGI-YC63 (1A/YC63) was expressed in independent *Synechocystis* 6803 strains that did not have an additional dehydrogenase gene. *Synechocystis* 6803 having no transgenes ("6803") was included as a further control. Cells were grown under constant light at 60 uE with shaking, and induced with the addition of 1 mM IPTG at an $OD_{730}$ of 0.5 to express the thioesterase and, where present, the putative dehydrogenase. Samples were collected every 24 hours for three days.

To determine the redox state of the *Synechocystis* strains engineered with the dehydrogenase genes and the control strains, enzymatic assays were performed to determine NADPH/NADP+ ratios on samples taken at 1, 2, and 3 days post induction. An NADP/NADPH Quantitation Kit (BioVision, Inc., Mountain View, Calif.) was used for this purpose. The enzymes in the assay kit specifically recognize NADP+/NADPH in an enzyme cycling reaction. For the assay, approximately 1.5×107 cells for each time point were lysed in 1 ml of NADPH extraction buffer provided with the assay kit. The cells were subjected to 2 freeze/thaw cycles in liquid nitrogen and 4 rounds of bead beating. The lysate was then centrifuged and the supernatant was filtered over a 10K cutoff column. All photosynthetic pigments and enzymes that might consume NADPH were retained on the filter membrane. The filtrate consisted of only small metabolites and was used in the NADPH assay. The assay kit enabled the measurement of total NADP (NADP+ plus NADPH) and NADPH. The NADPH/NADP+ ratio was determined by subtracting the amount of NADPH from the total NADP to provide the amount of NADP+, and then to divide the amount of NADPH by the calculated amount of NADP+.

Figure 3:
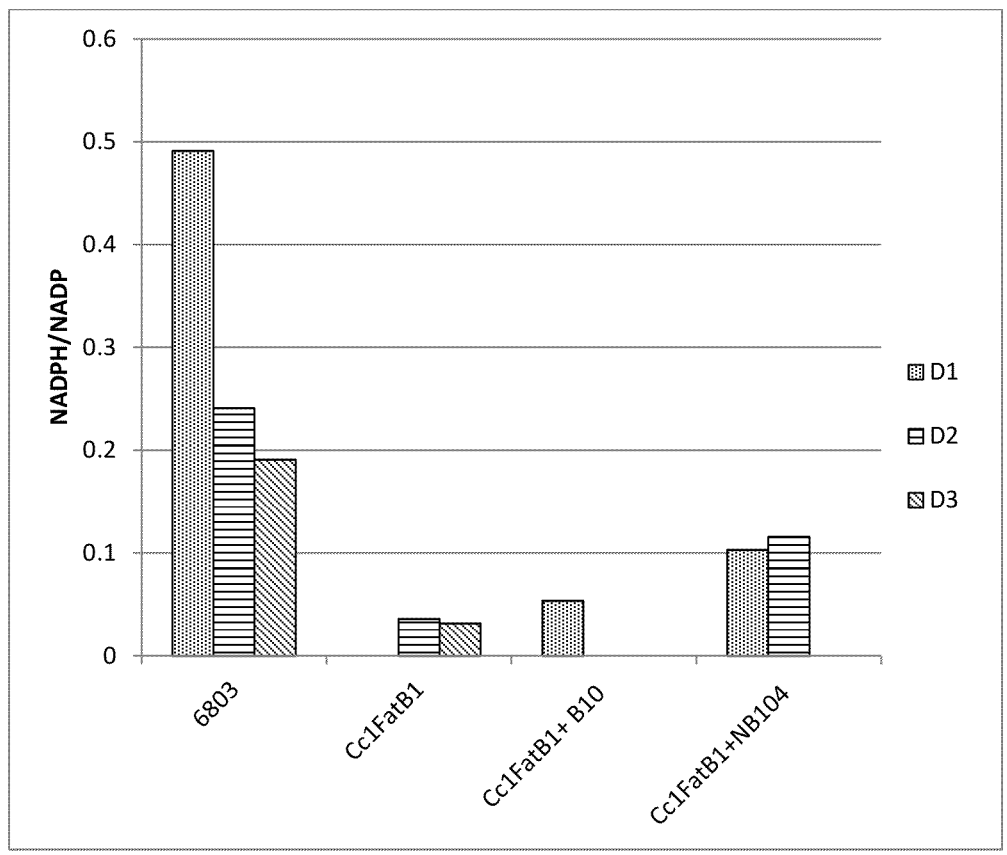
FIG. 3 depicts the redox state of wild type (WT) and engineered *Synechocystis* strains. NADPH/NADP+ ratios are shown for WT *Synechocystis* strain ("6803"), the acyl-ACP thioesterase expressing strain (Cc1FatB1) and strains co-expressing the Cc1FatB1 thioesterase gene and a dehydrogenase gene (Cc1FatB1+B10; Cc1FatB1+NB104). D stands for the number of days in culture.

Assay results are summarized in FIG. 3. FIG. 3 shows the ratio of NADPH to NADP+ on successive days of the experiment. In the control strain, wild-type Synechocystis PCC 6803, NADPH declines with respect to NADP+ with each additional day in culture. The strain expressing an exogenous acyl-ACP thioesterase, Cc1FatB1, shows a marked decline in the ratio of NADPH to NADP+ when compared with the wild-type cells. This was expected as the fatty acid biosynthesis process is known to require extensive reducing power. Addition of a dehydrogenase gene to a strain expressing a foreign acyl-ACP thioesterase, however, increased the ratio of NADPH to NADP+, with the NB104 (6-phosphogluconate dehydrogenase) gene having a greater effect on the NADPH/NADP+ ratio than the B 10 (2-hydroxyacid dehydrogenase NAD-binding domain protein) gene in this experiment. While the ratio of NADPH to NADP+ is not restored to wild type levels, it is at least 2-fold higher than the strains expressing the acyl ACP thioesterase alone.

Figure 4:
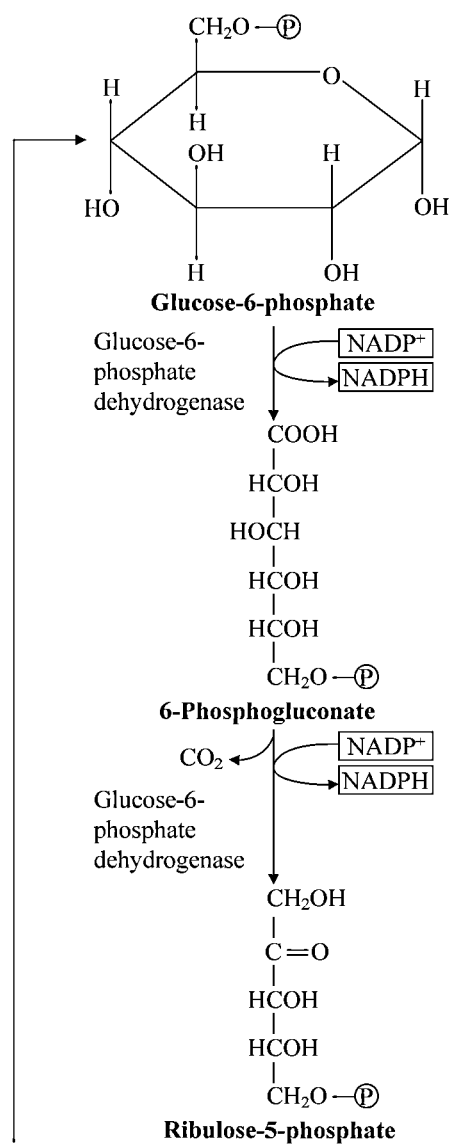
FIG. 4 depicts a portion of the pentose phosphate pathway that produces NADPH showing the 6-phosphogluconate dehydrogenase gene.

Expression of the B10 ORF or the NB 104 ORF in Synechocystis 6803 along with Cc1FatB 1 thioesterase therefore increased the NADPH/NADP+ ratio of cells (FIG. 3), allowed for higher proliferation rates of strains as measured by culture density at six days (FIG. 2), and also led to higher production of free fatty acids of all chain lengths (FIG. 1). The NB104 ORF encodes a portion of a 6-phosphogluconate dehydrogenase, an enzyme of the pentose phosphate pathway (FIG. 4). This pathway produces 5C sugars, used in nucleotide and nucleic acids biosynthesis, from 6C sugars. The pentose phosphate pathway helps in generation of reducing equivalents in the form of NADPH which is use for reductive biosynthesis reactions within the cells such as fatty acid biosynthesis.

Example 4

Figure 5:
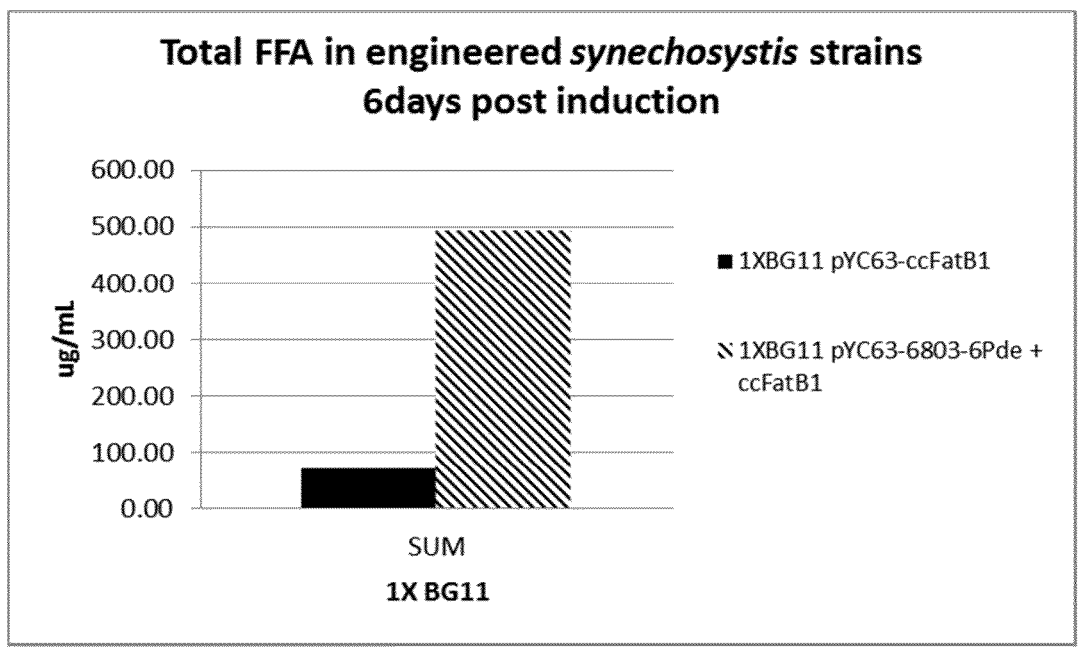
FIG. 5 depicts free fatty acid (FFA) production by *Synechocystis* strains expressing the CcFatB1 acyl-ACP thioesterase gene (black bar), or co-expressing the Cc1FatB1 acyl-ACP thioesterase gene and the *Synechocystis* 6-phosphogluconate dehydrogenase sll0329 gene (SEQ ID NO:12) (patterned bar) six days after inducing expression of the transgenes. Strains were induced at $OD_{730}$=5.0.

The NB 104 ORF from a metagenomic library encoded a portion of an Enterococcus 6-phosphogluconate dehydrogenase. Overexpression of the 6-phosphogluconate dehydrogenase enzyme gene (SEQ ID NO:12) from Synechocystis sp. PCC 6803 was also tested to determine if it would exert the same effect as the Enterococcus-derived 6-phosphogluconate dehydrogenase gene. The Synechocystis 6-phosophogluconate dehydrogenase gene sll0239 (Accession BAA10105; GI:1001479; SEQ ID NO:12) was therefore cloned into a YC63 construct in which it was placed under the control of the trcY promoter and integrated into the RS2 site of a Synechocystis strain expressing the Cc1FatB1 acyl-ACP thioesterase gene regulated by the trcE promoter (SEQ ID NO:30) and integrated at the RS1 site. The resulting strain was tested for fatty acid production along with a control Synechocystis sp. PCC 6803 strain that only expressed the acyl-ACP thioesterase gene from a trcY promoter (integrated at the RS2 site). In this experiment, strains were induced after they had reached a high density to attain greater levels of free fatty acid production. Briefly, 5.0 OD equivalent cells were spun down and resuspended in fresh BG11 media containing 1 mM IPTG and appropriate antibiotics. The final culture volume was 1.5 ml. These strains were grown in a 4 mL glass vial with constant shaking, a light intensity of 60uE and 1% $CO_2$. In this example, in which cells were induced at a relatively high density and cultured for 6 days under induction, expression of the homologous Synechocystis dehydrogenase gene also increased the amount of free fatty acids (FIG. 5). Fatty acid analysis of the samples was performed as in Example 2.

The native Synechocystis 6-phosphogluconate dehydrogenase enzyme increased the FFA by at least two-fold as compared to strains expressing the Cc1FatB1 thioesterase alone (FIG. 5). The patterned bar represents the native Synechocystis 6803 6-phosphogluconate dehydrogenase enzyme cloned in Synechocystis along with Cc1FatB1. We therefore conclude that overexpression of an NADPH producing dehydrogenase such as 6-phosphogluconate dehydrogenase in organisms, including photosynthetic microorganisms cultured photoautotrophically (without a reduced carbon source supporting growth or proliferation of the culture), improves the proliferation rate and also enhances the overall yield of free fatty acid by the culture.

The Summary and Abstract sections may set forth one or more but not all exemplary embodiments of the present invention as contemplated by the inventor(s), and thus, are not intended to limit the present invention and the appended claims in any way.

The foregoing description of the specific embodiments will reveal the general nature of the invention that others can, by applying knowledge within the skill of the art, readily modify and/or adapt for various applications such specific embodiments, without undue experimentation and without departing from the general concept of the present invention. Therefore, such adaptations and modifications are intended to be within the meaning and range of equivalents of the disclosed embodiments, based on the teaching and guidance presented herein, and the breadth and scope of the present invention should not be limited by any of the above-described exemplary embodiments.

What is claimed is:

1. A method of culturing a lipid-producing photosynthetic microorganism comprising:
providing a culture of a recombinant photosynthetic microorganism that comprises a non-native gene encoding a dehydrogenase and at least one non-native gene encoding a thioesterase in a suitable culture medium under conditions in which the non-native gene encoding the dehydrogenase and the non-native gene encoding the thioesterase are expressed,
wherein the culture produces a greater amount of the lipid than does a culture comprising a control microorganism identical in all respects except that it does not include the gene encoding a non-native dehydrogenase,
further wherein the recombinant photosynthetic microorganism that comprises the non-native gene encoding a dehydrogenase has a higher growth and/or proliferation rate than the control microorganism that lacks the gene encoding the non-native dehydrogenase.

2. The method of claim 1, wherein the dehydrogenase is an NADP-dependent dehydrogenase.

3. The method of claim 1, wherein the dehydrogenase is an aldehyde dehydrogenase, a methylmalonate semialdehyde dehydrogenase, a non-phosphorylating glyceraldehyde-3-phosphate dehydrogenase, a D-2-hydroxyacid dehydrogenase, a glucose-6-phosphate dehydrogenase, a 6-phosphogluconate dehydrogenase, an isocitrate dehydrogenase, or a malic enzyme.

4. The method of claim 3, wherein the dehydrogenase is an aldehyde dehydrogenase.

5. The method of claim 4, wherein the aldehyde dehydrogenase comprises an amino acid sequence having at least 70% sequence identity to SEQ ID NO:4.

6. The method of claim 5, wherein the aldehyde dehydrogenase comprises an amino acid sequence having at least 85% sequence identity to SEQ ID NO:4.

7. The method of claim 3, wherein the dehydrogenase is a methylmalonate semialdehyde dehydrogenase.

8. The method of claim 7, wherein the methylmalonate semialdehyde dehydrogenase comprises an amino acid sequence having at least 70% sequence identity to an amino acid sequence selected from the group consisting of SEQ ID NO:18 and SEQ ID NO:19.

9. The method of claim 8, wherein the methylmalonate semialdehyde dehydrogenase comprises an amino acid sequence having at least 85% sequence identity to an amino acid sequence selected from the group consisting of SEQ ID NO:18 and SEQ ID NO:19.

10. The method of claim 3, wherein the dehydrogenase is a D-2-hydroxyacid dehydrogenase.

11. The method of claim 10, wherein the D-2-hydroxyacid dehydrogenase comprises an amino acid sequence having at least 70% sequence identity to an amino acid sequence selected from the group consisting of SEQ ID NO:2, SEQ ID NO:29, SEQ ID NO:15, and SEQ ID NO:16.

12. The method of claim 11, wherein the D-2-hydroxyacid dehydrogenase comprises an amino acid sequence having at least 85% sequence identity to an amino acid sequence selected from the group consisting of SEQ ID NO:2, SEQ ID NO:29, SEQ ID NO:15, and SEQ ID NO:16.

13. The method of claim 3, wherein the dehydrogenase is a 6-phosphogluconate dehydrogenase.

14. The method of claim 13, wherein the a 6-phosphogluconate dehydrogenase comprises an amino acid sequence having at least 70% sequence identity to an amino acid sequence selected from the group consisting of SEQ ID NO:10, SEQ ID NO:11, and SEQ ID NO:13.

15. The method of claim 14, wherein the a 6-phosphogluconate dehydrogenase has at least 85% sequence identity to an amino acid sequence selected from the group consisting of SEQ ID NO:10, SEQ ID NO:11, and SEQ ID NO:13.

16. The method of claim 13, wherein the 6-phosphogluconate dehydrogenase is endogenous to the recombinant photosynthetic microorganism.

17. The method of claim 1, wherein the recombinant photosynthetic microorganism is a microalga.

18. The method of claim 17, wherein the recombinant photosynthetic microorganism is a species of an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, or *Volvox*.

19. The method of claim 1, wherein the recombinant photosynthetic microorganism is a cyanobacterium.

20. The method of claim 1, wherein the recombinant photosynthetic microorganism is a species of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, The rmosynechococcus, Tolypothrix, Trichodesmium, Tychonema* or *Xenococcus*.

21. The method of claim 1, wherein the recombinant photosynthetic microorganism is cultured photoautotrophically.

22. A recombinant photosynthetic microorganism comprising a first non-native gene encoding a dehydrogenase, wherein the photosynthetic microorganism further comprises at least a second non-native gene encoding a thioesterase;
wherein the photosynthetic microorganism produces a lipid;
further wherein the photosynthetic microorganism has a higher growth and/or proliferation rate than an otherwise identical microorganism that lacks the non-native gene encoding a dehydrogenase.

23. The recombinant photosynthetic microorganism of claim 22, wherein the lipid is a fatty acid, a fatty acid derivative, or a triglyceride.

24. The recombinant photosynthetic microorganism of claim 22, wherein the dehydrogenase is an NADP-dependent dehydrogenase.

25. The recombinant photosynthetic microorganism of claim 24, wherein the dehydrogenase is an aldehyde dehydrogenase, a methylmalonate semialdehyde dehydrogenase, a non-phosphorylating glyceraldehyde-3-phosphate dehydrogenase, a D-2-hydroxyacid dehydrogenase, a glucose-6-phosphate dehydrogenase, 6-phosphogluconate dehydrogenase, an isocitrate dehydrogenase, or a malic enzyme.

26. The recombinant photosynthetic microorganism of claim 25, wherein the dehydrogenase is an aldehyde dehydrogenase.

27. The recombinant photosynthetic microorganism of claim 26, wherein the aldehyde dehydrogenase comprises an amino acid sequence having at least 70% identity to SEQ ID NO:4.

28. The recombinant photosynthetic microorganism of claim 27, wherein the aldehyde dehydrogenase comprises an amino acid sequence having at least 85% identity to SEQ ID NO:4.

29. The recombinant photosynthetic microorganism of claim 25, wherein the dehydrogenase is a methylmalonate semialdehyde dehydrogenase.

30. The recombinant photosynthetic microorganism of claim 29, wherein the methylmalonate semialdehyde dehydrogenase comprises an amino acid sequence having at least 70%, identity to an amino acid sequence selected from the group consisting of SEQ ID NO:18 and SEQ ID NO:19.

31. The recombinant photosynthetic microorganism of claim 30, wherein the methylmalonate semialdehyde dehydrogenase comprises an amino acid sequence having at least 85% identity to an amino acid sequence selected from the group consisting of SEQ ID NO:18 and SEQ ID NO:19.

32. The recombinant photosynthetic microorganism of claim 25, wherein the dehydrogenase is a D-2-hydroxyacid dehydrogenase.

33. The recombinant photosynthetic microorganism of claim 32, wherein the D-2-hydroxyacid dehydrogenase comprises an amino acid sequence having at least 70% identity to an amino acid sequence selected from the group consisting of SEQ ID NO:2, SEQ ID NO:29, SEQ ID NO:15, and SEQ ID NO:16.

34. The recombinant photosynthetic microorganism of claim 33, wherein the D-2-hydroxyacid dehydrogenase comprises an amino acid sequence having at least 85% identity to an amino acid sequence selected from the group consisting of SEQ ID NO:2, SEQ ID NO:29, SEQ ID NO:15, and SEQ ID NO:16.

35. The recombinant photosynthetic microorganism of claim 22, wherein the recombinant photosynthetic microorganism is a microalga.

36. The recombinant photosynthetic microorganism of claim 35, wherein the recombinant photosynthetic microorganism is a species of a genus selected from the group consisting of: *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Protothec, Pseudochlorella, Pseudoneochloris, Pyramimonas, Pyrobotrys, Scenedesmus, Skeletonema, Spyrogyra, Stichococcus, Tetraselmis, Thalassiosira, Viridiella*, and *Volvox*.

37. The recombinant photosynthetic microorganism of claim 22, wherein the recombinant photosynthetic microorganism is a cyanobacterium.

38. The recombinant photosynthetic microorganism of claim 35, wherein the recombinant photosynthetic microorganism is a species of a genus selected from the group consisting of: *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*.

39. An expression cassette comprising a heterologous promoter operably linked to a nucleic acid molecule comprising a nucleic acid sequence encoding a polypeptide comprising an amino acid sequence having at least 65% identity to SEQ ID NO:29 and a nucleic acid sequence encoding a thioesterase.

40. The expression cassette of claim 39, wherein the nucleic acid sequence encodes a polypeptide comprising an amino acid sequence having at least 85% identity to SEQ ID NO:29.

41. The method of claim 1, wherein the thioesterase is an acyl-ACP thioesterase.

42. The recombinant photosynthetic microorganism of claim 22, wherein the thioesterase is an acyl-ACP thioesterase.

* * * * *

SEQUENCE LISTING

<160> NUMBER OF SEQ ID NOS: 30

<210> SEQ ID NO 1
<211> LENGTH: 981
<212> TYPE: DNA
<213> ORGANISM: Unknown

<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 1

```
tccggcgcaa atctgaaagc gcaaggtgcc accgtcatga aacccgtcgt tcccttcatt      60
gcccggatgt ctgccgagga acgtgcggag tggatggcgc agtttgaaag gctgatgccg     120
cagatcgatg tgcgcccgct ggccaccatg gacgccgcag agcgcctgtc ggcacgcgtg     180
gccattgtcg ccaatccgga tccggcgcat ctgcatgagc tgccgggcct tgtctgggtg     240
cagagcctgt gggccggggt ggagcggttg ctgggcgagc tgatcgatac ggactttgcc     300
atcgtccgca tgaccgatcc gcagctggcg gaaaccatgg ccgaggcggt gctggccttt     360
tcgctttatc ttcaccggga cattccgctc tatctggcgc agcagcgcga gaagatctgg     420
gccgaagcct tgccgcgcct tgccgctgac cggcatatcg gcattctcgg gctggggaac     480
ctcggcaagg ctgcggcgcg cgcgcctgctg gccaatggct ttccggtcag cggctggagc     540
cgcacgcctg ccgaagtgga gggggcggag tgtttcagcg gtgaggaggg gctgcagcgg     600
gtgctgtcgc gctcggatat cgttgtcgtc ttgctgccgc tgacgccgga tacgcgcggc     660
ctgctcaaca cggctcgtct tgccatgctg ccgcgcggtg ctggactcat caattttggc     720
cgggggccga ttgtggacca gcctgcgctg ctggctgccc ttgatgaggg gcatctgtcc     780
catgcggtgc tggatgtctt tgcgcaggag ccgctgccgg tggacaatcc ctgctggagc     840
catccgtcgg tcacagtgct gccgcacatc agcgccccga caacaccggc gacggctgca     900
cggatcgtgg cggccaatct gtcggcttat ttcgagcggg gagaaatacc gccggcggtg     960
gaccgccagc ggggctactg a                                                981
```

<210> SEQ ID NO 2
<211> LENGTH: 326
<212> TYPE: PRT
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 2

```
Ser Gly Ala Asn Leu Lys Ala Gln Gly Ala Thr Val Met Lys Pro Val
1               5                   10                  15

Val Pro Phe Ile Ala Arg Met Ser Ala Glu Glu Arg Ala Glu Trp Met
            20                  25                  30

Ala Gln Phe Glu Arg Leu Met Pro Gln Ile Asp Val Arg Pro Leu Ala
        35                  40                  45

Thr Met Asp Ala Ala Glu Arg Leu Ser Ala Arg Val Ala Ile Val Ala
    50                  55                  60

Asn Pro Asp Pro Ala His Leu His Glu Leu Pro Gly Leu Val Trp Val
65                  70                  75                  80

Gln Ser Leu Trp Ala Gly Val Glu Arg Leu Leu Gly Glu Leu Ile Asp
                85                  90                  95

Thr Asp Phe Ala Ile Val Arg Met Thr Asp Pro Gln Leu Ala Glu Thr
            100                 105                 110

Met Ala Glu Ala Val Leu Ala Phe Ser Leu Tyr Leu His Arg Asp Ile
        115                 120                 125

Pro Leu Tyr Leu Ala Gln Gln Arg Glu Lys Ile Trp Ala Glu Ala Leu
    130                 135                 140
```

Pro Arg Leu Ala Ala Asp Arg His Ile Gly Ile Gly Leu Gly Asn
145                 150                 155                 160

Leu Gly Lys Ala Ala Ala Arg Arg Leu Leu Ala Asn Gly Phe Pro Val
            165                 170                 175

Ser Gly Trp Ser Arg Thr Pro Ala Glu Val Glu Gly Ala Glu Cys Phe
        180                 185                 190

Ser Gly Glu Glu Gly Leu Gln Arg Val Leu Ser Arg Ser Asp Ile Val
    195                 200                 205

Val Val Leu Leu Pro Leu Thr Pro Asp Thr Arg Gly Leu Leu Asn Thr
210                 215                 220

Ala Arg Leu Ala Met Leu Pro Arg Gly Ala Gly Leu Ile Asn Phe Gly
225                 230                 235                 240

Arg Gly Pro Ile Val Asp Gln Pro Ala Leu Leu Ala Ala Leu Asp Glu
                245                 250                 255

Gly His Leu Ser His Ala Val Leu Asp Val Phe Ala Gln Glu Pro Leu
            260                 265                 270

Pro Val Asp Asn Pro Cys Trp Ser His Pro Ser Val Thr Val Leu Pro
        275                 280                 285

His Ile Ser Ala Pro Thr Thr Pro Ala Thr Ala Ala Arg Ile Val Ala
    290                 295                 300

Ala Asn Leu Ser Ala Tyr Phe Glu Arg Gly Glu Ile Pro Pro Ala Val
305                 310                 315                 320

Asp Arg Gln Arg Gly Tyr
                325

<210> SEQ ID NO 3
<211> LENGTH: 1086
<212> TYPE: DNA
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 3
tcaaaaggaa aagtagtgcc agagccgtat ggtgtgacgc ttattattgc accgtggaac      60
tatccttttc aattagcaat tgcaccactt gtaggagcac ttgcagctgg aaatacaatc    120
gttttaaagc cgtcagagtt aacgccaagc gtttcaaaag tgcttaagag aatgttaggt    180
gaattattcc cagaagagct tgtagcggta gtagaaggtg gcgttgaaga gagtacatct    240
ttgctgaggg aaccaattga ttatattttc tttactggta gtgttggcgt tggaaaagtt    300
gtaatggaag cagcagcgaa acagttgacg ccgcttacgt tagaacttgg cgggaaaagt    360
ccttgtattg tacataaaga tgcaaagata gagatgacag caagaagaat tgtttggggt    420
aagtttttaa atgcagggca gacatgtgta gcgcctgatt atatgtacgt gcattcttcc    480
gtgaaagaac agctagttga ggcactgcga catgaaatca cagagcagta tagtaaagaa    540
cctttgcaaa atgaaaatta tgtgcgtatt gtaagtgagc gtcattttga acgattatgt    600 ggattttac aagatggtca agtcgtaatt ggtggaaact atgagaaaga tacattacat    660
attgaaccga cagtgctagc ggatattaca tggcaagatg ctgttatgga agatgaaatt    720
tttggtccga ttttaccaat catagagtac gacaatatag aagatgtaat tggcacaatc    780
cagcaacatc cgaagccgtt agcgttatat gtattttcgg aagataaaga agtacaaaag    840
aaagtgacga gtaatatttc atatggtgga ggctgtatta atgatgttgt ctaccatctt    900

```
gccacgccat atttaccttt tgggggtgtt ggaagtagtg gattagggggg ttatcatggg      960 gaagaaagtt ttcggacttt ttcacattat aaaagcattt tagcccaatc tacagcattc     1020
gacatgaaaa ttcgttactc ttctacaaaa agtgctttaa aattcatacg aaagttgtta     1080
aaatga                                                                1086
```

```
<210> SEQ ID NO 4
<211> LENGTH: 361
<212> TYPE: PRT
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 4

Ser Lys Gly Lys Val Val Pro Glu Pro Tyr Gly Val Thr Leu Ile Ile
1               5                   10                  15

Ala Pro Trp Asn Tyr Pro Phe Gln Leu Ala Ile Ala Pro Leu Val Gly
            20                  25                  30

Ala Leu Ala Ala Gly Asn Thr Ile Val Leu Lys Pro Ser Glu Leu Thr
        35                  40                  45

Pro Ser Val Ser Lys Val Leu Lys Arg Met Leu Gly Glu Leu Phe Pro
    50                  55                  60

Glu Glu Leu Val Ala Val Val Glu Gly Val Glu Glu Ser Thr Ser
65                  70                  75                  80

Leu Leu Arg Glu Pro Ile Asp Tyr Ile Phe Phe Thr Gly Ser Val Gly
                85                  90                  95

Val Gly Lys Val Val Met Glu Ala Ala Ala Lys Gln Leu Thr Pro Leu
            100                 105                 110

Thr Leu Glu Leu Gly Gly Lys Ser Pro Cys Ile Val His Lys Asp Ala
        115                 120                 125

Lys Ile Glu Met Thr Ala Arg Arg Ile Val Trp Gly Lys Phe Leu Asn
    130                 135                 140

Ala Gly Gln Thr Cys Val Ala Pro Asp Tyr Met Tyr Val His Ser Ser
145                 150                 155                 160

Val Lys Glu Gln Leu Val Glu Ala Leu Arg His Glu Ile Thr Glu Gln
                165                 170                 175

Tyr Ser Lys Glu Pro Leu Gln Asn Glu Asn Tyr Val Arg Ile Val Ser
            180                 185                 190

Glu Arg His Phe Glu Arg Leu Cys Gly Phe Leu Gln Asp Gly Gln Val
        195                 200                 205

Val Ile Gly Gly Asn Tyr Glu Lys Asp Thr Leu His Ile Glu Pro Thr
    210                 215                 220

Val Leu Ala Asp Ile Thr Trp Gln Asp Ala Val Met Glu Asp Glu Ile
225                 230                 235                 240

Phe Gly Pro Ile Leu Pro Ile Ile Glu Tyr Asp Asn Ile Glu Asp Val
                245                 250                 255

Ile Gly Thr Ile Gln Gln His Pro Lys Pro Leu Ala Leu Tyr Val Phe
            260                 265                 270

Ser Glu Asp Lys Glu Val Gln Lys Lys Val Thr Ser Asn Ile Ser Tyr
        275                 280                 285

Gly Gly Gly Cys Ile Asn Asp Val Val Tyr His Leu Ala Thr Pro Tyr
    290                 295                 300

Leu Pro Phe Gly Gly Val Gly Ser Ser Gly Leu Gly Gly Tyr His Gly
305                 310                 315                 320
```

Glu Glu Ser Phe Arg Thr Phe Ser His Tyr Lys Ser Ile Leu Ala Gln
            325                 330                 335

Ser Thr Ala Phe Asp Met Lys Ile Arg Tyr Ser Ser Thr Lys Ser Ala
        340                 345                 350

Leu Lys Phe Ile Arg Lys Leu Leu Lys
        355                 360

<210> SEQ ID NO 5
<211> LENGTH: 783
<212> TYPE: DNA
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t

<400> SEQUENCE: 5
ttggccgatt cattaatgca gagatcaaaa ggaaaagtag tgccagagcc gtatggtgtg      60
acgcttatta ttgcaccgtg gaactatcct tttcaattag caattgcacc acttgtagga    120
gcacttgcag ctggaaatac aatcgtttta aagccgtcag agttaacgcc aagcgtttca    180
aaagtgctta agagaatgtt aggtgaatta ttcccagaag agcttgtagc ggtagtagaa    240
ggtggcgttg aagagagtac atctttgctg agggaaccaa ttgattatat tttctttact    300
ggtagtgttg gcgttggaaa agttgtaatg gaagcagcag cgaaacagtt gacgccgctt    360
acgttagaac ttggcgggaa aagtccttgt attgtacata aagatgcaaa gatagagatg    420
acagcaagaa gaattgtttg gggtaagttt ttaaatgcag gcagacatg tgtagcgcct    480 gattatatgt acgtgcattc ttccgtgaaa gaacagctag ttgaggcact gcgacatgaa    540
atcacagagc agtatagtaa agaacctttg caaaatgaaa attatgtgcg tattgtaagt    600
gagcgtcatt ttgaacgatt atgtggattt ttacaagatg gtcaagtcgt aattggtgga    660
aactatgaga agatacatt acatattgaa ccgacagtgc tagcggatat tacatggcaa    720
gatgctgtta tggaagatga aattttggt ccganttac cnatcataga gtacgacaat    780
ata                                                                 783

<210> SEQ ID NO 6
<211> LENGTH: 261
<212> TYPE: PRT
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 6

Leu Ala Asp Ser Leu Met Gln Arg Ser Lys Gly Lys Val Val Pro Glu
1               5                   10                  15

Pro Tyr Gly Val Thr Leu Ile Ile Ala Pro Trp Asn Tyr Pro Phe Gln
            20                  25                  30

Leu Ala Ile Ala Pro Leu Val Gly Ala Leu Ala Ala Gly Asn Thr Ile
        35                  40                  45

```
Val Leu Lys Pro Ser Glu Leu Thr Pro Ser Val Ser Lys Val Leu Lys
     50                  55                  60

Arg Met Leu Gly Glu Leu Phe Pro Glu Leu Val Ala Val Val Glu
 65                  70                  75                  80

Gly Gly Val Glu Glu Ser Thr Ser Leu Leu Arg Glu Pro Ile Asp Tyr
                 85                  90                  95

Ile Phe Phe Thr Gly Ser Val Gly Val Gly Lys Val Val Met Glu Ala
                100                 105                 110

Ala Ala Lys Gln Leu Thr Pro Leu Thr Leu Glu Leu Gly Gly Lys Ser
            115                 120                 125

Pro Cys Ile Val His Lys Asp Ala Lys Ile Glu Met Thr Ala Arg Arg
130                 135                 140

Ile Val Trp Gly Lys Phe Leu Asn Ala Gly Gln Thr Cys Val Ala Pro
145                 150                 155                 160

Asp Tyr Met Tyr Val His Ser Ser Val Lys Glu Gln Leu Val Glu Ala
                165                 170                 175

Leu Arg His Glu Ile Thr Glu Gln Tyr Ser Lys Glu Pro Leu Gln Asn
            180                 185                 190

Glu Asn Tyr Val Arg Ile Val Ser Glu Arg His Phe Glu Arg Leu Cys
        195                 200                 205

Gly Phe Leu Gln Asp Gly Gln Val Val Ile Gly Gly Asn Tyr Glu Lys
210                 215                 220

Asp Thr Leu His Ile Glu Pro Thr Val Leu Ala Asp Ile Thr Trp Gln
225                 230                 235                 240

Asp Ala Val Met Glu Asp Glu Ile Phe Gly Pro Ile Leu Pro Ile Ile
                245                 250                 255

Glu Tyr Asp Asn Ile
            260

<210> SEQ ID NO 7
<211> LENGTH: 455
<212> TYPE: PRT
<213> ORGANISM: Bacillus thuringiensis

<400> SEQUENCE: 7

Met Ser Ile Thr Ser Ile Val Ser Arg Gln Lys Glu Tyr Phe Leu Lys
 1               5                  10                  15

Gly Cys Thr Arg Ser Ile Glu Met Arg Lys Asn Asn Leu Lys Lys Leu
                20                  25                  30

Tyr Glu Gly Ile Gln Arg Phe Glu Glu Glu Ile Phe Gln Ala Leu Lys
            35                  40                  45

Leu Asp Leu Asn Lys Ser Val His Glu Ser Phe Thr Thr Glu Val Gly
 50                  55                  60

Tyr Val Leu Lys Glu Ile Ser Phe Gln Leu Lys His Met Ser Ser Trp
 65                  70                  75                  80

Ser Lys Pro Lys Arg Val Arg Thr Ala Leu Thr His Phe Gly Ser Lys
                 85                  90                  95

Gly Lys Val Val Pro Glu Pro Tyr Gly Val Thr Leu Ile Ile Ala Pro
                100                 105                 110

Trp Asn Tyr Pro Phe Gln Leu Ala Ile Ala Pro Leu Val Gly Ala Leu
            115                 120                 125

Ala Ala Gly Asn Thr Ile Val Leu Lys Pro Ser Glu Leu Thr Pro Ser
130                 135                 140

Val Ser Lys Val Leu Lys Arg Met Leu Gly Glu Leu Phe Pro Glu Glu
145                 150                 155                 160
```

Leu Val Ala Val Val Glu Gly Val Glu Glu Ser Thr Ser Leu Leu
            165                 170                 175

Arg Glu Pro Ile Asp Tyr Ile Phe Phe Thr Gly Ser Val Gly Val Gly
        180                 185                 190

Lys Val Val Met Glu Ala Ala Lys Gln Leu Thr Pro Leu Thr Leu
        195                 200                 205

Glu Leu Gly Gly Lys Ser Pro Cys Ile Val His Lys Asp Ala Lys Ile
        210                 215                 220

Glu Met Thr Ala Arg Arg Ile Val Trp Gly Lys Phe Leu Asn Ala Gly
225                 230                 235                 240

Gln Thr Cys Val Ala Pro Asp Tyr Met Tyr Val His Ser Ser Val Lys
                245                 250                 255

Glu Gln Leu Val Glu Ala Leu Arg His Glu Ile Thr Glu Gln Tyr Ser
                260                 265                 270

Lys Glu Pro Leu Gln Asn Glu Asn Tyr Val Arg Ile Val Ser Glu Arg
            275                 280                 285

His Phe Glu Arg Leu Cys Gly Phe Leu Gln Asp Gly Gln Val Val Ile
        290                 295                 300

Gly Gly Asn Tyr Lys Lys Asp Thr Leu His Ile Glu Pro Thr Val Leu
305                 310                 315                 320

Ala Asp Ile Thr Trp Gln Asp Ala Val Met Glu Asp Glu Ile Phe Gly
                325                 330                 335

Pro Ile Leu Pro Ile Ile Glu Tyr Asp Asn Ile Glu Asp Val Ile Gly
                340                 345                 350

Thr Ile Gln Gln His Pro Lys Pro Leu Ala Leu Tyr Val Phe Ser Glu
            355                 360                 365

Asp Lys Glu Val Gln Lys Val Thr Ser Asn Ile Ser Tyr Gly Gly
        370                 375                 380

Gly Cys Ile Asn Asp Val Val Tyr His Leu Ala Thr Pro Tyr Leu Pro
385                 390                 395                 400

Phe Gly Gly Val Gly Ser Ser Gly Leu Gly Gly Tyr His Gly Glu Glu
                405                 410                 415

Ser Phe Arg Thr Phe Ser His Tyr Lys Ser Ile Leu Ala Gln Ser Thr
            420                 425                 430

Ala Phe Asp Met Lys Ile Arg Tyr Ser Ser Thr Lys Ser Ala Leu Lys
        435                 440                 445

Phe Ile Arg Lys Leu Leu Lys
        450                 455

<210> SEQ ID NO 8
<211> LENGTH: 1753
<212> TYPE: DNA
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 8
gatccgcttt aacgctggca tctgcagcca cggtttgccg taaaacagct agtaaatttg      60
tgacattgtt ttccgccacg gcatctcgtt ctactaaagc tgggatgatg gaaacaattg     120
tgtcgtgctg ttttgcagcg tctaaatcga tgttgttata cccaatgcca tggcgagaaa     180
tcagcaacaa ttcatctttt tgttcaaaaa attctttcgt gaaaaatggc gtcacgctag     240
caataataat cgtatatcct tgtaaacgtt ccgctaactc tttgccacca atttcactgt     300

```
cgactgtaaa atgcttcacg gtgcctattt tttctaagcg cgtcaagtgt tcaggaaaaa    360
tttgaccaaa actactggaa ttcactatgg caattttttg ttttttttaac atgactaaac   420 tcctttactg acttttttacg acttcatgcc cgccaaatcc ttgtcgcaaa gaagcgacca   480
ctttgtttga aaaatgattt gctagcatac tttcatttcg agtaaataag gacaacgccg    540
tagttgggac gggcatctcc aaacgcaatg cttcttcaat catccatttg gcttcgccat    600
ttgctgccac tttcccttct agattggcta acgtaggatt ttccgcaaaa cctctttcgc    660
taagcccatc aagcgagctt caataatcga gccgtgattc cacacatcgg ctactttctc    720
caacgcaaaa tcatattcgg cagcttctaa taaattgaat ccttcgccca tggcttgcat    780
catgacgtac tcaatcccgt tatgcaccat tttcaaatag tgaccagctc ctgatttccc    840
agcataaaga tacccttgtt cacaagctaa atcttcaaaa aatggggtta acactttgac    900
agcttcaggc gcaccgccaa ccattaaaca cgctccttcc cgcgctcctt tgatgccacc    960
agaagtacca caatcaataa aataaattcc ttttccttta gcaaattgag cattcgcaac   1020
actatcatga aaatttgaat tgccactatc cacaatgata tcctctggtg ctaattgctc   1080
taccaattct gccactaatt gattggtaat ctgaccagcg ggggtactta aaaaaatcac   1140
cttccttttt ttaagcgctt tcaataattc tgacaacgaa tctacaacgg aaagcccctg   1200
ctctctagca gtcgctcttg cttcctttgt cacatcaaag ccaataatgg gccagccttg   1260
ttcgtgaaca tttaatgcca tgttcaaacc cattttccca agtccaataa agccaatgtc   1320 cattttttctt tcacctgcct cttttgatac ttcaatcata aaggataaaa aaaataatgt   1380
aaacgattac actaattaaa aaatatttttt tattttttag caaaaatctt gcctactcaa   1440
aaggtaaaac gttttttattt ttaaggagct ttcatacaaa aaacacaagt aaatctcttg   1500
gtatcacgtt cttttttactg gctactttct ttagttgaga gaagtctttt caagacccct   1560
tcatttttca gaaaaaagat tatttatttt tttggggctt ttttttaaaga atttcttttt   1620 tgtggagaaa aagagaaatt gtatttgtcc tcttttttcca ctataatcag tctataccaa   1680
caatgaaaag gcattcattt tattttttaaa aaaataagat tggaggaacg tgttaatgaa   1740
aaaccactat ttg                                                     1753
```

<210> SEQ ID NO 9
<211> LENGTH: 900
<212> TYPE: DNA
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 9

```
ttactgactt tttacgactt catgcccgcc aaatccttgt cgcaaagaag cgaccacttt     60
gtttgaaaaa tgatttgcta gcatactttc atttcgagta aataaggaca acgccgtagt   120
tgggacgggc atctccaaac gcaatgcttc ttcaatcatc catttggctt cgccatttgc   180
tgccactttc ccttctagat tggctaacgt aggattttcc gcaaaaacct ctttcgctaa   240
gcccatcaag cgagcttcaa taatcgagcc gtgattccac acatcggcta ctttctccaa   300
cgcaaaatca tattcggcag cttctaataa attgaatcct tcgcccatgg cttgcatcat   360
gacgtactca atcccgttat gcaccatttt caaatagtga ccagctcctg atttcccagc   420
ataaagatac ccttgttcac aagctaaatc ttcaaaaaat ggggttaaca ctttgacagc   480
```

```
ttcaggcgca ccgccaacca ttaaacacgc tccttcccgc gctcctttga tgccaccaga      540
agtaccacaa tcaataaaat aaattccttt tccttagca aattgagcat tcgcaacact       600
atcatgaaaa tttgaattgc cactatccac aatgatatcc tctggtgcta attgctctac      660
caattctgcc actaattgat tggtaatctg accagcgggg gtacttaaaa aaatcaccTT      720 cctttttta agcgctttca ataattctga caacgaatct acaacggaaa gcccctgctc       780
tctagcagtc gctcttgctt cctttgtcac atcaaagcca ataatgggcc agccttgttc      840
gtgaacattt aatgccatgt tcaaacccat tttcccaagt ccaataaagc caatgtccat      900
```

<210> SEQ ID NO 10
<211> LENGTH: 299
<212> TYPE: PRT
<213> ORGANISM: Unknown
<220> FEATURE:
<223> OTHER INFORMATION: Aquatic organism screen of a metagenomic
    library containing DNA fragments from an environmental sample
    removed from a shipping channel in Laguna Madre, Texas

<400> SEQUENCE: 10

```
Met Asp Ile Gly Phe Ile Gly Leu Gly Lys Met Gly Leu Asn Met Ala
1               5                   10                  15

Leu Asn Val His Glu Gln Gly Trp Pro Ile Ile Gly Phe Asp Val Thr
            20                  25                  30

Lys Glu Ala Arg Ala Thr Ala Arg Glu Gln Gly Leu Ser Val Val Asp
        35                  40                  45

Ser Leu Ser Glu Leu Leu Lys Ala Leu Lys Arg Lys Val Ile Phe
    50                  55                  60

Leu Ser Thr Pro Ala Gly Gln Ile Thr Asn Gln Leu Val Ala Glu Leu
65                  70                  75                  80

Val Glu Gln Leu Ala Pro Glu Asp Ile Ile Val Asp Ser Gly Asn Ser
                85                  90                  95

Asn Phe His Asp Ser Val Ala Asn Ala Gln Phe Ala Lys Glu Lys Gly
            100                 105                 110

Ile Tyr Phe Ile Asp Cys Gly Thr Ser Gly Gly Ile Lys Gly Ala Arg
        115                 120                 125

Glu Gly Ala Cys Leu Met Val Gly Gly Ala Pro Glu Ala Val Lys Val
    130                 135                 140

Leu Thr Pro Phe Phe Glu Asp Leu Ala Cys Glu Gln Gly Tyr Leu Tyr
145                 150                 155                 160

Ala Gly Lys Ser Gly Ala Gly His Tyr Leu Lys Met Val His Asn Gly
                165                 170                 175

Ile Glu Tyr Val Met Met Gln Ala Met Gly Glu Gly Phe Asn Leu Leu
            180                 185                 190

Glu Ala Ala Glu Tyr Asp Phe Ala Leu Glu Lys Val Ala Asp Val Trp
        195                 200                 205

Asn His Gly Ser Ile Ile Glu Ala Arg Leu Met Gly Leu Ala Lys Glu
    210                 215                 220

Val Phe Ala Glu Asn Pro Thr Leu Ala Asn Leu Glu Gly Lys Val Ala
225                 230                 235                 240

Ala Asn Gly Glu Ala Lys Trp Met Ile Glu Glu Ala Leu Arg Leu Glu
                245                 250                 255

Met Pro Val Pro Thr Thr Ala Leu Ser Leu Phe Thr Arg Asn Glu Ser
            260                 265                 270

Met Leu Ala Asn His Phe Ser Asn Lys Val Val Ala Ser Leu Arg Gln
        275                 280                 285
```

```
Gly Phe Gly Gly His Glu Val Val Lys Ser Gln
        290                 295
```

```
<210> SEQ ID NO 11
<211> LENGTH: 311
<212> TYPE: PRT
<213> ORGANISM: Enterococcus faecalis

<400> SEQUENCE: 11
```

```
Met Ile Glu Val Ser Lys Glu Ala Gly Glu Arg Lys Met Asp Ile Gly
1               5                   10                  15

Phe Ile Gly Leu Gly Lys Met Gly Leu Asn Met Ala Leu Asn Val His
            20                  25                  30

Glu Gln Gly Trp Pro Ile Ile Gly Phe Asp Val Thr Lys Glu Ala Arg
        35                  40                  45

Ala Thr Ala Arg Glu Gln Gly Leu Ser Val Val Asp Ser Leu Ser Glu
    50                  55                  60

Leu Leu Lys Ala Leu Lys Lys Arg Lys Val Ile Phe Leu Ser Thr Pro
65                  70                  75                  80

Ala Gly Gln Ile Thr Asn Gln Leu Val Ala Glu Leu Val Glu Gln Leu
                85                  90                  95

Ala Pro Glu Asp Ile Ile Val Asp Ser Gly Asn Ser Asn Phe His Asp
            100                 105                 110

Ser Val Ala Asn Ala Gln Phe Ala Lys Glu Lys Gly Ile Tyr Phe Ile
        115                 120                 125

Asp Cys Gly Thr Ser Gly Gly Ile Lys Gly Ala Arg Glu Gly Ala Cys
    130                 135                 140

Leu Met Val Gly Gly Ala Pro Glu Ala Val Lys Val Leu Thr Pro Phe
145                 150                 155                 160

Phe Glu Asp Leu Ala Cys Glu Gln Gly Tyr Leu Tyr Ala Gly Lys Ser
                165                 170                 175

Gly Ala Gly His Tyr Leu Lys Met Val His Asn Gly Ile Glu Tyr Val
            180                 185                 190

Met Met Gln Ala Met Gly Glu Gly Phe Asn Leu Leu Glu Ala Ala Glu
        195                 200                 205

Tyr Asp Phe Ala Leu Glu Lys Val Ala Asp Val Trp Asn His Gly Ser
    210                 215                 220

Ile Ile Glu Ala Arg Leu Met Gly Leu Ala Lys Glu Val Phe Ala Glu
225                 230                 235                 240

Asn Pro Thr Leu Ala Asn Leu Glu Gly Lys Val Ala Ala Asn Gly Glu
                245                 250                 255

Ala Lys Trp Met Ile Glu Glu Ala Leu Arg Leu Glu Met Pro Val Pro
            260                 265                 270

Thr Thr Ala Leu Ser Leu Phe Thr Arg Asn Glu Ser Met Leu Ala Asn
        275                 280                 285

His Phe Ser Asn Lys Val Val Ala Ser Leu Arg Gln Gly Phe Gly Gly
    290                 295                 300

His Glu Val Val Lys Ser Gln
305                 310
```

```
<210> SEQ ID NO 12
<211> LENGTH: 1449
<212> TYPE: DNA
<213> ORGANISM: Synechocystis PCC6803

<400> SEQUENCE: 12
```

-continued

```
tcaatcaagc cattccgtgt ggaaaaattc tcccctcggc ttatcagtcc gttcataggt      60
gtgggcccca agtaatccc gttgcgcttg agtcaggttt tggggaagca ccgcccgccg      120
gtaactgtca agtaatcca acgaggaact aaaggccggc actgcaatgc ccatttcatt      180
ggccagcatc aacacttctc gccatggccc ctggcgatcc aaaatacttt gcttgaattc      240
cggagctaga agtaaattgg gcaactgggg attgtcttta aaagctttct tgatcttgtc      300
taaaaagcca gctcggataa tgcaacccc tttccaaatg cgggcaattt ccggcaggtt      360
aacgtcgtag ccaaattcct gggaagcttt ggcaattagg ccatgccct gggcatagga      420 acacattttc gagcaataga gggcatcccg caccttagga atccaggctt ctacgtcccc      480
actaaaggtt ttactgggac ccgacagttg accggaagcg gccacccgtt cttctttgag      540
ggaagacatt accctggcgt taacggcggc gtaaatagtg ggaatgggca ctcctaattc      600
caaaccactc atcaccgtcc agcgtcctgt gcccttttgg ccggcggcat caaggatgta      660
gtcaattaaa tggcctccgg tttcgggatc cttttagca aaaatgtcgg tgctgatttc      720
aatcaggaag gagtttaact catcggtttg attccattgg ccaaaaactt cgtggagttg      780
ttcgttgctc aagccgaggc cattttcaa gatgtcgtag gcttcagcga ttagttgcat      840
atcgccatac tcaatgccgt tgtggaccat tttgacgtaa tgtcctgctc ccctgggcc       900 aataaaagtc acacaggcgg gattatcggg gtcttccacc tgggcggcaa ttttagtcag      960
aatgggttcc aattctttgt aggcggccgg ggtaccaccg ggcatcaaac taggacccag     1020
taatgcgcct tcttcccctc cactgactcc catgccgaca agccaggc cggtggcttc       1080 caaatctttg gtgcgacgtt ccgtatcttc ataagggag ttgccaccat caatgatcat     1140
gtccccttct tccaacaggg gcttcaactc attgatcact gcatccacgg gtcccccagc     1200
tttgaccatt acaaggattt tacggggcg ttccaacagt tggacaaatt cttctacggt     1260
gtaggcggct tgatatcttt tgcccacagc ccgttcggcc atgaatttct cagttttgtt     1320
gggggaacgg ttaaacacgg cgatgggaaa gcctcgactt tccacgttga gggcaagatt     1380
ttcccccatt accgctagtc caattacccc aaaagttcgc ttagtcataa tagctacgtt     1440
aaattgcac                                                             1449
```

<210> SEQ ID NO 13
<211> LENGTH: 482
<212> TYPE: PRT
<213> ORGANISM: Synechocystis PCC6803

<400> SEQUENCE: 13

```
Met Gln Phe Asn Val Ala Ile Met Thr Lys Arg Thr Phe Gly Val Ile
1               5                   10                  15

Gly Leu Ala Val Met Gly Glu Asn Leu Ala Leu Asn Val Glu Ser Arg
            20                  25                  30

Gly Phe Pro Ile Ala Val Phe Asn Arg Ser Pro Asn Lys Thr Glu Lys
        35                  40                  45

Phe Met Ala Glu Arg Ala Val Gly Lys Asp Ile Lys Ala Ala Tyr Thr
    50                  55                  60

Val Glu Glu Phe Val Gln Leu Leu Glu Arg Pro Arg Lys Ile Leu Val
65                  70                  75                  80

Met Val Lys Ala Gly Gly Pro Val Asp Ala Val Ile Asn Glu Leu Lys
                85                  90                  95

Pro Leu Leu Glu Glu Gly Asp Met Ile Ile Asp Gly Gly Asn Ser Leu
            100                 105                 110
```

Tyr Glu Asp Thr Glu Arg Arg Thr Lys Asp Leu Glu Ala Thr Gly Leu
         115                 120                 125

Gly Phe Val Gly Met Gly Val Ser Gly Gly Glu Gly Ala Leu Leu
130                 135                 140

Gly Pro Ser Leu Met Pro Gly Thr Pro Ala Ala Tyr Lys Glu Leu
145                 150                 155                 160

Glu Pro Ile Leu Thr Lys Ile Ala Ala Gln Val Glu Asp Pro Asp Asn
                 165                 170                 175

Pro Ala Cys Val Thr Phe Ile Gly Pro Gly Ala Gly His Tyr Val
             180                 185                 190

Lys Met Val His Asn Gly Ile Glu Tyr Gly Asp Met Gln Leu Ile Ala
                 195                 200                 205

Glu Ala Tyr Asp Ile Leu Lys Asn Gly Leu Gly Leu Ser Asn Glu Gln
210                 215                 220

Leu His Glu Val Phe Gly Gln Trp Asn Gln Thr Asp Glu Leu Asn Ser
225                 230                 235                 240

Phe Leu Ile Glu Ile Ser Thr Asp Ile Phe Ala Lys Lys Asp Pro Glu
                 245                 250                 255

Thr Gly Gly His Leu Ile Asp Tyr Ile Leu Asp Ala Ala Gly Gln Lys
                 260                 265                 270

Gly Thr Gly Arg Trp Thr Val Met Ser Gly Leu Glu Leu Gly Val Pro
                 275                 280                 285

Ile Pro Thr Ile Tyr Ala Ala Val Asn Ala Arg Val Met Ser Ser Leu
                 290                 295                 300

Lys Glu Glu Arg Val Ala Ala Ser Gly Gln Leu Ser Gly Pro Ser Lys
305                 310                 315                 320

Thr Phe Ser Gly Asp Val Glu Ala Trp Ile Pro Lys Val Arg Asp Ala
                 325                 330                 335

Leu Tyr Cys Ser Lys Met Cys Ser Tyr Ala Gln Gly Met Ala Leu Ile
                 340                 345                 350

Ala Lys Ala Ser Gln Glu Phe Gly Tyr Asp Val Asn Leu Pro Glu Ile
                 355                 360                 365

Ala Arg Ile Trp Lys Gly Gly Cys Ile Ile Arg Ala Gly Phe Leu Asp
                 370                 375                 380

Lys Ile Lys Lys Ala Phe Lys Asp Asn Pro Gln Leu Pro Asn Leu Leu
385                 390                 395                 400

Leu Ala Pro Glu Phe Lys Gln Ser Ile Leu Asp Arg Gln Gly Pro Trp
                 405                 410                 415

Arg Glu Val Leu Met Leu Ala Asn Glu Met Gly Ile Ala Val Pro Ala
                 420                 425                 430

Phe Ser Ser Ser Leu Asp Tyr Phe Asp Ser Tyr Arg Arg Ala Val Leu
                 435                 440                 445

Pro Gln Asn Leu Thr Gln Ala Gln Arg Asp Tyr Phe Gly Ala His Thr
450                 455                 460

Tyr Glu Arg Thr Asp Lys Pro Arg Gly Glu Phe Phe His Thr Glu Trp
465                 470                 475                 480

Leu Asp

<210> SEQ ID NO 14
<211> LENGTH: 412
<212> TYPE: DNA
<213> ORGANISM: Unknown
<220> FEATURE:
<223> OTHER INFORMATION: Aquatic organism screen of a metagenomic library containing DNA fragments from an environmental sample
removed from a shipping channel in Laguna Madre, Texas

<400> SEQUENCE: 14

```
atgttaaaaa aacaaaaaat tgccatagtg aattccagta gttttggtca aattttttcct      60 gaacacttga cgcgcttaga aaaataggc accgtgaagc attttacagt cgacagtgaa       120
attggtggca aagagttagc ggaacgttta caaggatata cgattattat tgctagcgtg      180
acgccatttt tcacgaaaga attttttgaa cataaagatg aattgttgct gatttctcgc      240
catggcattg ggtataacaa catcgattta gacgctgcaa aacagcacga cacaattgtt      300
tccatcatcc cagctttagt agaacgagat gccgtggcgg aaaacaatgt cacaaattta      360
ctagctgttt tacggcaaac cgtggctgca gatgccagcg ttaaagcgga tc              412
```

<210> SEQ ID NO 15
<211> LENGTH: 137
<212> TYPE: PRT
<213> ORGANISM: Unknown
<220> FEATURE:
<223> OTHER INFORMATION: Aquatic organism screen of a metagenomic
library containing DNA fragments from an environmental sample
removed from a shipping channel in Laguna Madre, Texas

<400> SEQUENCE: 15

```
Met Leu Lys Lys Gln Lys Ile Ala Ile Val Asn Ser Ser Phe Gly
1               5                   10                  15

Gln Ile Phe Pro Glu His Leu Thr Arg Leu Glu Lys Ile Gly Thr Val
                20                  25                  30

Lys His Phe Thr Val Asp Ser Glu Ile Gly Gly Lys Glu Leu Ala Glu
            35                  40                  45

Arg Leu Gln Gly Tyr Thr Ile Ile Ile Ala Ser Val Thr Pro Phe Phe
        50                  55                  60

Thr Lys Glu Phe Phe Glu His Lys Asp Glu Leu Leu Leu Ile Ser Arg
65                  70                  75                  80

His Gly Ile Gly Tyr Asn Asn Ile Asp Leu Asp Ala Ala Lys Gln His
                85                  90                  95

Asp Thr Ile Val Ser Ile Ile Pro Ala Leu Val Glu Arg Asp Ala Val
            100                 105                 110

Ala Glu Asn Asn Val Thr Asn Leu Leu Ala Val Leu Arg Gln Thr Val
        115                 120                 125

Ala Ala Asp Ala Ser Val Lys Ala Asp
    130                 135
```

<210> SEQ ID NO 16
<211> LENGTH: 333
<212> TYPE: PRT
<213> ORGANISM: Enterococcus faecalis

<400> SEQUENCE: 16

```
Met Leu Lys Lys Gln Lys Ile Ala Ile Val Asn Ser Ser Phe Gly
1               5                   10                  15

Gln Ile Phe Pro Glu His Leu Thr Arg Leu Glu Lys Ile Gly Thr Val
                20                  25                  30

Lys His Phe Thr Val Asp Ser Glu Ile Gly Gly Lys Glu Leu Ala Glu
            35                  40                  45

Arg Leu Gln Gly Tyr Thr Ile Ile Ile Ala Ser Val Thr Pro Phe Phe
        50                  55                  60

Thr Lys Glu Phe Phe Glu His Lys Asp Glu Leu Leu Leu Ile Ser Arg
```

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |

His Gly Ile Gly Tyr Asn Asn Ile Asp Leu Asp Ala Ala Lys Gln His
                    85                  90                  95

Asp Thr Ile Val Ser Ile Ile Pro Ala Leu Val Glu Arg Asp Ala Val
                100                 105                 110

Ala Glu Asn Asn Val Thr Asn Leu Leu Ala Val Leu Arg Gln Thr Val
            115                 120                 125

Ala Ala Asp Ala Ser Val Lys Ala Asp Gln Trp Glu Lys Arg Ala Asn
130                 135                 140

Phe Val Gly Arg Thr Leu Phe Asn Lys Thr Val Gly Val Ile Gly Val
145                 150                 155                 160

Gly Asn Thr Gly Ser Cys Val Val Glu Thr Leu Arg Asn Gly Phe Arg
                165                 170                 175

Cys Asp Val Leu Ala Tyr Asp Pro Tyr Lys Ser Ala Thr Tyr Leu Gln
                180                 185                 190

Ser Tyr Gly Ala Lys Lys Val Asp Leu Asp Thr Leu Leu Ala Ser Ala
            195                 200                 205

Asp Ile Ile Cys Leu Cys Ala Asn Leu Thr Glu Glu Ser Tyr His Met
    210                 215                 220

Ile Gly Ser Ala Glu Ile Ala Lys Met Lys Asp Gly Val Tyr Leu Ser
225                 230                 235                 240

Asn Ser Ala Arg Gly Ala Leu Ile Asp Glu Glu Ala Met Ile Ala Gly
                245                 250                 255

Leu Gln Ser Gly Lys Ile Ala Gly Leu Gly Thr Asp Val Leu Glu Glu
                260                 265                 270

Glu Pro Gly Arg Lys Asn His Pro Tyr Leu Ala Phe Glu Asn Val Val
            275                 280                 285

Met Thr Pro His Thr Ser Ala Tyr Thr Met Glu Cys Leu Gln Ala Met
    290                 295                 300

Gly Glu Lys Cys Val Gln Asp Val Glu Asp Val Val Gln Gly Ile Leu
305                 310                 315                 320

Pro Gln Arg Thr Val Gln Glu Val Ser Arg Tyr Val Ser
                325                 330

<210> SEQ ID NO 17
<211> LENGTH: 552
<212> TYPE: DNA
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 17

```
cggggtctgc cgaagggcgt cttcaatgtc gtgcacggcg cgcatgacgt cgtaaacggc      60
gttcttgaac atccggagat taaagccatc tcattcgtcg gttcaaaacc tgtcggcgag     120
tatgttttca aaaaaggcag cgaacatttg aaacgcgtgc aggcgttaac gggcgcgaaa     180
aaccatacga tcgtgttaaa tgacgcccac cttgaagata cggtgacaaa cattatcggc     240
gcggcattcg gttcggcagg agagcgctgc atggcatgcg cggttgtgac ggttgaagag     300
ggaatcgccg atgagtttat ggcgaaatta caggaaaagg tcgcagacat caagatcgga     360
aacggactgg atgacggcgt gttcttaggc ccggtcatcc gcgaggacaa caaaaaacgg     420
acgcacagct atattgaaaa aggcatcgaa gaaggagcga gacttctttg tgacgggcgt     480
gaaaacgcaa cggaagacgg ctatttcgtc ggaccgacaa ttttttgacaa cgtgacgacg     540
```

```
gatatggcga tc                                                        552
```

<210> SEQ ID NO 18
<211> LENGTH: 184
<212> TYPE: PRT
<213> ORGANISM: Unknown
<220> FEATURE:
<223> OTHER INFORMATION: Methylmalonate semialdehyde dehydrogenase
      identified from a screen of a metagenomic library containing DNA
      fragments from an environmental sample removed from a shipping
      channel in Laguna Madre, Texas.

<400> SEQUENCE: 18

Arg Gly Leu Pro Lys Gly Val Phe Asn Val Val His Gly Ala His Asp
1               5                   10                  15

Val Val Asn Gly Val Leu Glu His Pro Glu Ile Lys Ala Ile Ser Phe
            20                  25                  30

Val Gly Ser Lys Pro Val Gly Glu Tyr Val Phe Lys Lys Gly Ser Glu
        35                  40                  45

His Leu Lys Arg Val Gln Ala Leu Thr Gly Ala Lys Asn His Thr Ile
    50                  55                  60

Val Leu Asn Asp Ala His Leu Glu Asp Thr Val Thr Asn Ile Ile Gly
65                  70                  75                  80

Ala Ala Phe Gly Ser Ala Gly Glu Arg Cys Met Ala Cys Ala Val Val
                85                  90                  95

Thr Val Glu Glu Gly Ile Ala Asp Glu Phe Met Ala Lys Leu Gln Glu
            100                 105                 110

Lys Val Ala Asp Ile Lys Ile Gly Asn Gly Leu Asp Asp Gly Val Phe
        115                 120                 125

Leu Gly Pro Val Ile Arg Glu Asp Asn Lys Lys Arg Thr His Ser Tyr
    130                 135                 140

Ile Glu Lys Gly Ile Glu Gly Ala Arg Leu Leu Cys Asp Gly Arg
145                 150                 155                 160

Glu Asn Ala Thr Glu Asp Gly Tyr Phe Val Gly Pro Thr Ile Phe Asp
                165                 170                 175

Asn Val Thr Thr Asp Met Ala Ile
            180

<210> SEQ ID NO 19
<211> LENGTH: 487
<212> TYPE: PRT
<213> ORGANISM: Bacillus amyloliquefaciens

<400> SEQUENCE: 19

Met Ala Glu Ile Arg Lys Leu Lys Asn Tyr Ile Asn Gly Glu Trp Val
1               5                   10                  15

Glu Ser Lys Thr Asp Gln Tyr Glu Asp Val Val Asn Pro Ala Thr Lys
            20                  25                  30

Glu Val Met Cys Gln Val Pro Ile Ser Thr Arg Glu Asp Val Glu Tyr
        35                  40                  45

Ala Val Arg Ser Ala Ser Glu Ala Phe Lys Thr Trp Ser Lys Thr Ala
    50                  55                  60

Val Pro Arg Arg Ala Arg Ile Leu Phe Asn Tyr Gln Gln Leu Leu Gln
65                  70                  75                  80

Gln Asn Lys Glu Glu Leu Ala Arg Leu Ile Thr Leu Glu Asn Gly Lys
                85                  90                  95

Asn Thr Thr Glu Ala Leu Gly Glu Val Gly Arg Gly Ile Glu Asn Val 100                 105                 110
Glu Phe Ala Ala Gly Ala Pro Ser Leu Met Met Gly Asp Ser Leu Ala
                115                 120                 125

Ser Ile Ala Thr Asp Val Glu Ala Ala Asn Tyr Arg Tyr Pro Ile Gly
    130                 135                 140

Val Val Gly Gly Ile Ala Pro Phe Asn Phe Pro Met Met Val Pro Cys
145                 150                 155                 160

Trp Met Phe Pro Met Ala Ile Ser Leu Gly Asn Thr Phe Ile Leu Lys
                165                 170                 175

Pro Ser Glu Arg Thr Pro Leu Leu Thr Glu Lys Leu Ala Glu Leu Phe
                180                 185                 190

Glu Gln Ala Gly Leu Pro Lys Gly Val Phe Asn Val Val His Gly Ala
            195                 200                 205

His Asp Val Val Asn Gly Ile Leu Glu His Pro Asp Ile Lys Ala Ile
        210                 215                 220

Ser Phe Val Gly Ser Lys Pro Val Gly Glu Tyr Val Phe Lys Lys Gly
225                 230                 235                 240

Ser Glu His Leu Lys Arg Val Gln Ala Leu Thr Gly Ala Lys Asn His
                245                 250                 255

Thr Ile Val Leu Asn Asp Ala His Leu Glu Asp Thr Val Thr Asn Ile
                260                 265                 270

Ile Gly Ala Ala Phe Gly Ser Ala Gly Glu Arg Cys Met Ala Cys Ala
            275                 280                 285

Val Val Thr Val Glu Glu Gly Ile Ala Asp Glu Phe Met Ala Lys Leu
        290                 295                 300

Gln Glu Lys Ala Ala Asp Ile Lys Leu Gly Asn Gly Leu Asp Asp Gly
305                 310                 315                 320

Val Phe Leu Gly Pro Val Ile Arg Glu Asp Asn Lys Lys Arg Thr His
                325                 330                 335

Ser Tyr Ile Glu Lys Gly Ile Glu Glu Gly Ala Arg Leu Leu Cys Asp
                340                 345                 350

Gly Arg Glu Asn Val Thr Glu Asp Gly Tyr Phe Val Gly Pro Thr Ile
            355                 360                 365

Phe Asp Asn Val Thr Thr Asp Met Thr Ile Trp Lys Asp Glu Ile Phe
        370                 375                 380

Ala Pro Val Leu Ser Val Ile Arg Val Lys Asn Leu Lys Glu Ala Val
385                 390                 395                 400

Asp Ile Ala Asn Gln Ser Glu Phe Ala Asn Gly Ala Cys Leu Phe Thr
                405                 410                 415

Ser Asn Ala Asn Ala Ile Arg Tyr Phe Arg Glu Asn Ile Asp Ala Gly
                420                 425                 430

Met Leu Gly Ile Asn Leu Gly Val Pro Ala Pro Met Ala Phe Phe Pro
            435                 440                 445

Phe Ser Gly Trp Lys Ser Ser Phe Phe Gly Thr Leu His Ala Asn Gly
        450                 455                 460

Lys Asp Ser Val Asp Phe Tyr Thr Arg Lys Lys Val Val Thr Ala Arg
465                 470                 475                 480

Tyr Pro Ser Pro Asp Phe Asn
                485

<210> SEQ ID NO 20
<211> LENGTH: 1089
<212> TYPE: DNA
<213> ORGANISM: Cuphea carthagenensis

<400> SEQUENCE: 20

```
atggcgaacg gtagcgctgt ctctctgaag agcggctcct tgaatacgca agaggacact        60
tcttcttccc caccgccacg cgcgttcatc aaccaattac ccgactggtc catgttattg       120
acggcgatta ccactgtctt tgttgccgca gagaaacagt ggactatgtt agaccgcaag       180
agcaagcgct ccgatatgtt agtggattct tttggcatgg aacgcattgt gcaggatggc       240
ttagtgtttc gtcaatcttt tagcattcgt tcttatgaaa tcggtgcaga tcgtcgtgca       300
tccattgaaa ccttaatgaa ccatctgcag gaaactagct tgaatcattg caaatccatt       360
cgcttgttga tgagggtttt ggtcgcaccc ccgagatgt gcaaacgtga cttgatctgg       420
gtggttaccc gcatgcacat catggtcaac cgctacccta cctggggtga taccgttgag       480
attaacactt gggtttccca aagcggcaag aatggtatgg tcgtgattg gctgatttcc       540
gactgtaata ccggcgaaat cctgatccgc gcgacgtctg catgggcgat gatgaaccaa       600
aagacccgtc gtctgtctaa actgccttac gaagtcagcc aagagattgc tccgcacttc       660
gtcgacagcc ctcccgtgat cgaggacggc gaccgtaagt tacacaagtt cgatgtgaaa       720
accggcgaca gcatccgtaa aggtttgact ccgcgttgga tgacttaga tgttaatcag       780
cacgttaaca acgttaagta tatcggctgg atcttagaga gcatgccgac cgaggtcttg       840
gaaactcatg aactgtgttt cttaactctg gagtatcgtc gcgagtgcgg tcgcgatagc       900
gtgctggaat ctgtgaccgc gatggatcct tctaatgaag gtggtcgctc ccactaccag       960
catttactgc gcttggagga cggtactgac atcgttaagg gccgcactga gtggcgtcca      1020
aagaatgccc ggaatattgg tgccattagt accggtaaaa ccagtaatgg taatcccgcc      1080
agttaataa                                                              1089
```

<210> SEQ ID NO 21
<211> LENGTH: 361
<212> TYPE: PRT
<213> ORGANISM: Cuphea carthagenensis

<400> SEQUENCE: 21

```
Met Ala Asn Gly Ser Ala Val Ser Leu Lys Ser Gly Ser Leu Asn Thr
1               5                   10                  15

Gln Glu Asp Thr Ser Ser Ser Pro Pro Arg Ala Phe Ile Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
    50                  55                  60

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
    130                 135                 140

Met His Ile Met Val Asn Arg Tyr Pro Thr Trp Gly Asp Thr Val Glu
145                 150                 155                 160
```

Ile Asn Thr Trp Val Ser Gln Ser Gly Lys Asn Gly Met Gly Arg Asp
               165                 170                 175

Trp Leu Ile Ser Asp Cys Asn Thr Gly Glu Ile Leu Ile Arg Ala Thr
           180                 185                 190

Ser Ala Trp Ala Met Met Asn Gln Lys Thr Arg Arg Leu Ser Lys Leu
       195                 200                 205

Pro Tyr Glu Val Ser Gln Glu Ile Ala Pro His Phe Val Asp Ser Pro
   210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
               245                 250                 255

Asp Val Asn Gln His Val Asn Asn Val Lys Tyr Ile Gly Trp Ile Leu
           260                 265                 270

Glu Ser Met Pro Thr Glu Val Leu Glu Thr His Glu Leu Cys Phe Leu
       275                 280                 285

Thr Leu Glu Tyr Arg Arg Glu Cys Gly Arg Asp Ser Val Leu Glu Ser
   290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
               325                 330                 335

Glu Trp Arg Pro Lys Asn Ala Arg Asn Ile Gly Ala Ile Ser Thr Gly
           340                 345                 350

Lys Thr Ser Asn Gly Asn Pro Ala Ser
       355                 360

<210> SEQ ID NO 22
<211> LENGTH: 90
<212> TYPE: DNA
<213> ORGANISM: Artificial Sequence
<220> FEATURE:
<223> OTHER INFORMATION: trcY promoter

<400> SEQUENCE: 22
ctgaaatgag ctgttgacaa ttaatcatcc ggctcgtata atgtgtggaa ttgtgagcgg    60
ataacaattt cacactaagg aggaaaaaaa                                    90

<210> SEQ ID NO 23
<211> LENGTH: 8645
<212> TYPE: DNA
<213> ORGANISM: Artificial Sequence
<220> FEATURE:
<223> OTHER INFORMATION: YC28 Integration Vector

<400> SEQUENCE: 23
gtctgacgct cagtggaacg aaaactcacg ttaagggatt ttggtcatga gattatcaaa    60
aaggatcttc acctagatcc ttttaaatta aaaatgaagt tttaaatcaa tctaaagtat   120
atatgagtaa acttggtctg acagttacca atgcttaatc agtgaggcac ctatctcagc   180
gatctgtcta tttcgttcat ccatagttgc ctgactcccc gtcgtgtaga taactacgat   240
acgggagggc ttaccatctg gccccagtgc tgcaatgata ccgcgagacc cacgctcacc   300
ggctccagat ttatcagcaa taaaccagcc agccggaagg gccgagcgca gaagtggtcc   360
tgcaacttta tccgcctcca tccagtctat taattgttgc cgggaagcta gagtaagtag   420
ttcgccagtt aatagtttgc gcaactgttg ggaagggcga tcggtgcggg cctcttcgct   480

-continued

```
attacgccag ctggcgaaag ggggatgtgc tgcaaggcga ttaagttggg taacgccagg    540
gttttcccag tcacgacgtt gtaaaacgac ggccagtgcc aagctattgc tgaagcggaa    600
tccctggtta atgccgccgc cgatgccaat tgcattctcc aagtggggca cattgaacgc    660
ttcaacccgg cattttaga gctaaccaaa attctcaaaa cggaagagtt attggcgatc     720
gaagcccatc gcatgagtcc ctattcccag cgggccaatg atgtctccgt ggtattggat    780
ttgatgatcc atgacattga cctgttgctg gaattggtgg gttcggaagt ggttaaactg    840
tccgccagtg gcagtcgggc ttctgggtca ggatatttgg attatgtcac cgctacgtta    900
ggcttctcct ccggcattgt ggccacctc accgccagta aggtcaccca tcgtaaaatt     960
cgttccatcg ccgcccactg caaaaattcc ctcaccgaag cggatttct caataacgaa    1020
attttgatcc atcgccaaac caccgctgat tggagcgcgg actatggcca ggtattgtat   1080
cgccaggatg gtctaatcga aaaggtttac accagtaata ttgaacctct ccacgctgaa   1140
ttagaacatt ttattcattg tgttagggga ggtgatcaac cctcagtggg gggagaacag   1200
gccctcaagg ccctgaagtt agccagttta attgaagaaa tggccctgga cagtcaggaa   1260
tggcatgggg gggaagttgt gacagaatat caagatgcca ccctggccct cagtgcgagt   1320
gtttaaatca acttaattaa tgcaattatt gcgagttcaa actcgataac tttgtgaaat   1380
attactgttg aattaatcta tgactattca atacaccccc ctagccgatc gcctgttggc   1440
ctacctcgcc gccgatcgcc taaatctcag cgccaagagt agttccctca acaccagtat   1500
tctgctcagc agtgacctat tcaatcagga agggggaatt gtaacagcca actatggctt   1560
tgatggttat atggtaccat atggtgcact ctcagtacaa tctgctctga tgccgcatag   1620
ttaagccagt atacactccg ctatcgctac gtgactgggt catggctgcg ccccgacacc   1680
cgccaacacc cgctgacgcg ccctgacggg cttgtctgct cccggcatcc gcttacagac   1740
aagctgtgac cgtctccggg agctgcatgt gtcagaggtt ttcaccgtca tcaccgaaac   1800
gcgcgaggca gcagatcaat tcgcgcgcga aggcgaagcg gcatgcattt acgttgacac   1860
catcgaatgg tgcaaaaacct ttcgcggtat ggcatgatag cgcccggaag agagtcaatt  1920
cagggtggtg aatgtgaaac cagtaacgtt atacgatgtc gcagagtatg ccggtgtctc   1980
ttatcagacc gtttcccgcg tggtgaacca ggccagccac gtttctgcga aaacgcggga   2040
aaaagtggaa gcggcgatgg cggagctgaa ttacattccc aaccgcgtgg cacaacaact   2100
ggcgggcaaa cagtcgttgc tgattggcgt tgccacctcc agtctggccc tgcacgcgcc   2160
gtcgcaaatt gtcgcggcga ttaaatctcg cgccgatcaa ctgggtgcca gcgtggtggt   2220
gtcgatggta gaacgaagcg gcgtcgaagc ctgtaaagcg gcggtgcaca atcttctcgc   2280
gcaacgcgtc agtgggctga tcattaacta tccgctggat gaccaggatg ccattgctgt   2340
ggaagctgcc tgcactaatg ttccggcgtt atttcttgat gtctctgacc agacacccat   2400
caacagtatt attttctccc atgaagacgt tacgcgactg ggcgtggagc atctggtcgc   2460
attgggtcac cagcaaatcg cgctgttagc gggcccatta agttctgtct cggcgcgtct   2520
gcgtctggct ggctggcata atatctcac tcgcaatcaa attcagccga tagcggaacg   2580
ggaaggcgac tggagtgcca tgtccggttt tcaacaaacc atgcaaatgc tgaatgaggg   2640
catcgttccc actgcgatgc tggttgccaa cgatcagatg gcgctgggcg caatgcgcgc   2700
cattaccgag tccgggctgc gcgttggtgc ggatatctcg gtagtgggat acgacgatac   2760
cgaagacagc tcatgttata tcccgccgtt aaccaccatc aaacaggatt ttcgcctgct   2820
ggggcaaacc agcgtggacc gcttgctgca actctctcag ggccaggcgg tgaagggcaa   2880
```

```
tcagctgttg cccgtctcac tggtgaaaag aaaaaccacc ctggcgccca atacgcaaac    2940
cgcctctccc cgcgcgttgg ccgattcatt aatgcagctg gcacgacagg tttcccgact    3000
ggaaagcggg cagtgagcgc aacgcaatta atgtaagtta gcgcgaattg atctggtttg    3060
acagcttatc atcgactgca cggtgcacca atgcttctgg cgtcaggcag ccatcggaag    3120
ctgtggtatg gctgtgcagg tcgtaaatca ctgcataatt cgtgtcgctc aaggcgcact    3180
cccgttctgg ataatgtttt ttgcgccgac atcataacgg ttctggcaaa tattctgaaa    3240
tgagctgttg acaattaatc atccggctcg tataatgtgt ggaattgtga gcggataaca    3300
atttcacaca ggaaacagcg ccgctgagaa aaagcgaagc ggcactgctc tttaacaatt    3360
tatcagacaa tctgtgtggg cactcgaccg gaattatcga ttaactttat tattaaaaat    3420
taaagaggta tatattaatg tatcgattaa ataaggagga ataaaccatg gcgaatggtt    3480
ctgcagtctc tttgaaatct ggaagcttga atacgcagga ggatactagt tccagtcccc    3540
ctcctcggac gttttttgcat cagctgcccg actggagtcg cttgctgacc gccatcacaa    3600
cagtgtttgt caaatctaaa cgaccggaca tgcatgatcg gaaaagcaag cgcccagata    3660
tgctcgtcga tagtttcgga ctcgagtcta ctgtgcagga cggcctggtg ttccgtcaat    3720
ccttcagcat ccgaagctac gagattggta cggaccgtac cgctagcatt gaaacgttga    3780
tgaaccatct ccaagaaacc agtttgaacc actgcaagag cacgggcatc ctgctggatg    3840
gttttggccg cacattggaa atgtgcaagc gagacttgat ctgggtggtc attaaaatgc    3900
agatcaaagt taatcgatac ccggcctggg gagataccgt tgagatcaat acacgctttt    3960
cccgtttggg caaaattggc atgggtcgcg attggctgat ctccgactgc aacaccggtg    4020
agatcttggt ccgtgcaacg tctgcgtacg cgatgatgaa tcaaaagacg cgtcggttga    4080
gtaagctgcc gtatgaagtt caccaagaaa ttgttccatt gttcgttgat agtcccgtta    4140
tcgaggattc tgacctcaaa gtccacaagt ttaaagtcaa gactggcgat tccatccaga    4200
agggcctgac gccaggttgg aacgatctgg atgtgaacca acacgttagc aacgttaagt    4260
atatcggctg gatcttggaa agtatgccta cggaagtcct ggagacgcag gaactctgca    4320
gtctcgctct ggagtaccgc cgtgagtgtg gccgtgattc cgtgctcgag tccgtcactg    4380
cgatggaccc tagcaaagtg ggtgttcgca gtcaatacca acacctcttg cggctcgaag    4440
atgggaccgc cattgtgaac ggcgcgaccg aatggcgccc caaaaatgcc ggcgctaacg    4500
gggcaattag taccgggaaa acctccaatg gaaacagcgt cagctaatga taggatccga    4560
gctcagatct accaggttgt ccttggcgca gcgcttccca cgctgagagg gtgtagcccg    4620
tcacgggtaa ccgatatcgt cgacaggcct ctagacccgg gctcgagcta gcaagcttgg    4680
ccggatccgg ccggatccgg agtttgtaga acgcaaaaa ggccatccgt caggatggcc    4740
ttctgcttaa tttgatgcct ggcagtttat ggcgggcgtc ctgcccgcca ccctccgggc    4800
cgttgcttcg caacgttcaa atccgctccc ggcggatttg tcctactcag gagagcgttc    4860
accgacaaac aacagataaa acgaaaggcc cagtctttcg actgagcctt tcgttttatt    4920
tgatgcctgg cagttcccta ctctcgcatg gggagacccc acactaccat cggcgctacg    4980
gcgtttcact tctgagttcg gcatggggtc aggtgggacc accgcgctac tgccgccagg    5040
caaattctgt tttattgagc cgttacccca cctactagct aatcccatct gggcacatcc    5100
gatggcaaga ggcccgaagg tccccctctt tggtcttgcg acgttatgcg gtattagcta    5160
ccgtttccag tagttatccc cctccatcag gcagtttccc agacattact cacccgtccg    5220
```

```
ccactcgtca gcaaagaagc aagcttagat cgacctgcag ggggggggggg gaaagccacg    5280
ttgtgtctca aaatctctga tgttacattg cacaagataa aaatatatca tcatgaacaa    5340
taaaactgtc tgcttacata aacagtaata caaggggtgt tatgagccat attcaacggg    5400
aaacgtcttg ctcgaggccg cgattaaatt ccaacatgga tgctgattta tatgggtata    5460
aatgggctcg cgataatgtc gggcaatcag gtgcgacaat ctatcgattg tatgggaagc    5520
ccgatgcgcc agagttgttt ctgaaacatg gcaaaggtag cgttgccaat gatgttacag    5580
atgagatggt cagactaaac tggctgacgg aatttatgcc tcttccgacc atcaagcatt    5640
ttatccgtac tcctgatgat gcatggttac tcaccactgc gatccccggg aaaacagcat    5700
tccaggtatt agaagaatat cctgattcag gtgaaaatat tgttgatgcg ctggcagtgt    5760
tcctgcgccg gttgcattcg attcctgttt gtaattgtcc ttttaacagc gatcgcgtat    5820
ttcgtctcgc tcaggcgcaa tcacgaatga ataacggttt ggttgatgcg agtgattttg    5880
atgacgagcg taatgctggg cctgttgaac aagtctggaa agaaatgcat aagcttttgc    5940
cattctcacc ggattcagtc gtcactcatg gtgatttctc acttgataac cttatttttg    6000
acgaggggaa attaataggt tgtattgatg ttggacgagt cggaatcgca gaccgatacc    6060
aggatcttgc catcctatgg aactgcctcg gtgagttttc tccttcatta cagaaacggc    6120
tttttcaaaa atatggtatt gataatcctg atatgaataa attgcagttt catttgatgc    6180
tcgatgagtt tttctaatca gaattggtta attggttgta acactggcag agcattacgc    6240
tgacttgacg ggacggcggc tttgttgaat aaatcgaact tttgctgagt tgaaggatca    6300
gatcacgcat cttcccgaca acgcagaccg ttccgtggca aagcaaaagt tcaaaatcac    6360
caactggtcc acctacaaca aagctctcat caaccgtggc tccctcactt tctggctgga    6420
tgatggggcg attcaggcct ggtatgagtc agcaacacct tcttcacgag gcagacctca    6480
gcgcccccccc ccccctgcag gtcgatctgg taacccagcg gcggttgcta ccaagtagtg    6540
acccgcttcg tgatgcaaaa tccgctgacg atattcgggc gatcgctgct gaatgccatc    6600
gagcagtaac gtggcgaatt cggtaccggt atggatggca ccgatgcgga atcccaacag    6660
attgcctttg acaacaatgt ggcctggaat aacctggggg attgtccac caccaccccaa    6720
cgggcctaca cttcggctat tagcacagac acagtgcaga gtgtttatgg cgttaatctg    6780
gaaaaaaacg ataacattcc cattgttttt gcgtggccca tttttcccac cacccttaat    6840
cccacagatt ttcaggtaat gcttaacacg ggggaaattg tcaccccggt gatcgcctct    6900
ttgattccca acagtgaata caacgaacgg caaacggtag taattacggg caattttggt    6960
aatcgtttaa ccccaggcac ggagggagcg atttatcccg tttccgtagg cacagtgttg    7020
gacagtactc ctttggaaat ggtgggaccc aacggcccgg tcagtgcggt gggtattacc    7080
attgatagtc tcaacccctta cgtggccggc aatggtccca aaattgtcgc cgctaagtta    7140
gaccgcttca gtgacctggg gaaggggct cccctctggt tagccaccaa tcaaaataac    7200
agtggcgggg atttatatgg agaccaagcc caatttcgtt tgcgaattta caccagcgcc    7260
ggttttttccc ccgatggcat tgccagtttta ctacccacag aatttgaacg gtattttcaa    7320
ctccaagcgg aagatattac gggacggaca gttatcctaa cccaaactgg tgttgattat    7380
gaaattcccg ctttggtct ggtgcaggtg ttggggctgg cggatttggc cggggttcag    7440
gacagctatg acctgactta catcgaagat catgacaact attacgacat tatcctcaaa    7500
ggggacgaag ccgcagttcg ccaaattaag agggttgctt tgccctccga aggggattat    7560
tcggcggttt ataatcccgg tggccccggc aatgatccag agaatggtcc cccaaattcg    7620
```

-continued

| | |
|---|---|
| taatcatggt catagctgtt tcctgtgtga aattgttatc cgctcacaat tccacacaac | 7680 |
| atacgagccg gaagcataaa gtgtaaagcc tggggtgcct aatgagtgag ctaactcaca | 7740 |
| ttaattgcgt tgcgctcact gcccgctttc cagtcgggaa acctgtcgtg ccagctgcat | 7800 |
| taatgaatcg gccaacgcgc ggggagaggc ggtttgcgta ttgggcgctc ttccgcttcc | 7860 |
| tcgctcactg actcgctgcg ctcggtcgtt cggctgcggc gagcggtatc agctcactca | 7920 |
| aaggcggtaa tacggttatc cacagaatca ggggataacg caggaaagaa catgtgagca | 7980 |
| aaaggccagc aaaaggccag gaaccgtaaa aaggccgcgt tgctggcgtt tttccatagg | 8040 |
| ctccgccccc ctgacgagca tcacaaaaat cgacgctcaa gtcagaggtg gcgaaacccg | 8100 |
| acaggactat aaagatacca ggcgtttccc cctggaagct ccctcgtgcg ctctcctgtt | 8160 |
| ccgaccctgc cgcttaccgg atacctgtcc gcctttctcc cttcgggaag cgtggcgctt | 8220 |
| tctcatagct cacgctgtag gtatctcagt tcggtgtagg tcgttcgctc caagctgggc | 8280 |
| tgtgtgcacg aaccccccgt tcagcccgac cgctgcgcct tatccggtaa ctatcgtctt | 8340 |
| gagtccaacc cggtaagaca cgacttatcg ccactggcag cagccactgg taacaggatt | 8400 |
| agcagagcga ggtatgtagg cggtgctaca gagttcttga agtggtggcc taactacggc | 8460 |
| tacactagaa ggacagtatt tggtatctgc gctctgctga gccagttacc ttcggaaaa | 8520 |
| agagttggta gctcttgatc cggcaaacaa accaccgctg gtagcggtgg tttttttgtt | 8580 |
| tgcaagcagc agattacgcg cagaaaaaaa ggatctcaag aagatccttt gatcttttct | 8640 |
| acggg | 8645 |

<210> SEQ ID NO 24
<211> LENGTH: 989
<212> TYPE: DNA
<213> ORGANISM: Synechocystis PCC6803

<400> SEQUENCE: 24

| | |
|---|---|
| attgctgaag cggaatccct ggttaatgcc gccgccgatg ccaattgcat tctccaagtg | 60 |
| gggcacattg aacgcttcaa cccggcattt ttagagctaa ccaaaattct caaaacggaa | 120 |
| gagttattgg cgatcgaagc ccatcgcatg agtccctatt cccagcgggc caatgatgtc | 180 |
| tccgtggtat tggatttgat gatccatgac attgacctgt tgctggaatt ggtgggttcg | 240 |
| gaagtggtta aactgtccgc cagtggcagt cgggcttctg ggtcaggata tttggattat | 300 |
| gtcaccgcta cgttaggctt ctcctccggc attgtggcca ccctcaccgc cagtaaggtc | 360 |
| acccatcgta aaattcgttc catcgccgcc cactgcaaaa attccctcac cgaagcggat | 420 |
| tttctcaata cgaaattttt gatccatcgc caaaccaccg ctgattggag cgcggactat | 480 |
| ggccaggtat tgtatcgcca ggatggtcta atcgaaaagg tttacaccag taatattgaa | 540 |
| cctctccacg ctgaattaga acattttatt cattgtgtta ggggaggtga tcaaccctca | 600 |
| gtgggggagg aacaggccct caaggccctg aagttagcca gtttaattga agaaatggcc | 660 |
| ctggacagtc aggaatggca tgggggggaa gttgtgacag aatatcaaga tgccaccctg | 720 |
| gccctcagtg cgagtgttta aatcaactta ttaatgcaa ttattgcgag ttcaaactcg | 780 |
| ataactttgt gaaatattac tgttgaatta atctatgact attcaataca ccccctagc | 840 |
| cgatcgcctg ttggcctacc tcgccgccga tcgcctaaat ctcagcgcca agagtagttc | 900 |
| cctcaacacc agtattctgc tcagcagtga cctattcaat caggaagggg gaattgtaac | 960 |
| agccaactat ggctttgatg gttatatgg | 989 |

<210> SEQ ID NO 25
<211> LENGTH: 989
<212> TYPE: DNA
<213> ORGANISM: Synechocystis PCC6803

<400> SEQUENCE: 25

```
ccggtatgga tggcaccgat gcggaatccc aacagattgc ctttgacaac aatgtggcct      60
ggaataacct gggggatttg tccaccacca cccaacgggc ctacacttcg gctattagca     120
cagacacagt gcagagtgtt tatggcgtta atctggaaaa aaacgataac attcccattg     180
tttttgcgtg gcccattttt cccaccaccc ttaatcccac agattttcag gtaatgctta     240
acacggggga aattgtcacc ccggtgatcg cctctttgat tcccaacagt gaatacaacg     300
aacggcaaac ggtagtaatt acgggcaatt ttggtaatcg tttaaccccca ggcacggagg     360
gagcgattta tcccgtttcc gtaggcacag tgttggacag tactcctttg gaaatggtgg     420
gacccaacgg cccggtcagt gcggtgggta ttaccattga tagtctcaac ccctacgtgg     480
ccggcaatgg tcccaaaatt gtcgccgcta agttagaccc cttcagtgac ctgggggaag     540
gggctcccct ctggttagcc accaatcaaa ataacagtgg cggggattta tatggagacc     600
aagcccaatt tcgtttgcga atttacacca gcgccggttt ttccccccgat ggcattgcca     660
gtttactacc cacagaattt gaacggtatt ttcaactcca agcggaagat attacgggac     720
ggacagttat cctaacccaa actggtgttg attatgaaat tcccggcttt ggtctggtgc     780
aggtgttggg gctggcggat ttggccgggg ttcaggacag ctatgacctg acttacatcg     840
aagatcatga caactattac gacattatcc tcaaggggga cgaagccgca gttcgccaaa     900
ttaagagggt tgctttgccc tccgaagggg attattcggc ggtttataat cccggtggcc     960
ccggcaatga tccagagaat ggtccccca                                       989
```

<210> SEQ ID NO 26
<211> LENGTH: 1032
<212> TYPE: DNA
<213> ORGANISM: Synechocystis PCC6803

<400> SEQUENCE: 26

```
tatttgcccg tattctgccc tatccccaag ccctagccca ggcgatcgcc gctgggttta      60
cttccgaccg tatcattgct ttgcgccccc ccgtagccga accattggaa aaagccctgt     120
ggcaacaatg gcaaattcaa ggggtggtaa ctaaagcctc cggtgcccag gggggagaat     180
tggttaagca aaaagtggcg gaagcgttgg gggtaaatct gatcagaatt gcccgtcccc     240
agactattcc agggcaaata actgacgatt taagccagat caaccaattt tgccaaagac     300
atttgccaag ctaaaaacga aaatttgtta agtattgcaa cggtggtttc ccaggggcag     360
agcgtccccg taagatgaga tttttaaaga ccccccattag cgtggggcta tcccctttaaa    420
aaccgtcttt attctggaga atctcaatgc atagcttttt gttggccacc gccgttcccg     480
ccaccctgtc ctggagccct aaagttgctg gggtgatgat tgcttgcaac attttggcga     540
tcgcctttgg taaattgacc atcaaacaac aaaatgtggg caccccccatg ccttcctcta    600
acttctttgg cggctttggt ttaggggctg tgctgggcac cgctagcttt ggccacatcc     660
tcggcgctgg agtaattctg gggctagcca atatgggagt actttaaggc tcgattctga     720
atggactagc ttttatccctt tgggaaaata tcaaaggcga tcgggcaatt gaaagaaaag     780
cctggtcgct tttttgttag ggattaggga aaatgccaaa acgcaccaag gtggtaatta     840
tggctccgat gacggcaaga atcaacgccc aaatttgagc attagcccgc cctttgacat     900
```

| | |
|---|---|
| ctttaacatc atccttgact gtacctatct ccatcctgac cgcagataac tcggttttca | 960 |
| ccgttgccat atcgatctta agagaagtta catcttttg gaggtcatcg agtttggtct | 1020 |
| taatttcccc ca | 1032 |

<210> SEQ ID NO 27
<211> LENGTH: 824
<212> TYPE: DNA
<213> ORGANISM: Synechocystis PCC6803

<400> SEQUENCE: 27

| | |
|---|---|
| cctttaaatc ggtttctata gttacactca ttggcttttg cctgcaaagc aatatttcct | 60 |
| gataccccta gggtaaatca tgggaaatgg cgatcgccgg agtttctcct gtttgctgga | 120 |
| gggctgtctg caacatcttg gtgctgacca cggaatcggt ggcgaggtta agaggggat | 180 |
| tagccagaat acctgccagc gaggtagcaa ccaaagtagc gacaatgccc acctgtaggg | 240 |
| gacgcatgcc gggtaaattc catttgatgg ccgggtaatt tttgattact tcggacattt | 300 |
| cctggggctc cttcaccacc atcattttca ccacccggat gtagtagtag atggaaacta | 360 |
| cactggtaac cagaccaagt aggactaggc catacaatcc cgattgccaa ccggcccaga | 420 |
| agatgtaaat tttgccgaaa agcccgcca gaggaggaat gcccccaag gataataaac | 480 |
| aaatgctcaa gcccaaggtt aacaagggg ctttgtggta cagaccagcg taatcactaa | 540 |
| tttggtcact gccagtgcgg agggtgaaga gaataatgca actaaacgcc cccaggttca | 600 |
| taaacagata gatgagcatg tagaaaacca tgctggcgta accatcttca ctgccggcca | 660 |
| ctaggccaat catcacaaag cctgcttgac cgatggaaga gtaggccaac atccgtttca | 720 |
| tgctggtttg ggctaaagcc accacgttgc ccagcaccat gctcaacacg gccagagcgg | 780 |
| tgaaaataac gtgccactca tcggtaatac caccaaaggc agtc | 824 |

<210> SEQ ID NO 28
<211> LENGTH: 8572
<212> TYPE: DNA
<213> ORGANISM: Artificial Sequence
<220> FEATURE:
<223> OTHER INFORMATION: YC63 Integration Vector

<400> SEQUENCE: 28

| | |
|---|---|
| cagttaccaa tgcttaatca gtgaggcacc tatctcagcg atctgtctat ttcgttcatc | 60 |
| catagttgcc tgactccccg tcgtgtagat aactacgata cgggagggct taccatctgg | 120 |
| ccccagtgct gcaatgatac cgcgagaccc acgctcaccg gctccagatt tatcagcaat | 180 |
| aaaccagcca gccggaaggg ccgagcgcag aagtggtcct gcaactttat ccgcctccat | 240 |
| ccagtctatt aattgttgcc gggaagctag agtaagtagt tcgccagtta atagtttgcg | 300 |
| caactgttgg gaaggcgat cggtgcgggc ctcttcgcta ttacgccagc tggcgaaagg | 360 |
| gggatgtgct gcaaggcgat taagttgggt aacgccaggg ttttcccagt cacgacgttg | 420 |
| taaaacgacg gccagtgaat tgggcccgac tgcctttggt ggtattaccg atgagtggca | 480 |
| cgttattttc accgctctgg ccgtgttgag catggtgctg gcaacgtgg tggctttagc | 540 |
| ccaaccagc atgaaacgga tgttggccta ctcttccatc ggtcaagcag gctttgtgat | 600 |
| gattggccta gtggccggca gtgaagatgg ttacgccagc atggttttct acatgctcat | 660 |
| ctatctgttt atgaacctgg gggcgttag ttgcattatt ctcttcaccc tccgcactgg | 720 |
| cagtgaccaa attagtgatt acgctggtct gtaccacaaa gaccccttgt taaccttggg | 780 |

```
cttgagcatt tgtttattat ccttgggggg cattcctcct ctggcgggct ttttcggcaa    840
aatttacatc ttctgggccg gttggcaatc gggattgtat ggcctagtcc tacttggtct    900
ggttaccagt gtagtttcca tctactacta catccgggtg gtgaaaatga tggtggtgaa    960
ggagccccag gaaatgtccg aagtaatcaa aaattacccg gccatcaaat ggaatttacc   1020
cggcatgcgt ccctacagg tgggcattgt cgctactttg gttgctacct cgctggcagg   1080
tattctggct aatcccctct ttaacctcgc caccgattcc gtggtcagca ccaagatgtt   1140
gcagacagcc ctccagcaaa caggagaaac tccggcgatc gccatttccc atgatttacc   1200
ctaggggtat caggaaatat tgctttgcag gcaaaagcca atgagtgtaa ctatagaaac   1260
cgatttaaag gagatccact agtcctgagg ctgaaatgag ctgttgacaa ttaatcatcc   1320
ggctcgtata atgtgtggaa ttgtgagcgg ataacaattt cacactaagg aggaaaaaaa   1380
ccatggaaga cgccaaaaac ataaagaaag gcccggcgcc attctatccg ctggaagatg   1440
gaaccgctgg agagcaactg cataaggcta tgaagagata cgccctggtt cctggaacaa   1500
ttgcttttac agatgcacat atcgaggtgg acatcactta cgctgagtac ttcgaaatgt   1560
ccgttcggtt ggcagaagct atgaaacgat atgggctgaa tacaaatcac agaatcgtcg   1620
tatgcagtga aaactctctt caattcttta tgccggtgtt gggcgcgtta tttatcggag   1680
ttgcagttgc gcccgcgaac gacatttata tgaacgtga attgctcaac agtatgggca   1740
tttcgcagcc taccgtggtg ttcgtttcca aaaggggtt gcaaaaaatt ttgaacgtgc   1800
aaaaaaagct cccaatcatc caaaaaatta ttatcatgga ttctaaaacg gattaccagg   1860
gatttcagtc gatgtacacg ttcgtcacat ctcatctacc tcccggtttt aatgaatacg   1920
attttgtgcc agagtccttc gatagggaca gacaattgc actgatcatg aactcctctg   1980
gatctactgg tctgcctaaa ggtgtcgctc tgcctcatag aactgcctgc gtgagattct   2040
cgcatgccag agatcctatt tttggcaatc aaatcattcc ggatactgcg attttaagtg   2100
ttgttccatt ccatcacggt tttggaatgt ttactacact cggatatttg atatgtggat   2160
ttcgagtcgt cttaatgtat agatttgaag aagagctgtt tctgaggagc cttcaggatt   2220
acaagattca aagtgcgctg ctggtgccaa cccctattctc cttcttcgcc aaaagcactc   2280
tgattgacaa atacgattta tctaatttac acgaaattgc ttctggtggc gctccctct   2340 ctaaggaagt cggggaagcg gttgccaaga ggttccatct gccaggtatc aggcaaggat   2400
atgggctcac tgagactaca tcagctattc tgattacacc cgagggggat gataaaccgg   2460
gcgcggtcgg taaagttgtt ccattttttg aagcgaaggt tgtggatctg gataccggga   2520
aaacgctggg cgttaatcaa agaggcgaac tgtgtgtgag aggtcctatg attatgtccg   2580
gttatgtaaa caatccggaa gcgaccaacg ccttgattga caaggatgga tggctacatt   2640
ctggagacat agcttactgg gacgaagacg aacacttctt catcgttgac cgcctgaagt   2700
ctctgattaa gtacaaaggc tatcaggtgg ctcccgctga attggaatcc atcttgctcc   2760
aacaccccaa catcttcgac gcaggtgtcg caggtcttcc cgacgatgac gccggtgaac   2820
ttcccgccgc cgttgttgtt ttggagcacg gaaagacgat gacggaaaaa gagatcgtgg   2880
attacgtcgc cagtcaagta acaaccgcga aaaagttgcg cggaggagtt gtgtttgtgg   2940
acgaagtacc gaaaggtctt accggaaaac tcgacgcaag aaaaatcaga gagatcctca   3000
taaaggccaa gaagggcgga aagatcgccg tgtaattcta gatatctgca ggcctaagct   3060
ttatgcttgt aaaccgtttt gtgaaaaaat ttttaaaata aaaaggggga cctctagggt   3120
ccccaattaa ttagtaatat aatctattaa aggtcattca aaaggtcatc caccggatca   3180
```

| | |
|---|---|
| attcccctgc tcgcgcaggc tgggtgccag gcccgatcct tggagccctt gccctcccgc | 3240 |
| acgatgatcg tgccgtgatc gaaatccaga tccttgaccc gcagttgcaa accctcactg | 3300 |
| atccgcatgc ccgttccata cagaagctgg gcgaacaaac gatgctcgcc ttccagaaaa | 3360 |
| ccgaggatgc gaaccacttc atccggggtc agcaccaccg gcaagcgccg cgacggccga | 3420 |
| ggtcttccga tctcctgaag ccagggcaga tccgtgcaca gcaccttgcc gtagaagaac | 3480 |
| agcaaggccg ccaatgcctg acgatgcgtg agaccgaaa ccttgcgctc gttcgccagc | 3540 |
| caggacagaa atgcctcgac ttcgctgctg cccaaggttg ccgggtgacg cacaccgtgg | 3600 |
| aaacggatga aggcacgaac ccagtggaca taagcctgtt cggttcgtaa gctgtaatgc | 3660 |
| aagtagcgta tgcgctcacg caactggtcc agaaccttga ccgaacgcag cggtggtaac | 3720 |
| ggcgcagtgg cggttttcat ggcttgttat gactgttttt ttggggtaca gtctatgcct | 3780 |
| cggtcgggca tccaagcagc aagcgcgtta cgccgtgggt cgatgtttga tgttatggag | 3840 |
| cagcaacgat gttacgcagc agggcagtcg ccctaaaaca aagttaaaca tcatgaggga | 3900 |
| agcggtgatc gccgaagtat cgactcaact atcagaggta gttggcgtca tcgagcgcca | 3960 |
| tctcgaaccg acgttgctgg ccgtacattt gtacggctcc gcagtggatg gcggcctgaa | 4020 |
| gccacacagt gatattgatt tgctggttac ggtgaccgta aggcttgatg aaacaacgcg | 4080 |
| gcgagctttg atcaacgacc ttttggaaac ttcggcttcc cctggagaga gcgagattct | 4140 |
| ccgcgctgta gaagtcacca ttgttgtgca cgacgacatc attccgtggc gttatccagc | 4200 |
| taagcgcgaa ctgcaatttg gagaatggca gcgcaatgac attcttgcag gtatcttcga | 4260 |
| gccagccacg atcgacattg atctggctat cttgctgaca aaagcaagag aacatagcgt | 4320 |
| tgccttggta ggtccagcgg cggaggaact ctttgatccg gttcctgaac aggatctatt | 4380 |
| tgaggcgcta aatgaaacct taacgctatg gaactcgccg cccgactggg ctggcgatga | 4440 |
| gcgaaatgta gtgcttacgt tgtcccgcat ttggtacagc gcagtaaccg gcaaaatcgc | 4500 |
| gccgaaggat gtcgctgccg actgggcaat ggagcgcctg ccggcccagt atcagcccgt | 4560 |
| catacttgaa gctagacagg cttatcttgg acaagaagaa gatcgcttgg cctcgcgcgc | 4620 |
| agatcagttg gaagaatttg tccactacgt gaaaggcgag atcaccaagg tagtcggcaa | 4680 |
| ataatgtcta acaattcgtt caagccgacg ccgcttcgcg gcgcggctta actcaagcgt | 4740 |
| tagatgcact aagcacataa ttgctcacag ccaaactatc aggtcaagtc tgcttttatt | 4800 |
| attttaagc gtgcataata agccctacac aaattgggag atatatcatg aaaggctggc | 4860 |
| tttttcttgt tatcgcaata gttggcgaag taatcgcaac atccgcatta aaatctagcg | 4920 |
| agggctttac taagctgatc cggtggatga ccttttgaat gacctttaat agattatatt | 4980 |
| actaattaat tggggaccct agaggtcccc ttttttattt taaaaatttt ttcacaaaac | 5040 |
| ggtttacaag cataaagctt ccgcggtacc cgggaattcg cccttcaag cttcagatca | 5100 |
| attcgcgcta acttacatta attgcgttgc gctcactgcc cgctttccag tcgggaaacc | 5160 |
| tgtcgtgcca gctgcattaa tgaatcggcc aacgcgcggg gagaggcggt ttgcgtattg | 5220 |
| ggcgccaggg tggtttttct tttcaccagt gagacgggca acagctgatt gcccttcacc | 5280 |
| gcctggccct gagagagttg cagcaagcgg tccacgctgg tttgccccag caggcgaaaa | 5340 |
| tcctgtttga tggtggttaa cggcgggata taacatgagc tgtcttcggt atcgtcgtat | 5400 |
| cccactaccg agatatccgc accaacgcgc agcccgact cggtaatggc gcgcattgcg | 5460 |
| cccagcgcca tctgatcgtt ggcaaccagc atcgcagtgg gaacgatgcc ctcattcagc | 5520 |

```
atttgcatgg tttgttgaaa accggacatg gcactccagt cgccttcccg ttccgctatc   5580
ggctgaattt gattgcgagt gagatattta tgccagccag ccagacgcag acgcgccgag   5640
acagaactta atgggcccgc taacagcgcg atttgctggt gacccaatgc gaccagatgc   5700
tccacgccca gtcgcgtacc gtcttcatgg gagaaaataa tactgttgat gggtgtctgg   5760
tcagagacat caagaaataa cgccggaaca ttagtgcagg cagcttccac agcaatggca   5820
tcctggtcat ccagcggata gttaatgatc agcccactga cgcgttgcgc gagaagattg   5880
tgcaccgccg ctttacaggc ttcgacgccg cttcgttcta ccatcgacac caccacgctg   5940
gcacccagtt gatcggcgcg agatttaatc gccgcgacaa tttgcgacgg cgcgtgcagg   6000
gccagactgg aggtggcaac gccaatcagc aacgactgtt tgcccgccag ttgttgtgcc   6060
acgcggttgg gaatgtaatt cagctccgcc atcgccgctt ccactttttc ccgcgttttc   6120
gcagaaacgt ggctggcctg gttcaccacg cgggaaacgg tctgataaga gacaccggca   6180
tactctgcga catcgtataa cgttactggt ttcacattca ccaccctgaa ttgactctct   6240
tccgggcgct atcatgccat accgcgaaag gttttgcacc attcgatggt gtcaacgtaa   6300
atgcatgccg cttcgccttc gcgcaagctt agaagggcga attccggaca tatggatctt   6360
gggggaaatt aagaccaaac tcgatgacct ccaaaaagat gtaacttctc ttaagatcga   6420
tatggcaacg gtgaaaaccg agttatctgc ggtcaggatg gagataggta cagtcaagga   6480
tgatgttaaa gatgtcaaag gcgggctaa tgctcaaatt gggcgttga ttcttgccgt   6540
catcggagcc ataattacca ccttggtgcg ttttggcatt ttccctaatc cctaacaaaa   6600
aagcgaccag gcttttcttt caattgcccg atcgcctttg atattttccc aaaggataaa   6660
agctagtcca ttcagaatcg agccttaaag tactcccata ttggctagcc ccagaattac   6720
tccagcgccg aggatgtggc caaagctagc ggtgcccagc acagcccta aaccaaagcc   6780
gccaaagaag ttagaggaag catgggggt gcccacattt tgttgtttga tggtcaattt   6840
accaaaggcg atcgccaaaa tgttgcaagc aatcatcacc ccagcaactt tagggctcca   6900
ggacagggtg gcgggaacgg cggtggccaa caaaaagcta tgcattgaga ttctccagaa   6960
taaagacggt ttttaaaggg atagccccac gctaatgggg gtctttaaaa atctcatctt   7020
acggggacgc tctgcccctg ggaaaccacc gttgcaatac ttaacaaatt ttcgttttta   7080
gcttggcaaa tgtcttttggc aaaattggtt gatctggctt aaatcgtcag ttatttgccc   7140
tggaatagtc tggggacggg caattctgat cagatttacc cccaacgctt ccgccacttt   7200
ttgcttaacc aattctcccc cctgggcacc ggaggcttta gttaccaccc cttgaatttg   7260
ccattgttgc cacagggctt tttccaatgg ttcggctacg gggggggcgca aagcaatgat   7320
acggtcggaa gtaaacccag cggcgatcgc ctgggctagg gcttggggat agggcagaat   7380
acgggcaaat agggcccagc ttggcgtaat catggtcata gctgtttcct gtgtgaaatt   7440
gttatccgct cacaattcca cacaacatac gagccggaag cataaagtgt aaagcctggg   7500
gtgcctaatg agtgagctaa ctcacattaa ttgcgttgcg ctcactgccc gctttccagt   7560
cgggaaacct gtcgtgccag ctgcattaat gaatcggcca acgcgcgggg agaggcggtt   7620
tgcgtattgg gcgctcttcc gcttcctcgc tcactgactc gctgcgctcg tcgttcggc   7680
tgcggcgagc ggtatcagct cactcaaagg cggtaatacg ttatccaca gaatcagggg   7740
ataacgcagg aaagaacatg tgagcaaaag gccagcaaaa ggccaggaac cgtaaaaagg   7800
ccgcgttgct ggcgtttttc cataggctcc gccccctga cgagcatcac aaaaatcgac   7860
gctcaagtca gaggtggcga aacccgacag gactataaag ataccaggcg tttccccctg   7920
```

-continued

```
gaagctccct cgtgcgctct cctgttccga ccctgccgct taccggatac ctgtccgcct    7980
ttctcccttc gggaagcgtg gcgctttctc atagctcacg ctgtaggtat ctcagttcgg    8040
tgtaggtcgt tcgctccaag ctgggctgtg tgcacgaacc ccccgttcag cccgaccgct    8100 gcgcctatc cggtaactat cgtcttgagt ccaacccggt aagacacgac ttatcgccac     8160
tggcagcagc cactggtaac aggattagca gagcgaggta tgtaggcggt gctacagagt    8220
tcttgaagtg gtggcctaac tacgctaca ctagaaggac agtatttggt atctgcgctc     8280
tgctgaagcc agttaccttc ggaaaaagag ttggtagctc ttgatccggc aaacaaacca    8340
ccgctggtag cggtggtttt tttgtttgca agcagcagat tacgcgcaga aaaaaggat     8400 ctcaagaaga tcctttgatc ttttctacgg ggtctgacgc tcagtggaac gaaaactcac    8460
gttaagggat tttggtcatg agattatcaa aaaggatctt cacctagatc cttttaaatt    8520
aaaaatgaag ttttaaatca atctaaagta tatatgagta aacttggtct ga            8572
```

<210> SEQ ID NO 29
<211> LENGTH: 321
<212> TYPE: PRT
<213> ORGANISM: Unknown
<220> FEATURE:
<223> OTHER INFORMATION: Aquatic organism screen of a metagenomic
      library containing DNA fragments from an environmental sample
      removed from a shipping channel in Laguna Madre, Texas

<400> SEQUENCE: 29

```
Asn Leu Lys Ala Gln Gly Ala Thr Val Met Lys Pro Val Val Pro Phe
1               5                   10                  15

Ile Ala Arg Met Ser Ala Glu Glu Arg Ala Glu Trp Met Ala Gln Phe
            20                  25                  30

Glu Arg Leu Met Pro Gln Ile Asp Val Arg Pro Leu Ala Thr Met Asp
        35                  40                  45

Ala Ala Glu Arg Leu Ser Ala Arg Val Ala Ile Val Ala Asn Pro Asp
    50                  55                  60

Pro Ala His Leu His Glu Leu Pro Gly Leu Val Trp Val Gln Ser Leu
65                  70                  75                  80

Trp Ala Gly Val Glu Arg Leu Leu Gly Glu Leu Ile Asp Thr Asp Phe
                85                  90                  95

Ala Ile Val Arg Met Thr Asp Pro Gln Leu Ala Glu Thr Met Ala Glu
            100                 105                 110

Ala Val Leu Ala Phe Ser Leu Tyr Leu His Arg Asp Ile Pro Leu Tyr
        115                 120                 125

Leu Ala Gln Gln Arg Glu Lys Ile Trp Ala Glu Ala Leu Pro Arg Leu
    130                 135                 140

Ala Ala Asp Arg His Ile Gly Ile Leu Gly Leu Gly Asn Leu Gly Lys
145                 150                 155                 160

Ala Ala Ala Arg Arg Leu Leu Ala Asn Gly Phe Pro Val Ser Gly Trp
                165                 170                 175

Ser Arg Thr Pro Ala Glu Val Glu Gly Ala Glu Cys Phe Ser Gly Glu
            180                 185                 190

Glu Gly Leu Gln Arg Val Leu Ser Arg Ser Asp Ile Val Val Val Leu
        195                 200                 205

Leu Pro Leu Thr Pro Asp Thr Arg Gly Leu Leu Asn Thr Ala Arg Leu
    210                 215                 220

Ala Met Leu Pro Arg Gly Ala Gly Leu Ile Asn Phe Gly Arg Gly Pro
225                 230                 235                 240
```

```
Ile Val Asp Gln Pro Ala Leu Leu Ala Ala Leu Asp Glu Gly His Leu
            245                 250                 255

Ser His Ala Val Leu Asp Val Phe Ala Gln Glu Pro Leu Pro Val Asp
            260                 265                 270

Asn Pro Cys Trp Ser His Pro Ser Val Thr Val Leu Pro His Ile Ser
            275                 280                 285

Ala Pro Thr Thr Pro Ala Thr Ala Ala Arg Ile Val Ala Ala Asn Leu
            290                 295                 300

Ser Ala Tyr Phe Glu Arg Gly Glu Ile Pro Pro Ala Val Asp Arg Gln
305                 310                 315                 320

Arg

<210> SEQ ID NO 30
<211> LENGTH: 220
<212> TYPE: DNA
<213> ORGANISM: Artificial Sequence
<220> FEATURE:
<223> OTHER INFORMATION: trcE promoter

<400> SEQUENCE: 30
tgttgacaat taatcatccg gctcgtataa tgtgtggaat tgtgagcgga taacaatttc        60
acacaggaaa cagcgccgct gagaaaaagc gaagcggcac tgctctttaa caatttatca      120
gacaatctgt gtgggcactc gaccggaatt atcgattaac tttattatta aaaattaaag      180
aggtatatat taatgtatcg attaaataag gaggaataaa                            220
```